US010577650B2

United States Patent
Zimmermann et al.

(10) Patent No.: US 10,577,650 B2
(45) Date of Patent: Mar. 3, 2020

(54) COMPOSITIONS AND METHODS FOR IDENTIFYING NUCLEIC ACID MOLECULES

(71) Applicant: Natera, Inc., San Carlos, CA (US)

(72) Inventors: Bernhard Zimmermann, Manteca, CA (US); Ryan Swenerton, San Bruno, CA (US); Matthew Rabinowitz, San Francisco, CA (US); Styrmir Sigurjonsson, San Jose, CA (US); George Gemelos, Portland, OR (US); Apratim Ganguly, Daly City, CA (US); Himanshu Sethi, Sunnyvale, CA (US)

(73) Assignee: Natera, Inc., San Carlos, CA (US)

( * ) Notice: Subject to any disclaimer, the term of this patent is extended or adjusted under 35 U.S.C. 154(b) by 241 days.

(21) Appl. No.: 15/716,331

(22) Filed: Sep. 26, 2017

(65) Prior Publication Data

US 2018/0155776 A1  Jun. 7, 2018

Related U.S. Application Data

(62) Division of application No. 15/372,279, filed on Dec. 7, 2016, now Pat. No. 10,011,870.

(51) Int. Cl.
*C12Q 1/6869* (2018.01)
*C12Q 1/6806* (2018.01)

(52) U.S. Cl.
CPC ........ *C12Q 1/6869* (2013.01); *C12Q 1/6806* (2013.01); *C12Q 2525/179* (2013.01); *C12Q 2535/122* (2013.01); *C12Q 2563/179* (2013.01)

(58) Field of Classification Search
None
See application file for complete search history.

(56) References Cited

U.S. PATENT DOCUMENTS

| | | |
|---|---|---|
| 5,635,366 A | 6/1997 | Cooke et al. |
| 5,716,776 A | 2/1998 | Bogart |
| 5,753,467 A | 5/1998 | Jensen et al. |
| 5,824,467 A | 10/1998 | Mascarenhas |
| 5,860,917 A | 1/1999 | Comanor et al. |
| 5,972,602 A | 11/1999 | Hyland et al. |
| 5,994,148 A | 11/1999 | Stewart et al. |
| 6,001,611 A | 12/1999 | Will |
| 6,025,128 A | 2/2000 | Veltri et al. |
| 6,066,454 A | 5/2000 | Lipshutz et al. |
| 6,100,029 A | 8/2000 | Lapidus et al. |
| 6,108,635 A | 8/2000 | Herren et al. |
| 6,124,120 A | 9/2000 | Lizardi |
| 6,143,496 A | 11/2000 | Brown et al. |
| 6,156,504 A | 12/2000 | Gocke et al. |
| 6,180,349 B1 | 1/2001 | Ginzinger |
| 6,214,558 B1 | 4/2001 | Shuber et al. |
| 6,258,540 B1 | 7/2001 | Lo et al. |
| 6,300,077 B1 | 10/2001 | Shuber et al. |
| 6,479,235 B1 | 11/2002 | Schumm et al. |
| 6,440,706 B1 | 12/2002 | Vogelstein et al. |
| 6,489,135 B1 | 12/2002 | Parrott et al. |
| 6,720,140 B1 | 4/2004 | Hartley et al. |
| 6,794,140 B1 | 9/2004 | Goldsborough |
| 6,807,491 B2 | 10/2004 | Pavlovic et al. |
| 6,852,487 B1 | 10/2005 | Barany et al. |
| 6,958,211 B2 | 10/2005 | Vingerhoets et al. |
| 6,964,847 B1 | 11/2005 | Englert |
| 7,035,739 B2 | 4/2006 | Schadt et al. |
| 7,058,517 B1 | 6/2006 | Denton et al. |
| 7,058,616 B1 | 6/2006 | Larder et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,414,118 B1 | 8/2008 | Mullah et al. |
| 7,442,506 B2 | 12/2008 | Dhallan |
| 7,459,273 B2 | 12/2008 | Jones et al. |
| 7,645,576 B2 | 1/2010 | Lo et al. |
| 7,700,325 B2 | 5/2010 | Cantor et al. |
| 7,718,367 B2 | 5/2010 | Lo et al. |
| 7,718,370 B2 | 6/2010 | Dhallan |
| 7,727,720 B2 | 9/2010 | Dhallan |
| 7,805,282 B2 | 11/2010 | Casey |
| 7,838,647 B2 | 11/2010 | Hahn et al. |
| 7,888,017 B2 | 8/2011 | Quake |
| 8,008,018 B2 | 9/2011 | Quake et al. |
| 8,024,128 B2 | 9/2011 | Rabinowitz |
| 8,133,719 B2 | 3/2012 | Drmanac et al. |
| 8,137,912 B2 | 5/2012 | Kapur et al. |
| 8,173,370 B2 | 5/2012 | Oeth et al. |
| 8,168,389 B2 | 6/2012 | Shoemaker et al. |
| 8,195,415 B2 | 10/2012 | Fan et al. |

(Continued)

FOREIGN PATENT DOCUMENTS

| CN | 1650032 A | 8/2005 |
|---|---|---|
| CN | 1674028 A | 9/2005 |

(Continued)

OTHER PUBLICATIONS

Anker, P. et al., "Detection of circulating tumour DNA in the blood (plasma/serum) of cancer patients", Cancer and Metastasis Reviews, vol. 18, 1999, 65-73.
Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.
Bianchi, D. W. et al., "Genome-Wide Fetal Aneuploidy Detection by Maternal Plasma DNA Sequencing", Obstetrics & Gynecology, vol. 119, No. 5, May 2012, 890-901.
Chan, K.C. et al., "Size Distributions of Maternal and Fetal DNA in Maternal Plasma", Clinical Chemistry, vol. 50, No. 1, 2004, 88-92.
Chen, X. Q. et al., "Microsatallite alterations in plasma DNA of small cell lung cancer patients", Nature Medicine, vol. 2, No. 9, Sep. 1996, 1033-1035.

(Continued)

*Primary Examiner* — Samuel C Woolwine

(57) ABSTRACT

The present disclosure provides methods and compositions for sequencing nucleic acid molecules and identifying individual sample nucleic acid molecules using Molecular Index Tags (MITs). Furthermore, reaction mixtures, kits, and adapter libraries are provided.

6 Claims, 5 Drawing Sheets

Specification includes a Sequence Listing.

(56) References Cited

U.S. PATENT DOCUMENTS

| | | |
|---|---|---|
| 8,296,076 B2 | 11/2012 | Fan et al. |
| 8,304,187 B2 | 11/2012 | Fernando |
| 8,318,430 B2 | 11/2012 | Chuu et al. |
| 8,450,063 B2 | 5/2013 | Dube et al. |
| 8,467,976 B2 | 8/2013 | Lo et al. |
| 8,515,679 B2 | 9/2013 | Rabinowitz et al. |
| 8,532,930 B2 | 9/2013 | Rabinowitz et al. |
| 8,682,592 B2 | 3/2014 | Rabinowitz et al. |
| 8,825,412 B2 | 9/2014 | Rabinowitz et al. |
| 9,085,798 B2 | 7/2015 | Chee |
| 9,323,888 B2 | 4/2016 | Rava et al. |
| 9,476,095 B2 | 10/2016 | Vogelstein et al. |
| 9,487,829 B2 | 11/2016 | Vogelstein et al. |
| 9,598,731 B2 | 3/2017 | Talasaz |
| 9,677,118 B2 | 6/2017 | Zimmermann et al. |
| 10,081,839 B2 | 9/2018 | Rabinowitz et al. |
| 10,083,273 B2 | 9/2018 | Rabinowitz et al. |
| 10,308,981 B2 | 6/2019 | Sparks et al. |
| 2001/0051341 A1 | 12/2001 | Lo et al. |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2003/0009295 A1 | 1/2003 | Markowitz et al. |
| 2003/0065535 A1 | 4/2003 | Karlov et al. |
| 2003/0077586 A1 | 4/2003 | Pavlovic et al. |
| 2003/0101000 A1 | 5/2003 | Bader et al. |
| 2003/0119004 A1 | 6/2003 | Wenz et al. |
| 2003/0228613 A1 | 12/2003 | Bornarth et al. |
| 2004/0033596 A1 | 2/2004 | Threadgill et al. |
| 2004/0137470 A1 | 7/2004 | Dhallan et al. |
| 2004/0146866 A1 | 7/2004 | Fu |
| 2004/0157243 A1 | 8/2004 | Huang et al. |
| 2004/0197797 A1 | 10/2004 | Inoko et al. |
| 2004/0209299 A1 | 10/2004 | Pinter et al. |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0049793 A1 | 3/2005 | Paterlini-brechot |
| 2005/0053950 A1 | 3/2005 | Ubani et al. |
| 2005/0079535 A1 | 4/2005 | Kirchgesser et al. |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2006/0019278 A1 | 1/2006 | Lo et al. |
| 2006/0040300 A1 | 2/2006 | Dapprich et al. |
| 2006/0052945 A1 | 3/2006 | Rabinowitz et al. |
| 2006/0057618 A1 | 3/2006 | Piper et al. |
| 2006/0068394 A1 | 3/2006 | Langmore et al. |
| 2006/0088574 A1 | 4/2006 | Manning et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216738 A1 | 9/2006 | Wada et al. |
| 2006/0281105 A1 | 12/2006 | Li et al. |
| 2007/0020640 A1 | 1/2007 | McCloskey et al. |
| 2007/0027636 A1 | 2/2007 | Rabinowitz |
| 2007/0042384 A1 | 2/2007 | Li et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0096766 A1 | 4/2008 | Lee |
| 2008/0102455 A1 | 5/2008 | Poetter |
| 2008/0138809 A1 | 6/2008 | Kapur et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2008/0305473 A1 | 12/2008 | Chowdary et al. |
| 2009/0023190 A1 | 1/2009 | Lao et al. |
| 2009/0029377 A1 | 1/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176662 A1 | 7/2009 | Rigatti et al. |
| 2009/0221620 A1 | 9/2009 | Luke et al. |
| 2010/0035232 A1 | 2/2010 | Ecker et al. |
| 2010/0112575 A1 | 5/2010 | Fan et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129874 A1 | 5/2010 | Mitra et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273678 A1 | 10/2010 | Alexandre et al. |
| 2010/0285537 A1 | 11/2010 | Zimmermann |
| 2010/0291572 A1 | 11/2010 | Stoughton et al. |
| 2010/0291635 A1 | 11/2010 | Peleg |
| 2010/0323352 A1 | 12/2010 | Lo et al. |
| 2011/0033862 A1 | 2/2011 | Rabinowitz et al. |
| 2011/0039724 A1 | 2/2011 | Lo et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0201507 A1 | 8/2011 | Rava et al. |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0300608 A1 | 12/2011 | Ryan et al. |
| 2011/0301854 A1 | 12/2011 | Curry et al. |
| 2011/0318734 A1 | 12/2011 | Lo et al. |
| 2012/0003635 A1 | 1/2012 | Lo et al. |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0108460 A1 | 5/2012 | Quake et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |

(56) References Cited

U.S. PATENT DOCUMENTS

| | | |
|---|---|---|
| 2012/0191358 A1 | 7/2012 | Oliphant et al. |
| 2012/0196754 A1 | 8/2012 | Quake et al. |
| 2012/0214678 A1 | 8/2012 | Rava et al. |
| 2012/0264121 A1 | 10/2012 | Rava et al. |
| 2012/0270212 A1 | 10/2012 | Rabinowitz et al. |
| 2012/0295810 A1 | 11/2012 | Quake et al. |
| 2012/0295819 A1 | 11/2012 | Leamon et al. |
| 2013/0017549 A1 | 1/2013 | Hong |
| 2013/0024127 A1 | 1/2013 | Stuelpnagel |
| 2013/0034546 A1 | 2/2013 | Rava et al. |
| 2013/0060483 A1 | 3/2013 | Struble et al. |
| 2013/0069869 A1 | 3/2013 | Akao et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0252824 A1 | 9/2013 | Rabinowitz et al. |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |
| 2013/0323731 A1 | 12/2013 | Lo et al. |
| 2014/0032128 A1 | 1/2014 | Rabinowitz et al. |
| 2014/0038830 A1 | 2/2014 | Srinivasan et al. |
| 2014/0051585 A1 | 2/2014 | Prosen et al. |
| 2014/0065621 A1 | 3/2014 | Mhatre et al. |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0141981 A1 | 5/2014 | Zimmermann et al. |
| 2014/0154682 A1 | 6/2014 | Rabinowitz et al. |
| 2014/0155274 A1 | 6/2014 | Xie et al. |
| 2014/0162269 A1 | 6/2014 | Rabinowitz |
| 2014/0193816 A1 | 7/2014 | Rabinowitz et al. |
| 2014/0206552 A1 | 7/2014 | Rabinowitz et al. |
| 2014/0227705 A1 | 8/2014 | Vogelstein et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0287934 A1 | 9/2014 | Szelinger et al. |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0064695 A1 | 3/2015 | Katz et al. |
| 2015/0147815 A1 | 5/2015 | Babiarz et al. |
| 2015/0197786 A1 | 7/2015 | Osborne et al. |
| 2015/0232938 A1 | 8/2015 | Mhatre |
| 2015/0265995 A1 | 9/2015 | Head et al. |
| 2016/0201124 A1 | 7/2016 | Donahue et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2017/0121716 A1 | 5/2017 | Rodi et al. |
| 2018/0148777 A1 | 5/2018 | Kirkizlar et al. |
| 2018/0155775 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsson et al. |
| 2018/0173846 A1 | 6/2018 | Sigurjonsson et al. |
| 2018/0201995 A1 | 7/2018 | Rabinowitz et al. |
| 2018/0237841 A1 | 8/2018 | Stray et al. |
| 2018/0298439 A1 | 10/2018 | Ryan et al. |
| 2018/0300448 A1 | 10/2018 | Rabinowitz et al. |
| 2019/0010543 A1 | 1/2019 | Babiarz et al. |
| 2019/0106751 A1 | 4/2019 | Zimmermann et al. |
| 2019/0185913 A1 | 6/2019 | Zimmermann et al. |
| 2019/0185936 A1 | 6/2019 | Babiarz et al. |
| 2019/0194743 A1 | 6/2019 | Ryan et al. |
| 2019/0194758 A1 | 6/2019 | Babiarz et al. |
| 2019/0194759 A1 | 6/2019 | Babiarz et al. |
| 2019/0203290 A1 | 7/2019 | Rabinowitz et al. |
| 2019/0203294 A1 | 7/2019 | Babiarz et al. |
| 2019/0211391 A1 | 7/2019 | Rabinowitz et al. |
| 2019/0211392 A1 | 7/2019 | Rabinowitz et al. |
| 2019/0211393 A1 | 7/2019 | Rabinowitz et al. |
| 2019/0211399 A1 | 7/2019 | Rabinowitz et al. |
| 2019/0211402 A1 | 7/2019 | Babiarz et al. |
| 2019/0211406 A1 | 7/2019 | Babiarz et al. |

FOREIGN PATENT DOCUMENTS

| | | |
|---|---|---|
| CN | 101675169 A | 3/2010 |
| EP | 0270017 A2 | 6/1988 |
| EP | 1524321 A1 | 4/2005 |
| EP | 1524321 B1 | 7/2009 |
| EP | 2163622 A1 | 3/2010 |
| EP | 2128169 A1 | 12/2010 |
| EP | 2902500 A1 | 8/2015 |
| GB | 2488358 | 8/2012 |
| JP | 2965699 | 8/1999 |
| JP | 2002-530121 A | 9/2002 |
| JP | 2004502466 A | 1/2004 |
| JP | 2004533243 A | 11/2004 |
| JP | 2005514956 A | 5/2005 |
| JP | 2005160470 A | 6/2005 |
| JP | 2006-254912 A | 9/2006 |
| JP | 2011/516069 A | 5/2011 |
| RU | 2290078 C1 | 12/2006 |
| WO | 179851 A1 | 10/2001 |
| WO | 200190419 A2 | 11/2001 |
| WO | 2002004672 A2 | 1/2002 |
| WO | 2002055985 A2 | 7/2002 |
| WO | 2002076377 | 10/2002 |
| WO | 2003031646 A1 | 4/2003 |
| WO | 3050532 A1 | 6/2003 |
| WO | 2003062441 A1 | 7/2003 |
| WO | 0190419 A9 | 11/2003 |
| WO | 3102595 A1 | 12/2003 |
| WO | 3106623 A2 | 12/2003 |
| WO | 2004087863 A2 | 10/2004 |
| WO | 2005021793 A1 | 3/2005 |
| WO | 2005035725 A2 | 4/2005 |
| WO | 2005100401 A2 | 10/2005 |
| WO | 2005123779 A2 | 12/2005 |
| WO | 2007057647 A1 | 5/2007 |
| WO | 2007062164 A3 | 5/2007 |
| WO | 2007070482 A2 | 6/2007 |
| WO | 2007/117256 A1 | 10/2007 |
| WO | 2007132167 A2 | 11/2007 |
| WO | 2007/147076 A2 | 12/2007 |
| WO | 2007147074 A2 | 12/2007 |
| WO | 2008024473 A2 | 2/2008 |
| WO | 2008048931 A1 | 4/2008 |
| WO | 2008051928 A2 | 5/2008 |
| WO | 2008059578 A1 | 5/2008 |
| WO | 2008081451 A2 | 7/2008 |
| WO | 2008115497 A2 | 9/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009/036525 A2 | 3/2009 |
| WO | 2009030100 A1 | 3/2009 |
| WO | 2009032779 A2 | 3/2009 |
| WO | 2009032781 A2 | 3/2009 |
| WO | 2009033178 A1 | 3/2009 |
| WO | 2009091934 A1 | 7/2009 |
| WO | 2009092035 A2 | 7/2009 |
| WO | 2009105531 A1 | 8/2009 |

(56) References Cited

FOREIGN PATENT DOCUMENTS

| WO | 2009146335 | A1 | 12/2009 |
|---|---|---|---|
| WO | 2010017214 | A1 | 2/2010 |
| WO | 2010/033652 | A1 | 3/2010 |
| WO | 2010075459 | | 7/2010 |
| WO | 2011041485 | A1 | 4/2011 |
| WO | 2011/057061 | A1 | 5/2011 |
| WO | 2011057094 | | 5/2011 |
| WO | 2011/090556 | A1 | 7/2011 |
| WO | 2011087760 | | 7/2011 |
| WO | 2011146632 | A1 | 11/2011 |
| WO | 2012/028746 | A1 | 3/2012 |
| WO | 201283250 | | 6/2012 |
| WO | 2012088456 | A2 | 6/2012 |
| WO | 20120071621 | | 6/2012 |
| WO | 2012108920 | A1 | 8/2012 |
| WO | 2012/142531 | A2 | 10/2012 |
| WO | 2007/149791 | A2 | 12/2012 |
| WO | 2013030577 | | 3/2013 |
| WO | 2013/045432 | A1 | 4/2013 |
| WO | 2013052557 | A2 | 4/2013 |
| WO | 2013/078470 | A2 | 5/2013 |
| WO | 2013/086464 | A1 | 6/2013 |
| WO | 20130130848 | | 9/2013 |
| WO | 2013/159035 | A2 | 10/2013 |
| WO | 2013/181651 | A1 | 12/2013 |
| WO | 2014/004726 | A1 | 1/2014 |
| WO | 2014/014497 | A1 | 1/2014 |
| WO | 20140018080 | | 1/2014 |
| WO | 2014/035986 | A1 | 3/2014 |
| WO | 2014/122288 | A1 | 8/2014 |
| WO | 2014/149134 | A2 | 9/2014 |
| WO | 2014/151117 | A1 | 9/2014 |
| WO | 2015/100427 | A1 | 7/2015 |
| WO | 2015/164432 | A1 | 10/2015 |
| WO | 2016/009059 | A1 | 1/2016 |
| WO | 2016/065295 | A1 | 4/2016 |
| WO | 2016/138080 | A1 | 9/2016 |
| WO | 2016/193490 | A1 | 12/2016 |
| WO | 2017/058784 | A1 | 4/2017 |
| WO | 2017/181146 | A1 | 10/2017 |
| WO | 2017/181202 | A2 | 10/2017 |
| WO | 2018/083467 | A1 | 5/2018 |
| WO | 2018/106798 | A1 | 6/2018 |
| WO | 2018/156418 | A1 | 8/2018 |
| WO | 2019/140298 | A1 | 7/2019 |

OTHER PUBLICATIONS

Dodge, Y., "Bayes' Theorem", The Concise Encyclopedia of Statistics, 2008, 30-31.
Geiss, G. K. et al., "Direct multiplexed measurement of gene expression with color-coded probe pairs", Nature Biotechnology, vol. 26, No. 3, Feb. 17, 2008, 317-325.
Gunderson, K. L. et al., "A genome-wide scalable SNP genotyping assay using microarray technology", Nature Genetics, vol. 37, No. 5, May 2005, 549-554.
Jenkins, S. et al., "High-throughput SNP genotyping", Comparative and Functional Genomics, vol. 3, Dec. 5, 2001, 57-66.
Kwok, P. Y., "High-throughput genotyping assay approaches", Pharmacogenomics, vol. 1, No. 1, 2000, 1-5.
Lander, E. S. et al., "Initial sequencing and analysis of the human genome", Nature, vol. 409, Feb. 15, 2001, 860-921.
Levsky, J. M. et al., "Fluorescence in situ hybridization: past, present and future", Journal of Cell Science, vol. 116, No. 14, 2003, 2833-2838.
Palomaki, G. E. et al., "DNA sequencing of maternal plasma to detect Down syndrome: An international clinical validation study", Genetics in Medicine, vol. 13, No. 1, Nov. 2011, 913-920.
Quinn, G. P. et al., "Experimental Design and Data Analysis for Biologists", Graphical Exploration of Data, 2002, 64-67.
Tebbutt, S. J. et al., "Microarray genotyping resource to determine population stratification in genetic association studies of complex disease", BioTechniques, vol. 37, Dec. 2004, 977-985.

Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.
Cansar, "Hs-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.
Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.
Choi, M. et al., "Genetic diagnosis by whole exome capture and massively parallel DNA sequencing", PNAS, vol. 106, No. 45, Nov. 10, 2009, 19096-19101.
Garcia-Murillas, I. et al., "Mutation tracking in circulating tumor DNA predicts relapse in early breast cancer", Science Translational Medicine, vol. 7, No. 302, Aug. 26, 2015, 1-2.
Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.
Jamal-Hanjani, M. et al., "Tracking the Evolution of Non-Small-Cell Lung Cancer", The New England Journal of Medicine, vol. 376, No. 22, Jun. 1, 2017, 2109-2121.
Jarvie, T., "Next generation sequencing technologies", Drug Discovery Today: Technologies, vol. 2, No. 3, 2005, 255-260.
Kim, H. et al., "Whole-genome and multisector exome sequencing of primary and post-treatment glioblastoma reveals patterns of tumor evolution", Genome Research, vol. 25, No. 3, Feb. 3, 2015, 316-327.
Leary, R. J. et al., "Development of Personalized Tumor Biomarkers Using Massively Parallel Sequencing", Science Translational Medicine, vol. 2, No. 20, Feb. 24, 2010, 1-8.
Ma, Xiaotu et al., "Rise and fall of subclones from diagnosis to relapse in pediatric B-acute lymphoblastic leukaemia", Nature Communications, vol. 6, Mar. 19, 2015, 1-12.
Margulies, M. et al., "Genome sequencing in microfabricated high-density picolitre reactors", Nature, vol. 437, Sep. 15, 2005, 376-380.
Margulies, M. et al., "Genome sequencing in microfabricated high-density picolitre reactors plus Supplemental Methods", Nature, vol. 437, Sep. 15, 2005, 40 pgs.
McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.
Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.
Pergament, E. et al., "Single-Nucleotide Polymorphism-Based Non-invasive Prenatal Screening in a High-Risk and Low-Risk Cohort", Obstetrics & Gynecology, vol. 124, No. 2, Part 1, Aug. 2014, 210-218 + Appendices.
Popova, T. et al., "Genome Alteration Print (GAP): a tool to visualize and mine complex cancer genomic profiles obtained by SNP arrays", Genome Biology, vol. 10, R128, Nov. 11, 2009, 1-14.
Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.
Samango Sprouse, C. et al., "SNP-based non-invasive prenatal testing detects sex chromosome aneuploidies with high accuracy", Prenatal Diagnosis, vol. 33, 2013, 643-649.
Abbosh, C. et al., "Phylogenetic ctDNA analysis depicts early-stage lung cancer evolution", Nature, vol. 545, May 25, 2017, 446-451.
Carvalho, B. et al., "Exploration, normalization, and genotype calls of high-density oligonucleotide SNP array data", Biostatistics, vol. 8, No. 2, 2007, 485-499.
De Bruin, E. et al., "Spatial and temporal diversity in genomic instability processes defines lung cancer evolution", Science, vol. 346, No. 6206, Oct. 10, 2014, 251-256.

(56) References Cited

OTHER PUBLICATIONS

Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Ford, E. et al., "A method for generating highly multiplexed ChIP-seq libraries", BMC Research Notes, vol. 7, No. 312, May 22, 2014, 1-5.
Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.
Jamal-Hanjani, M. et al., "Tracking Genomic Cancer Evolution for Precision Medicine: The Lung TRACERx Study", PLOS Biology, vol. 12, No. 7, Jul. 2014, 1-7.
Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.
Rogaeva, E. et al., "The Solved and Unsolved Mysteries of the Genetics of Early-Onset Alzheimer's Disease", NeuroMolecular Medicine, vol. 2, 2002, 1-10.
Thermofisher Scientific, "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.
Wapner, R. et al., "First-Trimester Screening for Trisomies 21 and 18", The New England Journal of Medicine, vol. 349, No. 15, Oct. 9, 2003, 1405-1413.
Xu, S. et al., "Circulating tumor DNA identified by targeted sequencing in advanced-stage non-small cell lung cancer patients", Cancer Letters, vol. 370, 2016, 324-331.
Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.
"Blast of AAAAAAAAATTTAAAAAAAAATTT(http://blast.ncbi.nlm.nih.gov/Blast.cgi, downloaded May 4, 2015)".
"CompetitivePCR Guide,", TaKaRa Biomedicals, Lit. # L0126 Rev. Aug. 1999, 9 pgs.
"db SNP rs2056688 (http://www.ncbi.nlm.nih.gov/projects/SNP/snp_ref.cgi?rs=2056688, downloaded May 4, 2015".
"Declaration by Dr. Zimmerman of Oct. 30, 2014 filed in U.S. Appl. No. 14/044,434".
"European Application No. 014198110, European Search Report dated Apr. 28, 2015, 3 pages."
"Finishing the Euchromatic Sequence of the Human Genome", Nature vol. 431,(Oct. 21, 2004),931-945.
"FixedMedium, dictionary definition, Academic Press Dictionary of Science andTechnology", Retrieved from the Internet: <URL:www.credoreference.com/entry/apdst/fixed_medium>, 1996, 1 pg.
"GeneticsHome Reference", http://ghr.nlm.nih.gov/handbook/genomicresearch/snp, Feb. 28, 2014, 1-2.
"Guideline related to genetic examination", Societies Related to Genetic Medicine, Japanese Society for Genetic Counseling, Japanese Society for Gene Diagnosis and Therapy, Japan Society of Obstetrics an, 2003, 2-15.
"Ion Ampli Seq Comprehensive Cancer Panel, product brochure, Life TechnologiesCorporation. Retrieved from the Internet", <URL:https://tools.lifetechnologies.com/content/sfs/brochures/Ion_Comp CancerPanel_Flyer.pdf>, 2012, 2 pgs.
"IonAmpliSeq Designer Provides Full Flexibility to Sequence Genes of Your Choice,product brochure, Life Technologies Corporation", Retrieved from the Internet<URL: http://tools.lifetechnologies.com/content/sfs/brochures/IonAmpliSeq_CustomPanels_AppNote_CO1.
"Merriam-Webster.com (http://www.merriam-webster.com/dictionary/universal, downloaded Jul. 23, 2014)".
"Multiplexing with RainDrop Digital PCR", RainDance Technologies, Application Note, 2013, 1-2.
"NucleicAcids, Linkers and Primers: Random Primers", New England BioLabs 1998/99Catalog, 1998, 121 and 284.
"PRIMER3, information sheet, Sourceforge.net. [retrieved on Nov. 12, 2012]. Retrieved from the Internet: <URL:http://primer3.sourceforge.net/>", 2009, 1 pg.
"www.fatsecret.com" (printed from internet Nov. 1, 2014).
PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010).
The Bump (Panorama Test, attached, Jul. 1, 2013).
What to Expect (Weird Harmony results, attached, May 1, 2015).
Wikipedia (attached, available at https://en.wikipedia.org/wiki/Stimulant, accessed Mar. 14, 2016).
"How Many Carbs in a Potato?, [Online]", Retrieved from the Internet: <http://www.newhealthguide.org/How-Many-Carbs-In-A-Potato.html>, Nov. 1, 2014, 3 pages.
"Random variable", In the Penguin Dictionary of Mathematics. Retrieved from http://www.credoreference.com/entry/penguinmath/random_variable, 2008, 1 page.
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.
Agarwal, Ashwin. et al., "Commercial Landscape of Noninvasive Prenatal Testing in the United States", Prenatal Diagnosis,33, 2013, 521-531.
Alkan, Can et al., "Personalized Copy Number and Segmental Duplication Maps Using Next-Generation Sequencing", Nature Genetics, 41, 10, 2009, 1061-1068.
Allaire, F R. , "Mate selection by selection index theory", Theoretical Applied Genetics, 57(6), 1980, 267-272.
Allawi, Hatim T. et al., "Thermodynamics of internal C•T Mismatches in DNA", Nucleic Acids Research, 26 (11), 1998, 2694-2701.
Aoki, Yasuhiro, "Statistical and Probabilistic Bases of Forensic DNA Testing", The Journal of the Iwate Medical Association, 2002, vol. 54, p. 81-94.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.
Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Bada, Michael A. et al., "Computational Modeling of Structural Experimental Data", Methods in Enzymology,317, 2000, 470-491.
Beaumont, Mark A et al., "The Bayesian Revolution in Genetics", Nature Reviews Genetics, 5, 2004, 251-261.
Beer, Alan E. et al., "The Biological Basis of Passage of Fetal Cellular Material into the Maternal Circulation", Annals New York Academy of Sciences, 731, 1994, 21-35.
Beerenwinkel, et al., "Methods for Optimizing Antiviral Combination Therapies", Bioinformatics, 19(1), 2003, i16-i25.
Beerenwinkel, N. et al., "Geno2pheno: estimating phenotypic drug resistance from HIV-1 genotypes", Nucleic Acids Research, 31(13), 2003, 3850-3855.
Benn, P. et al., "Non-Invasive Prenatal Testing for Aneuploidy: Current Status and Future Prospects", Ultrasound Obstet Gynecol, 42, 2013, 15-33.
Benn, P et al., "Non-Invasive prenatal Diagnosis for Down Syndrome: the Paradigm Will Shift, but Slowly", Ultrasound Obstet. Gynecol., 39, 2012, 127-130.
Bentley, David R et al., "Accurate Whole Human Genome Sequencing Using Reversible Terminator Chemistry", Nature, 456, 6, 2008, 53-59.
Bermudez, M. et al., "Single-cell sequencing and mini-sequencing for preimplantation genetic diagnosis", Prenatal Diagnosis, 23, 2003, 669-677.
Bevinetto, Gina, Bevinetto (5 Foods All Pregnant Women Need, American Baby, available at http://www.parents.com/pregnancy/mybody/nutrition/ 5greatpregnancyfoods/, Apr. 15, 2008).

(56) References Cited

OTHER PUBLICATIONS

Bianchi, D W. et al., "Fetal gender and aneuploidy detection using fetal cells maternal blood: analysis of NIFTY I data", Prenat Diagn 2002; 22, 2002, 609-615.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Bisignano, et al., "PGD and Aneuploidy Screening for 24 Chromosomes: Advantages and Disadvantages of Competing Platforms", Reproductive BioMedicine Online, 23, 2011, 677-685.
Bodenreider, O., "The Unified Medical Language System (UMLS): Integrating Biomedical Terminology", Nucleic Acids Research, 32, (Database issue), 2004, D267-D270.
Breithaupt, Holger, "The Future of Medicine", EMBO Reports, 21(61), 2001, 465-467.
Brownie, Jannine et al., "The Elimination of Primer-Dimer Accumulation in PCR", Nucleic Acids Research, 25(16), 1997, 3235-3241.
Butler, J. et al., "The Development of Reduced Size STR Amplicons as Tools for Analysis of Degraded DNA*", Journal of Forensic Sciences, vol. 48, No. 5, 2003, 1054-1064.
Cairns, Paul et al., "Homozygous Deletions of 9p21 in Primary Human Bladder Tumors Detected by Comparative Multiplex Polymerase Chain Reaction", Cancer Research, 54, 1994, 1422-1424.
Caliendo, Angela, "Multiplex PCR and Emerging Technologies for the Detection of Respiratory Pathogens", Clinical Infectious Diseases, 52(4), 2011, S326-S330.
Carnevale, Alessandra et al., "Attitudes of Mexican Geneticists Towards Prenatal Diagnosis and Selective Abortion", American Journal of Medical Genetics, 75, 1998, 426-431.
Casbon, J. A. et al., "A method for counting PCR template molecules with application to next-generation sequencing", Nucleic Acids Research, vol. 39, No. 12, Apr. 13, 2011, 1-8.
Chakraborty, R. et al., "Paternity Exclusion by DNA Markers: Effects of Paternal Mutations", Journal of Forensic Sciences, vol. 41, No. 4, Jul. 1996, 671-677.
Chen, E. et al., "Noninvasive Prenatal Diagnosis of Fetal Trisomy 18 and Trisomy 13 by Maternal Plasma DNA Sequencing", PLoS One, 6 (7), e21791, 2011, 7 pgs.
Chetty, Shilpa et al., "Uptake of Noninvasive Prenatal Testing (NIPT) in Women Following Positive Aneuploidy Screening", Prenatal Diagnosis,33, 2013, 542-546.
Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.
Chiu, Rossa W. et al., "Effects of Blood-Processing Protocols on Fetal and Total DNA Quantification in Maternal Plasma", Clinical Chemistry, 47(9), 2001, 1607-1613.
Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.
Chiu, Rossa W.K. et al., "Non-Invasive Prenatal Diagnosis by Single Molecule Counting Technologies", Trends in Genetics, 25 (7), 2009, 324-331.
Chiu, Rossa W.K. et al., "Noninvasive Prenatal Diagnosis of Fetal Chromosomal Aneuploidy by Massively Parallel Genomic Sequencing of DNA in Maternal Plasma", PNAS, 105, 51 (with Supporting Information), 2008, 23.
Chu, T. et al., "Statistical Considerations for Digital Approaches to Non-Invasive Fetal Genotyping", Bioinformatics (Advance Access publication), 26 (22), 2010, 2863-2866.
Chu, Tianjiao et al., "Statistical Model for Whole Genome Sequencing and its Application to Minimally Invasive Diagnosis of Fetal Genetic Disease", Bioinformatics, 25(10), 2009, 1244-1250.
Chu, Tianjiao. et al., "A Novel Approach Toward the Challenge of Accurately Quantifying Fetal DNA in Maternal Plasma", Prenatal Diagnosis,30, 2010, 1226-1229.
Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.
Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.
Cossu, Gianfranco et al., "Rh D/d Genotyping by Quantitative Polymerase Chain Reaction and Capillary Zone Electrophoresis", Electrophoresis, 17, 1996, 1911-1915.
Coyle, J. F. et al., "Standards for detailed clinical models as the basis for medical data exchange and decision support", International Journal of Medical Informatics, 69(2-3), 2003, 157-174.
Craig, D. W. et al., "Identification of genetic variants using bar-coded multiplexed sequencing", Nature Methods, vol. 5, Oct. 2008, 887-893.
Cross, Jillian et al., "Resolution of trisomic mosaicism in prenatal diagnosis: estimated performance of a 50K SNP microarray", Prenat Diagn 2007; 27, 2007, 1197-1204.
D'Aquila, Richard et al., "Maximizing sensitivity and specificity of PCR by pre-amplification heating", Nucleic Acids Research, 19(13), 1991, p. 3749.
Daruwala, Raoul-Sam et al., "A Versatile Statistical Analysis Algorithm to Detect Genome Copy Number Variation", PNAS, 101(46), 2004, 16292-16297.
De Vries, et al., "Diagnostic genome profiling in mental retardation", Am J Hum Genet, 77, published online Aug. 30, 2005, 2005, 606-616.
Deangelis, M. et al., "Solid-phase Reversible Immobilization for the Isolation of PCR Products", Nucleic Acids Research, 23 (22), 1995, 4742-4743.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circulation", JAMA, 291(9), 2004, 1114-1119.
Dhallan, Ravinder et al., "A non-invasive test for prenatal diagnosis based on fetal DNA present in maternal blood: a preliminary study", The Lancet, 369, 2007, 474-481.
Dieffenbach, C W. et al., "General concepts for PCR primer design", Genome Research. PCR methods and Applications vol. 3, 1993, S30-S37.
Ding, C et al., "Direct molecular haplotyping of long-range genomic DNA with M1-PCR", PNAS 100(13), 2003, 7449-7453.
Dohm, J. et al., "Substantial Biases in Ultra-Short Read Data Sets From High-Throughput DNA Sequencing", Nucleic Acids Research, 36 (16), e105, 2008, 10 pgs.
Dolganov, Gregory et al., "A Novel Method of Gene Transcript Profiling in Airway Biopsy Homogenates Reveals Increased Expression of a Na—K+-Cl-Cotransporter (NKCC1) in Asthmatic Subjects", Genome Res.,11, 2001, 1473-1483.
Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.
Donoso, P. et al., "Current Value of Preimplantation Genetic Aneuploidy Screening in IVF", Human Reproduction Update, 13(1), 2007, 15-25.
Echeverri, et al., "Caffeine's Vascular Mechanisms of Action", International Journal of Vascular Medicine vol. 2010(2010), 10 pages, Aug. 25, 2010.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H , "Mild Course of Fetal Rh D Haemolytic Disease due to Maternal Alloimmunisation to Paternal HLA Class I and II Antigens", Vox Sang, 68, 1995, 243-247.
Ellison, Aaron M., "Bayesian Inference in Ecology", Ecology Letters, 2004, vol. 7, p. 509-520.
Ellonen, P. et al., "Development of SNP Microarray for Supplementary Paternity Testing", International Congress Series,1261, 2004, 12-14.

(56) References Cited

OTHER PUBLICATIONS

EP06838311.6, "European Communication and Extended European Search Report", dated Dec. 30, 2008, 8 pgs.
EP08742125.1, "European Communication pursuant to Article 94(3) EPC and Examination Report", dated Feb. 12, 2010, 5 pgs.
Fan, et al., "Whole-genome molecular haplotyping of single cells", Nature Biotechnology, vol. 29, No. 1, Jan. 1, 2011, 51-57.
Fan, Christina H. et al., "Non-Invasive Prenatal Measurement of the Fetal Genome", Nature, doi:10.1038/nature11251, 2012, 26 pgs.
Fan, Christina H et al., "Noninvasive Diagnosis of Fetal Aneuploidy by Shotgun Sequencing DNA from Maternal Blood", PNAS, 105, 42, 2008, 16266-16271.
Fan, H. Christina et al., "Sensitivity of Noninvasive Prenatal Detection of Fetal Aneuploidy from Maternal Plasma Using Shotgun Sequencing Is Limited Only by Counting Statistics", PLoS ONE, vol. 5, Issue 5 (e10439), May 3, 2010, 1-6.
Fan, Jian-Bing et al., "Highly Parallel Genomic Assay", Nature Reviews, 7, 2006, 632-644.
Fazio, Gennaro. et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Forejt, et al., "Segmental trisomy of mouse chromosome 17: introducing an alternative model of Down's syndrome", Genomics, 4(6), 2003, 647-652.
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Fredriksson, et al., "Multiplex amplification of all coding sequences within 10 cancer genes by Gene-Collector", Nucleic Acids Research, 2007, vol. 35, No. 7 e47, 1-6.
Freeman, Jennifer L. et al., "Copy Number Variation: New Insights in Genome Diversity", Genome Research, 16, 2006, 949-961.
Frost, Mackenzie S et al., "Differential Effects of Chronic Pulsatile Versus Chronic Constant Maternal Hyperglycemia on Fetal Pancreatic B-Cells", Journal of Pregnancy, 2012, , Article ID 812094, 2012, 8.
Fu, G. K. et al., "Counting individual DNA molecules by the stochastic attachment of diverse labels", PNAS, vol. 108, No. 22, May 31, 2011, 9026-9031.
Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.
Ganshirt-Ahlert, D. et al., "Ratio of Fetal to Maternal DNA is Less Than 1 in 5000 at different Gestational Ages in Maternal Blood", Clinical Genetics,38, 1990, 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Gardina, P. et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, 9 (489), (doi:10.1186/1471-2164-9-489), 2008, 16 pgs.
Ghanta, Sujana et al., "Non-Invasive Prenatal Detection of Trisomy 21 Using Tandem Single Nucleotide Polymorphisms", PLoS ONE, 5 (10), 2010, 10 pgs.

Gjertson, David W. et al., "Assessing Probability of Paternity and the Product Rule in DNA Systems", Genetica, 96, 1995, 89-98.
Greenwalt, T. et al., "The Quantification of Fetomaternal Hemorrhage by an Enzyme-Linked Antibody Test with Glutaraldehyde Fixation", Vox Sang, 63, 1992, 268-271.
Guerra, J. , "Terminal Contributions for Duplex Oligonucleotide Thermodynamic Properties in the Context of Nearest Neighbor Models", Biopolymers, 95(3), (2010), 2011, 194-201.
Guetta, Esther et al., "Analysis of Fetal Blood Cells in the Maternal Circulation: Challenges, Ongoing Efforts, and Potential Solutions", Stem Cells and Development, 13, 2004, 93-99.
Guichoux, et al., "Current Trends in Microsatellite Genotyping", Molecular Ecology Resources, 11, 2011, 591-911.
Hall, M., "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Hara, Eiji et al., "Subtractive cDNA cloning using oligo(dT)3o-latex and PCR: isolation of cDNA clones specific to undifferentiated human embryonal carcinoma cells", Nucleic Acids Research, 19(25), 1991, 7097-7104.
Hardenbol, P., "Multiplexed Genotyping With Sequence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube assay", Genome Research, 15, 2005, 269-275.
Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Harper, J. C. et al., "Recent Advances and Future Developments in PGD", Prenatal Diagnosis, 19, 1999, 1193-1199.
Harton, G.L. et al., "Preimplantation Genetic Testing for Marfan Syndrome", Molecular Human Reproduction, 2 (9), 1996, 713-715.
Hawkins, T. et al., "Whole genome amplification—applications and advances", Current Opinion in Biotechnology, 13, 2002, 65-67.
Hayden, et al., "Multiplex-Ready PCR: A new method for multiplexed SSR and SNP genotyping", BMC Genomics 2008, 9(80), 1-12.
Hellani, A. et al., "Clinical Application of Multiple Displacement Amplification in Preimplantation Genetic Diagnosis", Reproductive BioMedicine Online, 10 (3), 2005, 376-380.
Hellani, Ali et al., "Multiple displacement amplification on single cell and possible PGD applications", Molecular Human Reproduction, 10(11), 2004, 847-852.
Hojsgaard, S. et al., "BIFROST—Block recursive models induced from relevant knowledge, observations, and statistical techniques", Computational Statistics & Data Analysis, 19(2), 1995, 155-175.
Hollas, B. et al., "A stochastic approach to count RN A molecules using DNA sequencing methods", Lecture Notes in Computer Science, vol. 2812, 2003, 55-62.
Holleley, et al., "Multiplex Manager 1.0: a Cross-Platform Computer Program that Plans and Optimizes Multiplex PCR", BioTechniques46:511-517 (Jun. 2009), 511-517.
Hollox, E. et al., "Extensive Normal Copy Number Variation of a β-Defensin Antimicrobial-Gene Cluster", Am. J. Hum. Genet., 73, 2003, 591-600.
Homer, et al., "Resolving Individuals Contributing Trace Amounts of DNA to Highly Complex Mixtures Using High-Density SNP Genotyping Microarrays", PLOS Genetics, 4(8), 2008, 9 pgs.
Hoogendoorn, Bastiaan et al., "Genotyping Single Nucleotide Polymorphisms by Primer Extension and High Performance Liquid Chromatography", Hum Genet, 104, 1999, 89-93.
Hospital, F. et al., "A General Algorithm to Compute Multilocus Genotype Frequencies Under Various Mating Systems" vol. 12, No. 6, Jan. 1, 1996 (Jan. 1, 1996), pp. 455-462.

(56) References Cited

OTHER PUBLICATIONS

Howie, et al., "Fast and accurate genotype imputation in genome-wide association studies through pre-phasing", Nature Genetics, vol. 44, No. 8, Jul. 22, 2012, 955-959.
Hu, Dong Gui et al., "Aneuploidy Detection in Single Cells Using DNA Array-Based Comparative Genomic Hybridization", Molecular Human Reproduction, 10(4), 2004, 283-289.
Hug, H. et al., "Measurement of the number of molecules of a single mRNA species in a complex mRNA preparation", J. Theor. Biol., vol. 221, 2003, 615-624.
Hultin, E. et al., "Competitive enzymatic reaction to control allele-specific extensions", Nucleic Acids Research, vol. 33, No. 5, Mar. 14, 2005, 1-10.
Ido, Yasuo et al., "Hyperglycemia-Induced Apoptosis in Human Umbilical Vein Endothelial Cells: Inhibition by the Amp-Activated Protein Kinase Activation", Diabetes, 51, 2002, 159-167.
Illumina Catalog, "Paired-End Sample Preparation Guide, Illumina Catalog# PE-930-1 001, Part# 1005063 Rev. E", 2011, 1-40.
Ishii, et al., "Optimization of Annealing Temperature to Reduce Bias Caused by a Primer Mismatch in Multitemplate PCR", Applied and Environmental Microbiology, Aug. 2001, p. 3753-3755.
Jabara, C. B. et al., "Accurate sampling and deep sequencing of the HIV-1 protease gene using a Primer ID", PNAS, vol. 108, No. 50, Dec. 13, 2011, 20166-20171.
Johnson, D.S. et al., "Comprehensive Analysis of Karyotypic Mosaicism Between Trophectoderm and Inner Cell Mass", Molecular Human Reproduction, 16(12), 2010, 944-949.
Johnson D.S, et al., "Preclinical Validation of a Microarray Method for Full Molecular Karyotyping of Blastomeres in a 24-h Protocol", Human Reproduction, 25 (4), 2010, 1066-1075.
Kaplinski, Lauris et al., "MultiPLX: Automatic Grouping and Evaluation of PCR Primers", Bioinformatics, 21(8), 2005, 1701-1702.
Kazakov, V.I. et al., "Extracellular DNA in the Blood of Pregnant Women", Tsitologia, vol. 37, No. 3, 1995, 1-8.
Kijak, G. et al., "Discrepant Results in the Interpretation of HIV-1 Drug-Resistance Genotypic Data Among Widely Used Algorithms", HIV Medicine, 4, 2003, 72-78.
Kinde, I. et al., "Detection and quantification of rare mutations with massively parallel sequencing", PNAS, vol. 108, No. 23, Jun. 7, 2011, 9530-9535.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.
Kivioja, T. et al., "Counting absolute numbers of molecules using unique molecular identifiers", Nature Methods, Advance Online Publication, Nov. 20, 2011, 1-5.
Konfortov, Bernard A. et al., "An Efficient Method for Multi-Locus Molecular Haplotyping", Nucleic Acids Research, 35(1), e6, 2007, 8 pgs.
Krjutskov, K. et al., "Development of a single tube 640-plex genotyping method for detection of nucleic acid variations on microarrays", Nucleic Acids Research, vol. 36, No. 12, May 23, 2008, 7 pages.
Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.
Lambert-Messerlian, G. et al., "Adjustment of Serum Markers in First Trimester Screening", Journal of Medical Screening, 16 (2), 2009, 102-103.
Lathi, Ruth B. et al., "Informatics Enhanced SNP Microarray Analysis of 30 Miscarriage Samples Compared to Routine Cytogenetics", PLoS ONE, 7(3), 2012, 5 pgs.

Leary, Rebecca J et al., "Detection of Chromosomal Alterations in the Circulation of Cancer Patients with Whole-Genome Sequencing", Science Translational Medicine, 4, 162, 2012, 12.
Li, B., "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.
Li, Y. et al., "Non-Invasive Prenatal Diagnosis Using Cell-Free Fetal DNA in Maternal Plasma from PGD Pregnancies", Reproductive BioMedicine Online, 19 (5), 2009, 714-720.
Li, Ying et al., "Size Separation of Circulatory DNA in Maternal Plasma Permits Ready Detection of Fetal DNA Polymorphisms", Clinical Chemistry, 50, 6, 2004, 1002-1011.
Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.
Liao, J. et al., "An Alternative Linker-Mediated Polymerase Chain Reaction Method Using a Dideoxynucleotide to Reduce Amplification Background", Analytical Biochemistry 253, 137-139 (1997).
Liew, Michael et al., "Genotyping of Single-Nucleotide Polymorphisms", Clinical Chemistry, 50(7), 2004, 1156-1164.
Lindroos, Katatina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.
Lo, et al., "Digital PCR for the Molecular Detection of Fetal Chromosomal Aneuploidy", PNAS, vol. 104, No. 32, Aug. 7, 2007, 13116-13121.
Lo, et al., "Fetal Nucleic Acids in Maternal Blood: the Promises", Clin. Chem. Lab. Med., 50(6), 2012, 995-998.
Lo, et al., "Free Fetal DNA in Maternal Circulation", JAMA, 292(23), (Letters to the Editor), 2004, 2835-2836.
Lo, , "Non-Invasive Prenatal Diagnosis by Massively parallel Sequencing of Maternal Plasma DNA", Open Biol 2: 120086, 2012, 1-5.
Lo, et al., "Prenatal Sex Determination by DNA Amplification from Maternal Peripheral Blood", The Lancet,2, 8676, 1989, 1363-1365.
Lo, et al., "Rapid Clearance of Fetal DNA from Maternal Plasma", Am. J. Hum. Genet., 64, 1999, 218-224.
Lo, et al., "Strategies for the Detection of Autosomal Fetal DNA Sequence from Maternal Peripheral Blood", Annals New York Academy of Sciences,731, 1994, 204-213.
Lo, et al., "Two-way cell traffic between mother and fetus: biologic and clinical implications", Blood, 88(11), Dec. 1, 1996, 4390-4395.
Lo, Y.M. Dennis , "Fetal Nucleic Acids in Maternal Plasma: Toward the Development of Noninvasive Prenatal Diagnosis of Fetal Chromosomal Aneuploidies", Ann. N. Y. Acad. Sci., 1137, 2008, 140-143.
Lo, Y.M. Dennis et al., "Maternal Plasma DNA Sequencing Reveals the Genome-Wide Genetic and Mutational Profile of the Fetus", Science Translational Medicine, , 2 (61), 2010, 13.
Lo, Y.M. Dennis et al., "Plasma placental RNA allelic ratio permits noninvasive prenatal chromosomal aneuploidy detection", Nature Medicine, 13 (2), 2007, 218-223.
Lo, Y.M. Dennis et al., "Presence of Fetal DNA in Maternal Plasma and Serum", The Lancet, 350, 1997, 485-487.
Lo, Y.M. Dennis et al., "Quantitative Analysis of Fetal DNA in Maternal Plasma and Serum: Implications for Noninvasive Prenatal Diagnosis", Am. J. Hum. Genet., 62, 1998, 768-775.
Lo, Y-M.D et al., "Detection of Single-Copy Fetal DNA Sequence from Maternal Blood", The Lancet, 335, 1990, 1463-1464.
Lo, Y-M.D et al., "Prenatal Determination of Fetal Rhesus D Status by DNA Amplification of Peripheral Blood of Rhesus-Negative Mothers", Annals New York Academy of Sciences, 731, 1994, 229-236.
Lo, Y-M.D. et al., "Detection of Fetal RhD Sequence from Peripheral Blood of Sensitized RhD-Negative Pregnant Women", British Journal of Haematology, 87, 1994, 658-660.

(56) References Cited

OTHER PUBLICATIONS

Lo, Y-M.D. et al., "Prenatal Determination of Fetal RhD Status by Analysis of Peripheral Blood of Rhesus Negative Mothers", The Lancet, 341, 1993, 1147-1148.

Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.

Maniatis, T. et al., "In: Molecular Cloning: A Laboratory Manual", Cold Spring Harbor Laboratory, New York, Thirteenth Printing, 1986, 458-459.

Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.

Markoulatos, P. et al., "Multiplex Polymerase Chain Reaction: A Practical Approach", Journal of Clinical Laboratory Analysis, vol. 16, 2002, 47-51.

May, Robert M., "How Many Species Are There on Earth?", Science, 241, Sep. 16, 1988, 1441-1449.

McCloskey, M. L. et al., "Encoding PCR Products with Batchstamps and Barcodes", Biochem Genet., vol. 45, Oct. 23, 2007, 761-767.

McCray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.

Mennuti, M. et al., "Is It Time to Sound an Alarm About False-Positive Cell-Free DNA Testing for Fetal Aneuploidy?", American Journal of Obstetrics, 2013, 5 pgs.

Merriam-Webster, "Medical Definition of Stimulant", http://www.merriam-webster.com/medical/stimulant, Mar. 14, 2016, 7 pages.

Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.

Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.

Miller, Robert R., "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.

Miner, B. E. et al., "Molecular barcodes detect redundancy and contamination in hairpin-bisulfite PCR", Nucleic Acids Research, vol. 32, No. 17, Sep. 30, 2004, 1-4.

Morand, et al., "Hesperidin contributes to the vascular protective effects of orange juice: a randomized crossover study in healthy volunteers", Am J Clin Nutr. Jan. 2011;93(1 ):73-80. Epub Nov. 10, 2011.

Munne, S. et al., "Chromosome abnormalities in human embryos", Human Reproduction update, 4 (6), 842-855.

Munne, S. et al., "Chromosome Abnormalities in Human Embryos", Textbook of Assisted Reproductive Techniques, 2004, pp. 355-377.

Murtaza, M. et al., "Non-Invasive Analysis of Acquired Resistance to Cancer Therapy by Sequencing of Plasma DNA", Nature (doi:10.1038/nature12065), 2013, 6 pgs.

Muse, Spencer V. , "Examining rates and patterns of nucleotide substitution in plants", Plant Molecular Biology 42: 25-43, 2000.

Myers, Chad L. et al., "Accurate Detection of Aneuploidies in Array CGH and Gene Expression Microarray Data", Bioinformatics, 20(18), 2004, 3533-3543.

Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.

Nicolaides, K. et al., "Noninvasive Prenatal Testing for Fetal Trisomies in a Routinely Screened First-Trimester Population", American Journal of Obstetrics (article in press), 207, 2012, 1.e1-1.e6.

Nicolaides, K.H et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.

Nicolaides, Kypros H. et al., "Prenatal Detection of Fetal Triploidy from Cell-Free DNA Testing in Maternal Blood", Fetal Diagnosis and Therapy, 2013, 1-6.

Nygren, et al., "Quantification of Fetal DNA by Use of Methylation-Based DNA Discrimination", Clinical Chemistry 56:10 1627-1635 (2010).

Ogino, S. et al., "Bayesian Analysis and Risk Assessment in Genetic Counseling and Testing", Journal of Molecular Diagnostics, 6 (1), 2004, 9 pgs.

O'Malley, R. et al., "An adapter ligation-mediated PCR method for high-throughput mapping of T-DNA inserts in the *Arabidopsis* genome", Nat. Protoc., 2, 2007, 2910-2917.

Orozco A.F., et al., "Placental Release of Distinct DNA-Associated Micro-Particles into Maternal Circulation: Reflective of Gestation Time and Preeclampsia", Placenta,30, 2009, 891-897.

Ozawa, Makiko et al., "Two Families with Fukuyama Congenital Muscular Dystrophy that Underwent in Utero Diagnosis Based on Polymorphism Analysis", Clinical Muscular Dystrophy: Research in Immunology and Genetic Counseling—FY 1994 Research Report, (including copy of text in Japanese), 1994, 8.

Paez, Guillermo J. et al., "Genome coverage and sequence fidelity of φ29 polymerase-based multiple strand displacement whole genome amplification", Nucleic Acids Research, 32(9), 2004, 1-11.

Page, S. L. et al., "Chromosome Choreography: The Meiotic Ballet", Science, 301, 2003, 785-789.

Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.

Palomaki, Glenn E. et al., "DNA Sequencing of Maternal Plasma to Detect Down Syndrome: An International Clinical Validation Study", Genetics in Medicine (pre-print version), 13, 2011, 8 pgs.

Papageorgiou, Elisavet A. et al., "Fetal-Specific DNA Methylation Ratio Permits Noninvasive Prenatal Diagnosis of Trisomy 21", Nature Medicine (advance online publication),17, 2011, 5 pgs.

Pathak, A. et al., "Circulating Cell-Free DNA in Plasma/Serum of Lung Cancer Patients as a Potential Screening and Prognostic Tool", Clinical Chemistry, 52, 2006, 1833-1842.

PCT/US2006/045281, "International Preliminary Report on Patentability", dated May 27, 2008, 1 pg.

PCT/US2006/045281, "International Search Report and Written Opinion", dated Sep. 28, 2007, 7 pgs.

PCT/US2008/003547, "International Search Report", dated Apr. 15, 2009, 5 pgs.

PCT/US2009/034506, "International Search Report", dated Jul. 8, 2009, 2 pgs.

PCT/US2009/045335, "International Search Report", dated Jul. 27, 2009, 1 pg.

PCT/US2009/052730, "International Search Report", dated Sep. 28, 2009, 1 pg.

PCT/US2010/050824, "International Search Report", dated Nov. 15, 2010, 2 pgs.

PCT/US2011/037018, "International Search Report", dated Sep. 27, 2011, 2 pgs.

PCT/US2011/061506, "International Search Report", dated Mar. 16, 2012, 1 pgs.

PCT/US2011/066938, "International Search Report", dated Jun. 20, 2012, 1 pg.

PCT/US2012066339, "International Search Report", dated Mar. 5, 2013, 1 pg.

PCT/US2013/028378, "International Search Report and Written Opinion", dated May 28, 2013, 11 pgs.

PCT/US2013/57924, "International Search Report and Written Opinion", dated Feb. 18, 2014, 8 pgs.

(56) References Cited

OTHER PUBLICATIONS

PCT/US2014/051926, "International Search Report and Written Opinion", dated Dec. 9, 2014, 3 pgs.
Pearson, K., "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Pena, Sergio D.J et al., "Paternity Testing in the DNA Era", Trends in Genetics, 10, 6, 1994, 204-209.
Perkel, Jeffrey M. , "Overcoming the Challenges of Multiplex PCR", Biocompare Editorial Article, NULL, 2012, 1-5.
Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, David P. et al., "Noninvasive Prenatal Diagnosis of a Fetal Microdeletion Syndrome", New England Journal of Medicine, 365(19), 2011, 1847-1848.
Pfaffl, Michael W., "Relative Expression Software Tool (REST ©) for Group-Wise Comparison and Statistical Analysis of Relative Expression Results in real-Time PCR", Nucleic Acids Research, 30(9), 2002, 10 pgs.
Phillips, C. et al., "Resolving Relationship Tests that Show Ambiguous STR Results Using Autosomal SNPs as Supplementary Markers", Forensic Science International: Genetics 2, 2008, 198-204.
Podder, Mohua et al., "Robust SN P genotyping by multiplex PCR and arrayed primer", BMC Medical Genomics,1(5), 2008, 1-15.
Porreca, Gregory J et al., "Multiplex Amplification of Large Sets of Human Exons", Nature Methods, 4, (advance online publication), 2007, 6.
Price, T.S. et al., ""SW-ARRAY: a dynamic programming solution for the identification of copy-number changes in genomic DNA using array comparative genome hybridization data",", Nucleic Acids Research, vol. 33, No. 11, Jun. 16, 2005, 3455-3464.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, Matthew et al., "Origins and rates of aneuploidy inhuman blastomeres", Fertility and Sterility, vol. 97, No. 2, Feb. 2012, 395-401.
Rabinowitz, Matthew. et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.
Ragoussis, J. , "Genotyping Technologies for Genetic Research", Annual Review of Genomics and Human Genetics, vol. 10 (1), Sep. 1, 2009, 117-133.
Rahmann, Sven et al., "Mean and variance of the Gibbs free energy of oligonucleotides in the nearest neighbor model under varying conditions", Bioinformatics, 20(17), 2004, 2928-2933.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.
Rechitsky, Svetlana et al., "Preimplantation Genetic Diagnosis with HLA Matching", Reproductive Bio Medicine Online, 9, 2, 2004, 210-221.
Renwick, P. et al., "Proof of Principle and First Cases Using Preimplantation Genetic Haplotyping—A Paradigm Shift for Embryo Diagnosis", Reproductive BioMedicine Online, 13 (1), 2006, 110-119.
Ricciotti, Hope, "Eating by Trimester", Online]. Retrieved from Internet:<http://www.youandyourfamily.com/article.php?story=Eating+by+Trimester>, 2014, 3.
Riley, D. E., "DNA Testing: An Introduction for Non-Scientists an Illustrated Explanation", Scientific Testimony: An Online Journal, http://www.scientific.org/tutorials/articles/riley/riley.html, Apr. 6, 2005, 22 pages.
Roper, Stephen M. et al., "Forensic Aspects of DNA-Based Human Identity Testing", Journal of Forensic Nursing, 4, 2008, 150-156.
Roux, K., "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Russell, L. M., "X Chromosome Loss and Ageing", Cytogenetic and Genome Res., 116, 2007, 181-185.
Ryan, et al., "The importance of phase information for human genomics", Nature Reviews Genetics, voi. 12, No. 3, Mar. 1, 2011.
Ryan, A. et al., "Informatics-Based, Highly Accurate, Noninvasive Prenatal Paternity Testing", Genetics in Medicine (advance online publication), 2012, 5 pgs.
Rychlik, et al., "Optimization of the annealing temperature for DNA amplification in vitro", Nucleic Acids Research, 18(21), 1990, 6409-6412.
Sahota, A., "Evaluation of Seven PCR-Based Assays for the Analysis of Microchimerism", Clinical Biochemistry, vol. 31, No. 8., 1998, 641-645.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Sander, Chris, "Genetic Medicine and the Future of Health Care", Science, 287(5460), 2000, 1977-1978.
Santalucia, J. et al., "The Thermodynamics of DNA Structural Motifs", Annu. Rev. Biophys. Biomol. Struct., 33, 2004, 415-440.
Santalucia, John J.R et al., "Improved Nearest-Neighbor Parameters for Predicting DNA Duplex Stability", Biochemistry, 35, 1996, 3555-3562.
Sasabe, Yutaka, "Genetic Diagnosis of Gametes and Embryos Resulting from ART", Japanese Journal of Fertility and Sterility, 2001, vol. 46, No. 1, p. 43-46.
Schmitt, M. W. et al., "Detection of ultra-rare mutations by next-generation sequencing", PNAS, vol. 109, No. 36, Sep. 4, 2012, 14508-14513.
Schoumans, J et al., "Detection of chromosomal imbalances in children with idiopathic mental retardation by array based comparative genomic hybridisation (array-CGH)", JMed Genet, 42, 2005, 699-705.
Sebat, Jonathan et al., "Strong Association of De Novo Copy Number Mutations with Autism", Science, 316, 2007, 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Sermon, Karen et al., "Preimplantation genetic diagnosis", The Lancet, Lancet Limited. 363(9421), 2000, 1633-1641.
Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.
Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, 2004, 241-248.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.
Shen, Zhiyong, "MPprimer: a program for reliable multiplex PCR primer design", BMC Bioinformatics 2010, 11:143, 1-7.
Sherlock, J et al., "Assessment of Diagnostic Quantitative Fluorescent Multiplex Polymerase Chain Reaction Assays Performed on Single Cells", Annals of Human Genetics,62, 1, 1998, 9-23.

(56) References Cited

OTHER PUBLICATIONS

Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.
Simpson, J. et al., "Fetal Cells in Maternal Blood: Overview and Historical Perspective", Annals New York Academy of Sciences, 731, 1994, 1-8.
Sint, Daniela et al., "Advances in Multiplex PCR: Balancing Primer Efficiencies and Improving Detection Success", Methods in Ecology and Evolution, 3, 2012, 898-905.
Slater, Howard et al., "High-Resolution Identification of Chromosomal Abnormalities Using Oligonucleotide Arrays Containing 116,204 SNPs", Am. J. Hum. Genet., 77, 5, 2005, 709-726.
Snijders, Antoine et al., "Assembly of Microarrays for Genome-Wide Measurement of DNA Copy Number", Nature Genetic, 29, 2001, 263-264.
Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.
Sparks, Andrew B. et al., "Selective Analysis of Cell-Free DNA in Maternal Blood for Evaluation of Fetal Trisomy", Prenatal Diagnosis, 32, 2012, 1-7.
Spiro, Alexander et al., "A Bead-Based Method for Multiplexed Identification and Quantitation of DNA Sequences Using Flow Cytometry", Applied and Environmental Microbiology, 66, 10, 2000, 4258-4265.
Spits, C et al., "Optimization and Evaluation of Single-Cell Whole Genome Multiple Displacement Amplification", Human Mutation, 27(5), 496-503, 2006.
Srinivasan, et al., "Noninvasive Detection of Fetal Subchromosome Abnormalities via Deep Sequencing of Maternal Plasma", The American Journal of Human Genetics 92, 167-176, Feb. 7, 2013.
Stephens, Mathews. et al., "A Comparison of Bayesian Methods for Haplotype Reconstruction from Population Genotype Data", Am. J. Hum. Genet.,73, 2003, 1162-1169.
Stevens, Robert et al., "Ontology-Based Knowledge Representation for Bioinformatics", Briefings in Bioinformatics, 1, 4, 2000, 398-414.
Steyerberg, E.W et al., "Application of Shrinkage Techniques in Logistic Regression Analysis: A Case Study", Statistica Neerlandica, 55(1), 2001, 76-88.
Strom, C. et al., "Three births after preimplantation genetic diagnosis for cystic fibrosis with sequential first and second polar body analysis", American Journal of Obstetrics and Gynecology, 178 (6), 1998, 1298-1306.
Strom, Charles M. et al., "Neonatal Outcome of Preimplantation Genetic Diagnosis by Polar Body Removal: The First 109 Infants", Pediatrics, 106( 4), 2000, 650-653.
Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.
Su, S.Y. et al., ""Inferring combined CNV/SNP haplotypes from genotype data"", Bioinformatics, vol. 26, No. 11,1, Jun. 1, 2010, 1437-1445.
Sun, Guihua et al., "SNPs in human miRNA genes affect biogenesis and function", RNA, 15(9), 2009, 1640-1651.
Sweet-Kind Singer, J. A. et al., "Log-penalized linear regression", IEEE International Symposium on Information Theory, 2003. Proceedings, 2003, 286.
Taliun, D. et al., "Efficient haplotype block recognition of very long and dense genetic sequences", BMC Bioinformatics, vol. 15 (10), 2014, 1-18.
Tamura, et al., "Sibling Incest and formulation of paternity probability: case report", Legal Medicine, 2000, vol. 2, p. 189-196.
Tang, et al., Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.
Tang, N. et al., "Detection of Fetal-Derived Paternally Inherited X-Chromosome Polymorphisms in Maternal Plasma", Clinical Chemistry, 45 (11), 1999, 2033-2035.
Ten Bosch, J., "Keeping Up With the Next Generation Massively Parallel Sequencing in Clinical Diagnostics", Journal of Molecular Diagnostics, vol. 10, No. 6, 2008, 484-492.
Thomas, M.R et al., "The Time of Appearance and Disappearance of Fetal DNA from the Maternal Circulation", Prenatal Diagnosis, 15, 1995, 641-646.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.
Tong, Yu K. et al., "Noninvasive Prenatal Detection of Trisomy 21 by Epigenetic-Genetic Chromosome-Dosage Approach", Clinical Chemistry, 56(1), 2010, 90-98.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.
Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.
Tu, J. et al., "Pair-barcode high-throughput sequencing for large-scale multiplexed sample analysis", BMC Genomics, vol. 13, No. 43, Jan. 25, 2012, 1-9.
Turner, E. et al., "Massively Parallel Exon Capture and Library-Free Resequencing Across 16 Genomes", Nature Methods, 6 (5), 2009, 315-316.
Vallone, Peter, "AutoDimer: a Screening Tool for Primer-Dimer and Hairpin Structures", Bio Techniques, 37, 2004, 226-231.
Varley, Katherine Elena et al., "Nested Patch PCR Enables Highly Multiplexed Mutation Discovery in Candidate Genes", Genome Res., 18(11), 2008, 1844-1850.
Verlinsky, Y. et al., "Over a Decade of Experience with Preimplantation Genetic Diagnosis", Fertility and Sterility, 82 (2), 2004, 302-303.
Wagner, Jasenka et al., "Non-Invasive Prenatal Paternity Testing from Maternal Blood", Int. J. Legal Med., 123, 2009, 75-79.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.
Watkins, N. et al., "Thermodynamic contributions of single internal rA •dA, rC • dC, rG • dG and rU • dT mismatches in RNA/DNA duplexes", Nucleic Acids Research, 9 (5), , 2010, 1894-1902.
Wells, D., "Microarray for Analysis and Diagnosis of Human Embryos", 12th International Congress on Prenatal Diagnosis and Therapy, Budapest, Hungary, 2004, 9-17.
Wells, Dagan, "Advances in Preimplantation Genetic Diagnosis", European Journal of Obstetrics and Gynecology and Reproductive Biology, 115S, 2004, S97-S101.
Wells, Dagan, "Detailed Chromosomal and Molecular Genetic Analysis of Single Cells by Whole Genome Amplification and Comparative Genomic Hybridisation", Nucleic Acids Research, 27, 4, 1999, 1214-1218.
Wen, Daxing et al., "Universal Multiples PCR: A Novel Method of Simultaneous Amplification of Multiple DNA Fragments", Plant Methods, 8(32), Null, 2012, 1-9.
Wikipedia, "Maximum a posteriori estimation", https://en.wikipedia.org/w/index.php?title=Maximum_a_posteriori_estimation&oldid=26878808, [retrieved on Aug. 1, 2017], Oct. 30, 2005, 2 pages.
Wilton, et al., "Birth of a Healthy Infant After Preimplantation Confirmation of Euploidy by Comparative Genomic Hybridization", N. Engl. J. Med., 345(21), 2001, 1537-1541.

(56) References Cited

OTHER PUBLICATIONS

Wilton, L., "Preimplantation Genetic Diagnosis and Chromosome Analysis of Blastomeres Using Comparative Genomic Hybridization", Human Reproduction Update, 11 (1), 2005, 33-41.
Wright, C. et al., "The use of cell-free fetal nucleic acids in maternal blood for non-invasive prenatal diagnosis", Human Reproduction Update, vol. 15, No. 1, 2009, 139-151.
Wright, C. F. et al., "Cell-free fetal DNA and RNA in maternal blood: implications for safer antenatal testing", BMJ, vol. 39, Jul. 18, 2009, 161-165.
Wu, Y. Y. et al., "Rapid and/or high-throughput genotyping for human red blood cell, platelet and leukocyte antigens, and forensic applications", Clinica Chimica Acta, vol. 363, 2006, 165-176.
Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.
Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.
Yeh, Iwei et al., "Knowledge Acquisition, Consistency Checking and Concurrency Control for Gene Ontology (GO)", Bioinformatics, 19, 2, 2003, 241-248.
You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.
Zhang, Rui et al., "Quantifying RNA allelic ratios by microfluidic multiplex PCR and sequencing", Nature Methods, 11(1), 2014, 51-56.
Zhao, Xiaojun. et al., "An Integrated View of Copy Number and Allelic Alterations in the Cancer Genome Using Single Nucleotide Polymorphism Arrays", Cancer Research,64, 2004, 3060-3071.
Zhou, W. et al., "Counting Alleles Reveals a Connection Between Chromosome 18q Loss and Vascular Invasion", Nature Biotechnology, 19, 2001, 78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.
Alaeddini, R. et al., "Forensic implications of genetic analyses from degraded DNA—A review", Forensic Science International: Genetics, vol. 4, 2010, 148-157.
Alberts, B. et al., "Chapter 20: Germ Cells and Fertilization", Molecular Biology of the Cell, Fourth Edition, 2002, 1127-1156.
Alberts, B. et al., "Chapter 4: DNA and Chromosomes", Molecular Biology of the Cell, Fourth Edition, 2002, 191-234.
Antonarakis, S. E. et al., "Chromosome 21 and Down Syndrome: From Genomics to Pathophysiology", Nature Reviews Genetics, vol. 5, Oct. 2004, 725-738.
Beroud, C. et al., "Prenatal diagnosis of spinal muscular atrophy by genetic analysis of circulating fetal cells", The Lancet, vol. 361, Mar. 22, 2003, 1013-1014.
Bianchi, D. W. , "Circulating Fetal DNA: Its Origin and Diagnostic Potential—A Review", Placenta, vol. 25, Supplemental A, May 2004, S93-S101.
Bianchi, D. W. , "Review: Fetal Cells in the Maternal Circulation: Feasibility for Prenatal Diagnosis", British Journal of Haematology, vol. 105, 1999, 574-583.
Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.
Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.
Coombes, R. C. , "Abstract P4-01-02: Early detection of residual breast cancer through a robust, scalable and personalized analysis of circulating tumour DNA (ctDNA) antedates overt metastatic recurrence", Cancer Research, vol. 79, No. 4 Supplement, Feb. 15, 2019.

Deutsch, S. et al., "Detection of aneuploidies by paralogous sequence quantification", J Med Genet, vol. 41, 2004, 908-915.
Dietmaier, W. et al., "Multiple Mutation Analyses in Single Tumor Cells with Improved Whole Genome Amplification", American Journal of Pathology, vol. 154, No. 1, Jan. 1999, 83-95.
Everitt, B. S. , "Medical Statistics From A to Z", 2003, 3 pages.
Hartwell, L. H. et al., "Chapter 11: The Direct Detection of Genotype Distinguishes Individual Genomes", Genetics: From Genes to Genomes, Second Edition, 2004, 371-414.
Hartwell, L. H. et al., "Chapter 13: Chromosomal Rearrangements and Changes in Chromosome Number Reshape Eukaryotic Genomes", Genetics: From Genes to Genomes, Second Edition, 2004, 441-486.
Hattori, M. et al., "The DNA sequence of human chromosome 21", Nature, vol. 405, May 18, 2000, 311-319.
Hornak, M. et al., "Aneuploidy Detection in Pigs Using Comparative Genomic Hybridization: From the Oocytes to Blastocysts", PLoS ONE, vol. 7, No. 1, Jan. 2012, 6 pages.
Illumina, , "Patent Owner Illumina's Preliminary Response to Petition", Oct. 17, 2018, 75 pgs.
Illumina, "Petition for Inter Partes Review of U.S. Pat. No. 8,682,592", Jun. 13, 2019, 91 pages.
Illumina, , "Plaintiff/Counterclaim Defendant Illumina, Inc.'s Amended Patent L.R. 3-3 Preliminary Invalidity Contentions for U.S. Pat. No. 8,682,592", Oct. 30, 2018, 22 pages.
Illumina, , "Plaintiff/Counterclaim-Defendant Illumina, Inc.'s Patent L.R. 3-3 Contentions for U.S. Patent Preliminary Invalidity Contentions for U.S. Pat. No. 8,682,592", Oct. 9, 2018, 81 pages.
Illumina, Inc., , "Declaration of David Peters, Ph.D. in Support of Petition for Inter Partes Review of U.S. Pat. No. 8,682,592", Jun. 13, 2019, 136 pages.
*Illumina, Inc. v. Natera, Inc.*, , "Order Re: Claim Construction", Jan. 30, 2019, 16 pgs.
Kamat, A. A. et al., "Quantification of total plasma cell-free DNA in ovarian cancer using real-time PCR", Ann N Y Acad Sci., vol. 1075, Sep. 2006, 230-234.
Lo, Y. , "Noninvasive prenatal detection of fetal chromosomal aneuploidies by maternal plasma nucleic acid analysis: a review of the current state of the art", BJOB An International Journal of Obstetrics and Gynaecology, vol. 116, 2009, 152-157.
Lu, I. et al., "Establishment of a system based on universal multiplex-PCR for screening genetically modified crops", Anal. Bioanal. Chem, vol. 396, Oct. 24, 2009, 2055-2064.
Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.
Magbanua, M. J. et al., "Abstract PD2-01: Personalized serial circulating tumor DNA (ctDNA) analysis in high-risk early stage breast cancer patients to monitor and predict response to neoadjuvant therapy and outcome in the I-SPY 2 Trial", Cancer Research, vol. 79, No. 4 Supplement, Feb. 15, 2019.
Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.
McDonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.
Minkoff, E. et al., "Stem Cells, Cell Division, and Cancer", Biology Today Third Edition, Chapter 12, 2004, 10 pages.
Munne, S. et al., "Improved implantation after preimplantation genetic diagnosis of aneuploidy", Reproductive BioMedicine Online, vol. 7., No. 1., May 15, 2003, 91-97.
Natera, Inc., , "Defendant Natera, Inc.'s Invalidity Contentions Under Patent L.R. 3-3; Document Production Accompanying Invalidity Contentions Under Patent L.R. 3-4", Aug. 20, 2018, 17 pages.
Natera, Inc., , "Exhibit 8 EHRICH Invalidity Chart", Aug. 20, 2018, 16 pages.
Natera, Inc., , "Natera Inc.'s First Amended Answer, Affirmative Defenses and Counterclaims", Aug. 16, 2018, 28 pages.
Natera, Inc., , "Natera, Inc.'s Supplemental Objections and Response to Plaintiff Illumina, Inc.'s Interrogatory No. 8", Mar. 20, 2019, 29 pages.

(56) References Cited

OTHER PUBLICATIONS

Natera, Inc., , "Petitioner Reply Per Board Order of Nov. 2, 2018 (Paper No. 10)", Nov. 9, 2018, 8 pgs.
Ng, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.
Nguyen-Dumont, T. , "A high-plex PCR approach for massively parallel sequencing", BioTechniques, vol. 55, No. 2, Aug. 2013, 69-74.
Papadopoulou, E. et al., "Cell-Free DNA and RNA in Plasma as a New Molecular Marker for Prostate Cancer", Oncology Research, vol. 14, 2004, 439-445.
Pastinen, T. et al., "Minisequencing: A Specific Tool for DNA Analysis and Diagnostics on Oligonucleotide Arrays", Genome Research, vol. 7, 1997, 606-614.
Peters, D. , "List of Materials Considered by David Peters, Ph.D.", Jun. 13, 2019, 2 pages.
Reinert, T. et al., "Analysis of circulating tumour DNA to monitor disease burden following colorectal cancer surgery", Gut, vol. 65, 2016, 625-634.
Riva, F. , "Patient-Specific Circulating Tumor DNA Detection during Neoadjuvant Chemotherapy in Triple-Negative Breast Cancer", Clinical Chemistry, vol. 63, No. 3, 2017, 691-699.
Sham, P. et al., "DNA Pooling: A Tool for Large-Scale Association Studies", Nature Reviews Genetics, vol. 3, Nov. 2002, 862-871.
Shen, R. et al., "High-throughput SNP genotyping on universal bead arrays", Mutation Research, vol. 573, Feb. 11, 2005, 70-82.
The International HapMap Consort, , "The International HapMap Project", Nature, vol. 426, Dec. 18, 2003, 789-796.
Tiersch, T. R. et al., "Reference Standards for Flow Cytometry and Application in Comparative Studies of Nuclear DNA Content", Cytometry, vol. 10, Mar. 21, 1989, 706-710.
Wang, D. G. et al., "Large-Scale Identification, Mapping, and Genotyping of Single-Nucleotide Polymorphisms in the Human Genome", Science, vol. 280, May 15, 1998, 1077-1082.
Wang, T.L. et al., "Digital karyotyping", PNAS, vol. 99, No. 25, Dec. 10, 2002, 16156-16161.
Weiss, C. A. , "Chapter 8: Confidence Intervals for One Population Mean", Introductory Statistics, Sixth Edition, 2002, 340-381.
Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.
Zhang, L. et al., "Whole genome amplification from a single cell: Implications for genetic analysis", Proc. Nat'l. Acad. Sci. USA, vol. 89, Jul. 1992, 5847-5851.
Zimmermann, B. , "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.
Allan, J. et al., "Micrococcal Nuclease Does Not Substantially Bias Nucleosome Mapping", Journal of Molecular Biology, vol. 417, Jan. 30, 2012, 152-164.
Dawson, S.J. et al., "Analysis of Circulating Tumor DNA to Monitor Metastatic Breast Cancer", The New England Journal of Medicine, vol. 368, No. 13, Mar. 28, 20136, 1199-1209.

Deng, S. et al., "TNER: A Novel Background Error Suppression Method for Mutation Detection in Circulating Tumor DNA", bioRxiv, http://dx.doi.org/10.1101/214379, Nov. 5, 2017, 12 pgs.
Diehl, F. et al., "Circulating mutant DNA to assess tumor dynamics", Nature Medicine, vol. 14, No. 9, Jul. 31, 2008, 985-990.
Forshew, T. et al., "Supplementary Materials for Noninvasive Identification and Monitoring of Cancer Mutations by Targeted Deep Sequencing of Plasma DNA", Sci. Transl. Med, vol. 4, May 30, 2012, 20 pgs.
Gielis, E. M. et al., "Plasma donor-derived cell-free DNA kinetics after kidney transplantation using a single tube multiplex PCR assay", PLOS One, vol. 13, No. 12, e0208207, Dec. 6, 2018, 16 pgs.
Han, S-W et al., "Predictive and Prognostic Impact of Epidermal Growth Factor Receptor Mutation in Non-Small-Cell Lung Cancer Patients Treated With Gefitinib", Journal of Clinical Oncology, vol. 23, No. 11, Apr. 10, 2005, 2493-2501.
Imielinski, M. et al., "Mapping the Hallmarks of Lung Adenocarcinoma with Massively Parallel Sequencing", Cell, vol. 150, Sep. 14, 2012, 1107-1120.
Lindberg, J. et al., "Exome Sequencing of Prostate Cancer Supports the Hypothesis of Independent Tumour Origins", European Urology, vol. 63, 2013, 347-353.
Mertes, F. et al., "Targeted enrichment of genomic DNA regions for next-generation sequencing", Briefings in Functional Genomics, vol. 10, No. 6, Nov. 26, 2011, 374-386.
NCBI, , "dbSNP record for rs1294331", Retrieved from the Internet: <URL: www.ncbi.nlm.nih.gov/snp/?term=rs 1294331 >, 2019, 2 pgs.
NCBI, , "dbSNP record for rs1872575", Retrieved from the Internet: <URL: www.ncbi.nlm.nih.gov/snp/?term=rs1872575, 2019, 2 pgs.
NCBI, , "dbSNP record for rs2362450", Retrieved from the Internet: <URL: www.ncbi.nlm.nih.gov/snp/?term=rs2362450>, 2019, 1 pg.
NCBI, ,"dbSNP record for rs2384571", Retrieved from the Internet: <URL: www.ncbi.nlm.nih.gov/snp/?term=rs2384571>, 2019, 2 pgs.
NCBI, , "dbSNP record for rs2498982", Retrieved from the Internet: <URL: www.ncbi.nlm.nih.gov/snp/?term=rs2498982>, 2019, 3 pgs.
NCBI, , "dbSNP record for rs3731877", Retrieved from the Internet: <URL: www.ncbi.nlm.nih.gov/snp/?term=rs3731877>, 2019, 2 pgs.
Newman, A. M. et al., "Integrated digital error suppression for improved detection of circulating tumor DNA", Nature Biotechnology, vol. 34, No. 5, May 2016, 547-555.
Shi, H. et al., "Melanoma whole-exome sequencing identifies V600E B-RAF amplification-mediated acquired B-RAF inhibitor resistance", Nature Communications, vol. 3, No. 724, Mar. 6, 2012, 8 pages.
Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.
Widlak, P. et al., "Cleavage Preferences of the Apoptotic Endonuclease DFF 40 (Caspase-activated DNase or Nuclease) on Naked DNA and Chromatin Substrates", The Journal of Biological Chemistry, vol. 275, No. 11, Mar. 17, 2000, 8228-8232.
Yung, T. K. et al., "Single-Molecule Detection of Epidermal Growth Factor Receptor Mutations in Plasma by Microfluidics Digital PCR in Non-Small Cell Lung Cancer Patients", Clinical Cancer Research, vol. 15, Mar. 10, 2009, 2076-2084.

| Experiment | Sample | Input Genome Copies | Mapped Reads | On-Target Reads | Percent On-Target (of Mapped) | Mean Depth of Read | Mean Error Rate | Paired MIT Families | Paired MIT Family Error Rate | Error Rate Fold Reduction |
|---|---|---|---|---|---|---|---|---|---|---|
| A | 1 | 10,000 | 10,435,870 | 7,649,878 | 73% | 243,690 | 0.15% | 2,655 | 0.0050% | 30 |
| A | 2 | 10,000 | 10,659,412 | 7,790,389 | 73% | 242,581 | 0.15% | 2,735 | 0.0067% | 23 |
| B | 3 | 10,000 | 6,561,397 | 4,631,540 | 71% | 150,944 | 0.26% | 2,926 | 0.0047% | 56 |
| B | 4 | 10,000 | 4,372,076 | 2,982,608 | 68% | 97,817 | 0.26% | 2,642 | 0.0039% | 66 |
| C | 5 | 10,000 | 8,910,419 | 6,247,476 | 70% | 157,546 | 0.23% | 2,994 | 0.0036% | 63 |
| C | 6 | 10,000 | 8,954,199 | 6,590,002 | 74% | 171,377 | 0.26% | 2,527 | 0.0036% | 73 |

FIG. 4

COMPOSITIONS AND METHODS FOR IDENTIFYING NUCLEIC ACID MOLECULES

RELATED APPLICATIONS

This application is a divisional of U.S. Utility application Ser. No. 15/372,279, filed Dec. 7, 2016, now U.S. Pat. No. 10,011,870. The entirety of this application is hereby incorporated herein by reference for the teachings therein.

SEQUENCE LISTING

The instant application contains a Sequence Listing which has been submitted electronically in ASCII format and is hereby incorporated by reference in its entirety. Said ASCII copy, created on Nov. 15, 2017, is named N_018_US_03_SL.txt and is 5,065 bytes in size.

FIELD OF THE INVENTION

The disclosed present disclosures relate generally to methods for analyzing nucleic acids.

BACKGROUND OF THE INVENTION

Next-generation sequencing has greatly increased the throughput of sequencing methods and resulted in new applications for sequencing with important real-world implications, such as improvements in cancer diagnostics and non-invasive prenatal testing for disorders such as Down's Syndrome. There are various technologies for performing next-generation sequencing, each of which is associated with specific types of errors. In addition, these methods share general sources for errors, such as errors that occur during sample preparation.

Sample preparation for next-generation sequencing typically involves numerous amplification steps, each of which generates errors. Amplification reactions, such as PCR, used in sample preparation for high-throughput sequencing can include amplifying the initial nucleic acid in the sample to generate the library to be sequenced, clonally amplifying the library, typically onto a solid support, and additional amplification reactions to add additional information or functionality such as sample identifying barcodes. Errors can be introduced during any of the amplification reactions, for example through the misincorporation of bases by a polymerase used for the amplification. It can be difficult to distinguish these errors introduced during sample prep and errors that occur during a sequencing reaction, from real and informative SNPs, or mutations present in the initial sample, especially when the SNPs or mutations are present at a low frequency. In addition, calling the base at each nucleotide can introduce errors as well, usually caused by a low signal intensity and/or the surrounding nucleic acid sequence.

There are several known methods to identify errors caused by sample preparation. One method is to have greater sequencing depth such that the sample nucleic acid segment is read multiple times from the same molecule, or from different copies of the same nucleic acid molecule. These multiple reads can be aligned and a consensus sequence can be generated. However, SNPs or mutations with low frequency in the population of nucleic acid molecules will appear similar to errors introduced during amplification or base calling. Another method to identify these errors involves tagging nucleic acid molecules such that each nucleic acid molecule incorporates a unique identifier before being sequenced. The sequencing results from identically tagged nucleic acid molecules are pooled and the consensus sequence from these pooled results is more likely to be the true sequence of the nucleic acid from the sample. Amplification errors can be identified if some of the identically tagged nucleic acid molecules have a different sequence.

Despite these prior methods, there is a need to discover advantageous combinations of parameters for methods of tagging nucleic acid molecules that are highly effective and readily manufacturable, especially for analyzing complex samples, including mammalian cDNA or genomic samples such as, for example, circulating DNA samples. Many prior art methods require the generation of large numbers of unique identifiers and may also result in the need for longer unique identifiers. The reaction mixtures in such methods are designed so there is a large excess of unique identifiers relative to sample nucleic acid molecules. In addition to the high cost of making such libraries of unique identifiers, increasing the lengths of the unique identifiers reduces the amount of sample nucleic acid sequence that can be read in the already limited read lengths of most next-generation sequencers. In other prior art disclosures, which sometimes are only prophetic, detailed combinations of parameters are absent, for combinations such as the diversity of identifiers or the diversity of combinations of any two identifiers versus the number of copies of the region of interest, the diversity of identifiers versus the total number of sample nucleic acid molecules, and the total number of identifiers versus the total number of sample nucleic acid molecules. This is especially true for samples that are complex and isolated from nature, such as cDNA or genomic samples, including fragmented genomic samples, such as circulating free DNA in mammalian blood.

There remains a need for a low-cost tagging method, and for identification of combinations of key parameters for tagging complex samples isolated from nature. Such a method would provide benefit, for example, for detecting amplification and base calling errors when used in a high-throughput sequencing workflow, especially in the analysis of complex, clinically-relevant samples.

SUMMARY OF THE INVENTION

The present disclosure provides improved methods and compositions to tag nucleic acid molecules utilizing Molecular Index Tags ("MITs") to identify amplification products arising from individual sample nucleic acids after amplification of a population of sample nucleic acids molecules. Furthermore, provided herein are methods that use the MITs for determining the sequence of sample nucleic acid molecules, identifying errors incurred during sample preparation or base calling, and determining the number of copies of chromosomes or chromosome segments. Additionally, provided herein are compositions that include reaction mixtures of sample nucleic acid molecules and MITs, populations of tagged nucleic acid molecules, libraries of MITs, and kits for generating tagged nucleic acid molecules using MITs. Accordingly, the present disclosure provides methods and compositions for differentiating errors that are introduced during sample preparation and base calling, especially during a high-throughput sequencing workflow, from real differences that are present in nucleic acid molecules in a starting sample.

Accordingly, provided herein in one aspect is a method for sequencing a population of sample nucleic acid molecules, that includes the following: forming a reaction mixture comprising the population of sample nucleic acid molecules and a set of Molecular Index Tags (MITs), wherein the MITs are nucleic acid molecules, wherein the number of different MITs in the set of MITs is between 10 and 1,000, and wherein a ratio of the total number of sample nucleic acid molecules in the population of sample nucleic acid molecules to the diversity of MITs in the set of MITs or the diversity of any two MITs in the set of MITs is at least 500:1, 1,000:1, 10,000:1, or 100,000:1; attaching at least one MIT from the set of MITs to a sample nucleic acid segment of at least 50% of the sample nucleic acid molecules to form a population of tagged nucleic acid molecules, wherein the at least one MIT is located 5' and/or 3' to the sample nucleic acid segment on each tagged nucleic acid molecule and wherein the population of tagged nucleic acid molecules comprise at least one copy of each MIT of the set of MITs; amplifying the population of tagged nucleic acid molecules to create a library of tagged nucleic acid molecules; and determining the sequences of the attached MITs and at least a portion of the sample nucleic acid segments of the tagged nucleic acid molecules in the library of tagged nucleic acid molecules, thereby sequencing the population of sample nucleic acid molecules. The total number of MIT molecules in the reaction mixture is typically greater than the total number of sample nucleic acid molecules in the reaction mixture.

In some embodiments, the method can include identifying the individual sample nucleic acid molecules that gave rise to the tagged nucleic acid molecules using the sequences of the at least one MIT on each tagged nucleic acid molecule. In some embodiments, the method can further include before identifying the individual sample nucleic acid molecules, mapping the determined sequence of at least one of the sample nucleic acid segments to a location in the genome of the source from which the sample is derived and using the mapped genome location along with the sequence of the at least one MIT to identify the individual sample nucleic acid molecule that gave rise to the tagged nucleic acid molecule. Furthermore, in such embodiments a mutation in a nucleic acid segment or an allele of the nucleic acid segment can be identified.

In some embodiments, the sample can be a mammalian sample, such as a human sample, and the sample, for example, can be a blood sample. The diversity of the combination of any 2 MITs in the set of MITs can exceed the total number of sample nucleic acid molecules that span each target locus of a plurality of target loci of a genome of a mammal that is the source of the mammalian sample.

In some embodiments, the MITs can be attached during a ligation reaction. In some embodiments, the tagged nucleic acid molecules can be enriched using hybrid capture. In some embodiments, the enriched tagged nucleic acid molecules can be clonally amplified onto a solid support or a plurality of solid supports before the sequence is determined using high-throughput sequencing.

In some embodiments, the method can include using a sample where at least some of the sample nucleic acids comprise at least one target loci of a plurality of target loci from a chromosome or chromosome segment of interest. In some embodiments, the method can further include using the identified sample nucleic acid molecules to measure a quantity of DNA for each target locus by counting the number of sample nucleic acid molecules that comprise each target locus; and determining, on a computer, the number of copies of the one or more chromosomes or chromosome segments of interest using the quantity of DNA at each target locus in the sample nucleic acid molecules.

In some embodiments, the sample can include circulating cell-free human DNA, including circulating tumor DNA, wherein the diversity of combinations of any 2 MITs in the set of MITs exceeds the total number of circulating cell-free DNA fragments or sample nucleic acid molecules that span a target locus in the human genome.

Provided herein in another aspect is a method for identifying amplification errors from sample preparation for high-throughput sequencing or identifying base-calling errors in a high-throughput sequencing reaction of a population of tagged nucleic acid molecules derived from a sample, that includes the following: forming a reaction mixture comprising the population of sample nucleic acid molecules and a set of Molecular Index Tags (MITs), wherein the MITs are double-stranded nucleic acid molecules, wherein the number of different MITs in the set of MITs is between 10 and 100, 250, 500, 1,000, 2,000, 2,500, or 5,000, and wherein a ratio of the total number of sample nucleic acid molecules in the population of sample nucleic acid molecules to the diversity of MITs in the set of MITs is greater than 500:1, 1,000:1, 10,000:1, or 100,000:1; attaching at least one MIT from the set of MITs to a sample nucleic acid segment of at least one sample nucleic acid molecule of the population of sample nucleic acid molecules to form a population of tagged nucleic acid molecules wherein the at least one MIT is located 5' and/or 3' to a sample nucleic acid segment on each tagged nucleic acid molecule and wherein the population of tagged nucleic acid molecules comprise at least one copy of each MIT in the set of MITs; amplifying the population of tagged nucleic acid molecules to create a library of tagged nucleic acid molecules; determining, using high-throughput sequencing, the sequences of the attached MITs and at least a portion of the sample nucleic acid segments of the tagged nucleic acid molecules in the library of tagged nucleic acid molecules, wherein the sequence of the at least one MIT on each tagged nucleic acid molecule identifies the individual sample nucleic acid molecule that gave rise the tagged nucleic acid molecule; and identifying tagged nucleic acid molecules having amplification errors by identifying nucleic acid segments that have a nucleotide sequences that is found in less than 25% of tagged nucleic acid molecules derived from the same initial sample nucleic acid molecule. The total number of MIT molecules in the reaction mixture is typically greater than the total number of sample nucleic acid molecules in the reaction mixture.

In some embodiments, the method can further include a sample with fragments of genomic DNA that are greater than 20 nucleotides and not more than 1,000 nucleotides, or greater than 50 nucleotides and not more than 500 nucleotides in length, and wherein the diversity of combinations of any 2 MITs in the set of MITs exceeds the total number of DNA fragments or sample nucleic acid molecules that span a target locus in the genome. In some embodiments, the method can be used for example, on a maternal blood sample, wherein the copy number determination is for non-invasive prenatal testing. In some embodiments, the method can be used on a blood sample from an individual having or suspected of having cancer.

In another aspect provided herein is a method of determining the number of copies of one or more chromosomes or chromosome segments of interest from a target individual in a sample of blood or a fraction thereof, from the target individual or from the mother of the target individual, that includes the following: forming a population of tagged nucleic acid molecules by reacting a population of nucleic acid molecules of the sample with a set of nucleic acid molecular index tags (MITs), wherein the number of different MITs in the set of MITs is between 10 and 10,000 or between 10 and 1,000, wherein a ratio of the total number of sample nucleic acid molecules in the population of sample nucleic acid molecules to the diversity of MITs in the set of MITs is greater than 500:1, 1,000:1, 10,000:1, or 100,000:1, wherein at least some of the sample nucleic acid molecules comprise one or more target loci of a plurality of target loci on the chromosome or chromosome segment of interest, and wherein the sample is 1.0 ml or less of blood or a fraction of blood derived from 1.0 ml or less of blood; amplifying the population of enriched tagged nucleic acid molecules to create a library of tagged nucleic acid molecules; determining the sequences of the attached MITs and at least a portion of the sample nucleic acid segments of the tagged nucleic acid molecules in the library of tagged nucleic acid molecules, to determine the identity of a sample nucleic acid molecule that gave rise to a tagged nucleic acid molecule; measuring a quantity of DNA for each target locus by counting the number of sample nucleic acid molecules that comprise each target locus using the determined identities; and determining, on a computer, the number of copies of the one or more chromosomes or chromosome segments of interest using the quantity of DNA at each target locus in the sample nucleic acid molecules. The total number of MIT molecules in the reaction mixture is typically greater than the total number of sample nucleic acid molecules in the reaction mixture.

In some embodiments, the number of target loci and the volume of the sample provide an effective amount of total target loci to achieve a desired sensitivity and specificity for the copy number determination. In some embodiments, the method can further include using a number of target loci and a total number of sample nucleic acid molecules that span the target loci to provide an effective amount of total sequencing reads to achieve a desired sensitivity and specificity for the copy number determination. In some embodiments, this can be at least 10, 25, 50, 100, 250, 500, 1,000, 1,500, 2,000, 2,500, 3,000, 4,000, 5,000, 6,000, 7,000, 8,000, 9,000, 10,000, 15,000, 20,000, 25,000, 30,000, 40,000, or 50,000 target loci. In some embodiments, the method can include at least 10,000, 100,000, 500,000, or 1,000,000 total target loci in the sample, wherein the set of MITs comprises at least 25, 30, 32, 50, 64, 100, 200, 250, 500, or 1,000 MITs, wherein the sample is from the mother and includes at least 1%, 2%, 3%, 4%, or 5% fetal nucleic acids compared to maternal nucleic acids, and wherein the desired specificity is 95%, 96%, 97%, 98%, or 99% and the desired sensitivity is 95%, 96%, 97%, 98%, or 99%.

In some embodiments, the method can include a ligation reaction to form the population of tagged nucleic acid molecules, wherein the population of tagged nucleic acid molecules are enriched using hybrid capture before amplifying, and wherein the number of total target loci in the sample is at least 4, 5, 6, 7, 8, 9, 10, 15, or 20 times greater than the number of total target loci required to meet the desired specificity and the desired sensitivity.

In some embodiments, the method can further include determining a probability of each copy number hypothesis from a set of copy number hypotheses for the one or more chromosomes or chromosome segments of interest using the quantity of DNA at each target locus and selecting the copy number hypothesis with the highest probability.

In some embodiments, the method can include using a plurality of disomic loci from one or more chromosome or chromosome segments expected to be disomic on the sample nucleic acid molecules to determine the probability of each copy number hypothesis by comparing the quantity of DNA at the plurality of target loci to the quantity of DNA at the disomic loci.

In some embodiments, the method can be used on a maternal blood sample wherein the copy number determination is for non-invasive prenatal testing. In some embodiments, the method can be used on a blood sample from an individual having or suspected of having cancer.

Another aspect provided herein is a reaction mixture that includes: a population of at least 100,000, 200,000, 250,000, 500,000,000, or 1,000,000 sample nucleic acid molecules between 10, 20, 25, 50, or 100 and 200, 250, 500, 1,000, 2,000, or 2,500 nucleotides in length; a set of between 10 and 100, 200, 250, 500, 1,000, or 10,000 Molecular Index Tags (MITs) between 3, 4, 5, 6, or 7 nucleotides in length on the low end of the range and 8, 9, 10, 11, 12, 15, or 20 nucleotides in length on the high end of the range; and a ligase, wherein the MITs are separate nucleic acid molecules from the sample nucleic acid molecules, wherein the total number of MIT molecules in the reaction mixture is greater than the total number of sample nucleic acid molecules in the reaction mixture, wherein a ratio of the total number of sample nucleic acid molecules in the reaction mixture to the diversity of the MITs in the set of MITs in the reaction mixture is at least 1,000:1, 10,000:1, or 100,000:1, wherein the sequence of each of the MITs in the set of MITs differs from all other MIT sequences in the set by at least 2 nucleotides; and wherein the reaction mixture comprises at least two copies of every MIT.

In another aspect, the present disclosure provides a method of determining the number of copies of one or more chromosomes or chromosome segments of interest in a sample of blood or a fraction thereof, from a target individual, the method including: forming a reaction mixture comprising a population of sample nucleic acid molecules derived from the sample and a set of at least 32 Molecular Index Tags (MITs), wherein each MIT in the set of MITs is a double-stranded nucleic acid molecule comprising a different nucleic acid sequence, wherein the sample is derived from no more than 1.0 ml of blood, wherein a ratio of the total number of sample nucleic acid molecules in the population of sample nucleic acid molecules to the diversity of MITs in the set of MITs is greater than 1,000:1, and wherein at least some of the sample nucleic acid molecules comprise one or more target loci of at least 1,000 target loci on the chromosome or chromosome segment of interest; attaching at least two MITs from the set of MITs to a sample nucleic acid segment of at each sample nucleic acid molecule of the population of sample nucleic acid molecules to form a population of tagged nucleic acid molecules wherein each of the at least two MITs is located 5' and/or 3' to a sample nucleic acid segment on each tagged nucleic acid molecule and wherein the population of tagged nucleic acid molecules comprise at least one copy of each MIT of the set of MITs; amplifying the population of tagged nucleic acid molecules to create a library of tagged nucleic acid molecules; determining the sequences of the attached MITs and at least a portion of the sample nucleic acid segments of the tagged nucleic acid molecules in the library of tagged nucleic acid molecules, wherein the sequence of the attached MITs and the at least a portion of the nucleic segment on each tagged nucleic acid molecule are used to identify tagged nucleic acid molecules that belong to the same paired MIT nucleic acid segment family, wherein the at least two MITs on each member of a paired MIT nucleic acid segment family are identical or complementary, wherein nucleic acid molecule segments of each member of an MIT nucleic acid segment family map to the same coordinates on the genome of the source of the population of sample nucleic acid molecules, and wherein at least 25% of the sample nucleic acid molecules are represented in the library of tagged nucleic acid molecules whose sequence is determined; determining for the sample nucleic acid molecules, a quantity of DNA for each target locus by counting the number of MIT nucleic acid segment families that span each target locus; and determining, on a computer, the number of copies of the one or more chromosomes or chromosome segments of interest using the quantity of DNA at each target locus in the sample nucleic acid molecules. The total number of MIT molecules in the reaction mixture is typically greater than the total number of sample nucleic acid molecules in the reaction mixture. MIT nucleic acid segment families share identical MITs in the same relative positions to the nucleic acid segment as well as the same fragment end positions and the same sequenced orientation (positive or negative relative to the human genome). Each sample nucleic acid molecule that entered into the MIT library preparation process can generate two families, one mapping to each of the positive and negative genomic orientations. Two MIT nucleic acid segment families can be paired, one with a positive orientation and one with a negative orientation, if the MIT nucleic acid segment families contain complementary MITs in the same relative position to the same nucleic acid segment as well as complementary fragment end positions. In some embodiments, the paired MIT nucleic acid segment families can be used to verify the presence of sequence differences in the sample nucleic acid molecule.

In some embodiments, the method can further include analyzing single-nucleotide polymorphic loci for the one or more target loci on the one or more chromosomes or chromosome segments. In further embodiments, before determining the number of copies of the one or more chromosomes or chromosome segments of interest, a ratio of sample nucleic acid molecules comprising different alleles at each locus can be estimated by counting the number of MIT nucleic acid segment families that include each allele at each locus and using the estimated ratio of sample nucleic acid molecules including different alleles at each locus to determine the number of copies of the one or more chromosomes or chromosome segments of interest.

In some embodiments, the method can include a sample of circulating cell-free human DNA wherein the diversity of possible combinations of any 2 MITs in the set of MITs exceeds the number of circulating cell-free DNA fragments or sample nucleic acid molecules in the reaction mixture that span one or more target loci in the human genome.

In some embodiments, the method can include analyzing a plurality of disomic loci on a chromosome or chromosome segment expected to be disomic, wherein the method further includes determining for the sample nucleic acid molecules, a quantity of DNA for each disomic locus by counting the number of MIT nucleic acid segment families that span each disomic locus, and wherein the determining the number of copies of the one or more chromosomes or chromosome segments of interest uses the quantity of DNA for each target locus and the quantity of DNA for each disomic locus.

In some embodiments, the method can further include creating, on a computer, a plurality of ploidy hypotheses each pertaining to a different possible ploidy state of the chromosome or chromosome segment of interest and determining, on a computer, a relative probability of each of the ploidy hypotheses using the quantity of DNA for each target locus to identify the copy number of the individual by selecting the ploidy state corresponding to the hypothesis with the greatest probability.

In some embodiments, the method can be used on a maternal sample wherein the copy number determination is for non-invasive prenatal testing. In some embodiments, the method can be used on a sample from an individual having or suspected of having cancer.

In another aspect, provided herein is a method of determining the number of copies of one or more chromosomes or chromosome segments of interest in a sample of blood or a fraction thereof, from a target individual, where the method includes: forming a population of tagged nucleic acid molecules by reacting a population of sample nucleic acid molecules and a set of Molecular Index Tags (MITs), wherein the sample is 2.5, 2.0, 1.0, or 0.5 ml or less, wherein the number of different MITs in the set of MITs is between 10 and 100, 200, 250, 500, 1,000, 2,000, 2,500, 5,000, or 10,000, wherein a ratio of the total number of sample nucleic acid molecules in the population of sample nucleic acid molecules to the diversity of MITs in the set of MITs is at least 100:1, 500:1, 1,000:1, 10,000:1, or 100,000:1, wherein each tagged nucleic acid molecule comprises one or two MITs located 5' and 3', respectively, for example two MITs located 5' and 3', respectively, to a nucleic acid segment from the population of nucleic acid molecules, and wherein a portion of the sample nucleic acid molecules comprise one or more target loci of a plurality of loci on the chromosome or chromosome segment of interest; amplifying the population of tagged nucleic acid molecules to create a library of tagged nucleic acid molecules; and determining the sequences of the attached MITs and at least a portion of the sample nucleic acid segments of the tagged nucleic acid molecules in the library of tagged nucleic acid molecules, for example determining the sequence of at least 10, 20, 30, 40, 50, 60, 70, 80, 90, or 95%, or 100% of the sample nucleic acid segments, wherein the sequence of the attached MITs and the at least a portion of the nucleic segment on each tagged nucleic acid molecule are used to identify tagged nucleic acid molecules that belong to the same paired MIT nucleic acid segment family, wherein the at least two MITs on each member of a paired MIT nucleic acid segment family are identical or complementary, and wherein nucleic acid molecule segments of each member of an MIT nucleic acid segment family map to the same coordinates on the genome of the source of the population of sample nucleic acid molecules; determining for the sample nucleic acid molecules, a quantity of DNA for each target locus by counting the number of MIT nucleic acid segment families that span each target locus; and determining, on a computer, the number of copies of the one or more chromosomes or chromosome segments of interest using the quantity of DNA at each target locus in the sample nucleic acid molecules. The total number of MIT molecules in the reaction mixture is typically greater than the total number of sample nucleic acid molecules in the reaction mixture.

In some embodiments, the method can further include creating, on a computer, a plurality of ploidy hypotheses each pertaining to a different possible ploidy state of the chromosome or chromosome segment of interest and determining, on a computer, a relative probability of each of the ploidy hypotheses using the quantity of DNA for each target locus to identify the copy number of the individual by selecting the ploidy state corresponding to the hypothesis with the greatest probability.

In some embodiments, the method can be used on a maternal blood sample wherein the copy number determination is for non-invasive prenatal testing. In some embodiments, the method can be used on a blood sample from an individual having or suspected of having cancer.

In another aspect, provided herein is a reaction mixture which includes: a population of between 500,000,000 and 1,000,000,000,000 sample nucleic acid molecules between 10 and 1,000 nucleotides in length; a set of between 10 and 1,000 Molecular Index Tags (MITs) between 4 and 8 nucleotides in length; and a ligase, wherein the MITs are nucleic acid molecules, wherein a ratio of the total number of the sample nucleic acid molecules in the reaction mixture to the diversity of the MITs in the set of MITs is between 1,000:1 and 1,000,000:1, wherein the sequence of each of the MITs in the set of MITs differs from all other MIT sequences in the set by at least 2 nucleotides, and wherein the set comprises at least two copies of every MIT.

In some embodiments, the method can further include using sample nucleic acid molecules that have not been amplified in vitro. In some embodiments, the method can be used on a maternal sample wherein the copy number determination is for non-invasive prenatal testing. In some embodiments, the method can be used on a sample from an individual having or suspected of having cancer.

In another aspect, provided herein is a reaction mixture that includes: a population of between 500,000,000 and 5,000,000,000,000 sample nucleic acid molecules; and a set of primers with sequences designed to bind to internal sequences of the sample nucleic acid molecules; wherein the primers further comprise a Molecular Index Tag (MIT) from a set of between 10 and 500 MITs, wherein the MITs are nucleic acid molecules between 4 and 8 nucleotides in length, wherein a ratio of the diversity of the sample nucleic acid molecules in the reaction mixture to the diversity of the MITs in the set of MITs in the reaction mixture is between 10,000:1 and 1,000,000:1, and wherein the sequence of each of the MITs in the set of MITs differs from all other MIT sequences in the set by at least 2 nucleotides.

In some embodiments, the method can further include having more primers in the reaction mixture than the total number of sample nucleic acid molecules.

In another aspect, provided herein is a population of tagged nucleic acid molecules that includes: between 500,000,000 and 5,000,000,000,000 different tagged nucleic acid molecules between 10 and 1,000 nucleotides in length, wherein each of the tagged nucleic acid molecules comprise at least one Molecular Index Tag (MIT) located 5' and/or 3' to a sample nucleic acid segment, wherein the at least one MIT is a member of a set of between 10 and 500 different MITs each between 4 and 20 nucleotides in length, wherein the population of tagged nucleic acid molecules comprises each member of the set of MITs, wherein at least two tagged nucleic acid molecules of the population comprise at least one identical MIT and a sample nucleic acid segment that is greater than 50% different, and wherein a ratio of the number of sample nucleic acid segments to the number of MITs in the population is between 1,000:1 and 1,000,000,000:1.

In some embodiments, the population of tagged nucleic acid molecules can be a part of a reaction mixture that further includes a polymerase or a ligase. In various embodiments, the population of nucleic acid molecules can be used to generate a library, wherein the library includes between 1, 2, 3, 4, 5, 6, 7, 8, 9, 10, 25, 50, 100, 250, 500, and 1,000 copies of some or all of the population of nucleic acid molecules on the low end of the range and 3, 4, 5, 6, 7, 8, 9, 10, 25, 50, 100, 250, 500, 1,000, 2,500, 5,000, and 10,000 copies of some or all of the population of nucleic acid molecules on the high end of the range. In some embodiments, the library can include at least 2, 3, 4, 5, 6, 7, 8, 9, 10, 15, 20, 25, 50, 100, 250, 500, or 1,000 tagged nucleic acid molecules with MITs with identical sequences and a sample nucleic acid segment that is between 50%, 60%, 70%, 75%, 80%, 85%, 90%, 95%, 96%, 97%, 98%, 99%, and 99.9% identical on the low end of the range and 60%, 70%, 75%, 80%, 85%, 90%, 95%, 96%, 97%, 98%, 99%, 99.9%, and 100% identical on the high end of the range. In various embodiments, the library can include at least 2, 3, 4, 5, 6, 7, 8, 9, 10, 15, 20, 25, 50, 100, 250, 500, or 1,000 tagged nucleic acid molecules with MITs with identical sequences and a sample nucleic acid segment that has at least 1, 2, 3, 4, 5, 6, 7, 8, 9, 10, 11, 12, 13, 14, 15, 20, or 25 nucleotide differences. In some embodiments, the library of nucleic acid molecules can be clonally amplified onto a solid support or a plurality of solid supports.

In another aspect, provided herein is a population of tagged nucleic acid molecules, wherein the population is formed by a method including: attaching at least one Molecular Index Tag (MIT) to a population of between 500,000,000 and 5,000,000,000,000 sample nucleic acid molecules comprising sample nucleic acid segments between 50 and 500 nucleotides in length, to form a tagged nucleic acid molecule comprising at least one MIT located 5' and/or 3' to a sample nucleic acid segment wherein the MITs are nucleic acid molecules, wherein the MITs are members of a set of between 10 and 500 different MITs each between 4 and 20 nucleotides in length, wherein the population of tagged nucleic acid molecules comprises each member of the set of MITs, wherein at least two tagged nucleic acid molecules of the population comprise at least one identical MIT and a sample nucleic acid segment that is greater than 50% different, and wherein a ratio of the diversity of sample nucleic acid molecule segments in the population to the diversity of MITs in the set of MITs is between 1,000:1 and 1,000,000,000:1.

In another aspect, provided herein is a kit including: a first container comprising a ligase; and a second container comprising a set of Molecular Index Tags (MITs), wherein each MIT in the set of MITs comprises a portion of a Y-adapter nucleic acid molecule of a set of Y-adapter nucleic acid molecules, where each Y-adapter of the set comprises a base-paired, double-stranded polynucleotide segment and at least one non-base-paired single-stranded polynucleotide segment, wherein the sequence of each of the Y-adapter nucleic acid molecules in the set, other than the MIT sequence, is identical, and wherein the MIT is a double-stranded sequence that is part of the base-paired, double-stranded polynucleotide segment, wherein the set of MITs comprises between 10 and 500 MITs, wherein the MITs are between 4 and 8 nucleotides in length, and wherein the sequence of each of the MITs in the set of MITs differs from all other MIT sequences in the set by at least 2 nucleotides. The kit can further include a polymerase.

In some embodiments disclosed herein, the present disclosure provides a reaction mixture wherein a population of sample nucleic acid molecules is combined with a set of MITs under appropriate conditions to attach the MITs to the nucleic acid molecules or to a nucleic acid segment of the nucleic acid molecule to generate a population of tagged nucleic acid molecules. In some embodiments disclosed herein, the population of tagged nucleic acid molecules can be processed, for example by amplification(s), which can be part of a high-throughput sequencing sample preparation workflow, and used for downstream analysis, such as by high-throughput sequencing. The MITs can be attached through direct ligation or as a portion of an amplification, such as a PCR primer. Typically, MITs are 5' to the sequence-specific binding region of the primer but the primers can be designed such that they are between a universal binding region and a sequence-specific binding region, or the MITs are internal to the sequence-specific binding region and form a loop upon hybridization with a sample nucleic acid molecule. In some embodiments, the MITs can be on forward primers such that amplification with the primers generates tagged nucleic acid molecules with MITs 5' to the target locus. In some embodiments, the MITs can be on reverse primers such that amplification with the primers generates tagged nucleic acid molecules with MITs 3' to the target locus. In some embodiments, the MITs can be on both forward and reverse primers such that amplification with the primers generates tagged nucleic acid molecules with MITs both 5' and 3' to the target locus.

In some embodiments disclosed herein, the MITs can be single-stranded or double-stranded nucleic acid molecules. In some embodiments, the sequences of the MIT can differ from the sequences of all the other MITs in the set of MITs by at least 1, 2, 3, 4, 5, 6, 7, 8, 9, or 10 nucleotides. In some embodiments, the MITs in the set of MITs are typically the same length. In other embodiments, the MITs in the set of MITs are different length. In any of the embodiments disclosed herein, the lengths of the MITs are 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides in length.

In some embodiments, the MITs can be at least a portion of a Y-adaptor or a single-stranded oligonucleotide or double-stranded nucleic acid, such as a double-stranded adaptor. In some embodiments, the MITs can be a portion of a Y-adapter nucleic acid molecule of a set of Y-adapter nucleic acid molecules, where each Y-adapter of the set includes a base-paired, double-stranded polynucleotide segment and at least one non-base-paired single-stranded polynucleotide segment, wherein the sequence of each of the Y-adapter nucleic acid molecules in the set, other than the MIT sequence, is identical, and wherein the MIT is a double-stranded sequence that is part of the base-paired, double-stranded polynucleotide segment. In some embodiments, the double-stranded polynucleotide segment can be between 5, 10, 15, and 20 nucleotides in length on the low end of the range and 10, 15, 20, 25, 30, 35, 40, 45, and 50 nucleotides in length on the high end of the range, not including the MIT, and the single-stranded polynucleotide segment can be between 5, 10, 15, and 20 nucleotides in length on the low end of the range and 10, 15, 20, 25, 30, 35, 40, 45, and 50 nucleotides in length on the high end of the range. In some embodiments, the MITs can be between 3, 4, 5, 6, 7, 8, 9, 10, or 15 nucleotides in length on the low end of the range and 5, 6, 7, 8, 9, 10, 15, 20, 25, or 30 nucleotides in length on the high end of the range. In some embodiments disclosed herein, the MITs can be portions of oligonucleotides that further include sequences designed to bind to the sample nucleic acid molecules, universal primer binding sequences, and/or adapter sequences, especially adapter sequences useful for high-throughput sequencing. In some embodiments, the total lengths of the oligonucleotides can be between 10, 15, 20, 25, 30, 35, 40, 45, 50, 60, 70, 80, 90, or 100 nucleotides on the low end of the range and 25, 30, 35, 40, 45, 50, 60, 70, 80, 90, or 100 nucleotides on the high end of the range. In some embodiments, one or more MITs can be attached to the sample nucleic acid molecules. For example, in some embodiments, at least 1, 2, 3, 4, 5, 6, 7, 8, 9, or 10 MITs can be attached to the sample nucleic acid molecules. In some embodiments disclosed herein, the MITs can be attached 5' and/or 3' to the sample nucleic acid segment, which can be a portion or all of a sample nucleic acid molecule. In some embodiments, 2 MITs can be attached to the individual sample nucleic acid molecules, for example each of the sample nucleic acid molecules, wherein each tagged nucleic acid molecule comprises two MITs located 5' and 3' respectively, to a nucleic acid segment from the population of nucleic acid molecules.

In some embodiments disclosed herein, the sample nucleic acid molecules can be used in the reaction mixture before any other in vitro amplification has occurred. In some embodiments, the total number of sample nucleic acid molecules in the population of nucleic acid molecules can be between 100, 250, 500, 1,000, 2,500, 5,000, 10,000, 25,000, 50,000, 100,000, 250,000, 500,000, $1 \times 10^6$, $2.5 \times 10^6$, $5 \times 10^6$, $1 \times 10^7$, $1 \times 10^8$, $1 \times 10^9$, and $1 \times 10^{10}$ sample nucleic acid molecules on the low end of the range and 500, 1,000, 2,500, 5,000, 10,000, 25,000, 50,000, 100,000, 250,000, 500,000, $1 \times 10^6$, $2.5 \times 10^6$, $5 \times 10^6$, $1 \times 10^7$, $1 \times 10^8$, $1 \times 10^9$, $1 \times 10^{10}$, $1 \times 10^{11}$, and $1 \times 10^{12}$ sample nucleic acid molecules on the high end of the range. In some embodiments disclosed herein, the total number of sample nucleic acid molecules in the reaction mixture can be greater than the diversity of the MITs in the set of MITs. For example, a ratio of the total number of sample nucleic acid molecules to the diversity of the MITs in the set of MITs can be at least 2:1, 10:1, 100:1, 1,000:1, 5,000:1, 10,000:1, 25,000:1, 50,000:1, 100,000:1, 250,000:1, 500,000:1, 1,000,000:1, 5,000,000:1, 10,000,000:1, $1 \times 10^8$:1 $1 \times 10^9$:1, $1 \times 10^{10}$:1, or more. In some embodiments, the diversity of the possible combinations of attached MITs can be greater than the total number of sample nucleic acid molecules in the reaction mixture that span a target locus. For example, a ratio of the diversity of the possible combinations of attached MITs, for example combinations of any 2, 3, 4, 5, etc. MITs depending on how many MITs are attached to the sample nucleic acid molecules, to the total number of sample nucleic acid molecules that span a target locus can be at least 1:01, 1.1:1, 1.5:1, 2:1, 3:1, 4:1, 5:1, 6:1, 7:1 8:1, 9:1, 10:1, 15:1, 20:1, 25:1, 50:1, 100:1, 500:1 or, 1,000:1. In some embodiments, the MITs in the set of MITS can be attached to at least 2, 3, 4, 5, 6, 7, 8, 9, 10, 25, 50, 100, 250, 500, 1,000, 2,500, 5,000, 10,000, 25,000, 50,000, 100,000, 250,000, 500,000, $1 \times 10^6$, $2.5 \times 10^6$, $5 \times 10^6$, $1 \times 10^7$, $1 \times 10^8$, $1 \times 10^9$, $1 \times 10^{10}$, $1 \times 10^{11}$, or $1 \times 10^{12}$ different sample nucleic acid molecules to form the population of tagged nucleic acid molecules.

In some embodiments disclosed herein, at least 1, 2, 3, 4, 5, 6, 7, 8, 9, 10, 25, 50, 100, 250, 500, 1,000, 2,500, 5,000, 10,000, 25,000, 50,000, 100,000, 250,000, 500,000, $1 \times 10^6$, $2.5 \times 10^6$, $5 \times 10^6$, $1 \times 10^7$, $1 \times 10^8$, $1 \times 10^9$, $1 \times 10^{10}$, $1 \times 10^{11}$, and $1 \times 10^{12}$ sample nucleic acid molecules can have MITs attached in the reaction mixture. In some embodiments, at least 1%, 2%, 3%, 4%, 5%, 10%, 15%, 20%, 25%, 30%, 35%, 40%, 45%, 50%, 55%, 60%, 70%, 75%, 80%, 85%, 90%, 95%, 96%, 97%, 98%, 99%, 99.9%, or 100% of the sample nucleic acid molecules in the reaction mixture can have MITs attached.

In some embodiments disclosed herein, the reaction mixture can include more MIT molecules than sample nucleic acid molecules. For example, in some embodiments, the total number of MIT molecules in the reaction mixture can be least 2, 3, 4, 5, 6, 7, 8, 9, or 10 times greater than the total number of sample nucleic acid molecules in the reaction mixture. In certain respects, the fold difference is dependent on the number of MITs to be attached. For example, if 2 MITs are to be attached, then the total number of MIT molecules in the reaction mixture can be least 2 times greater than to the total number of sample nucleic acid molecules in the reaction mixture; if 3 MITs are to be attached, then the total number of MIT molecules in the reaction mixture can be least 3 times greater than to the total number of sample nucleic acid molecules in the reaction mixture, and so on. In some embodiments, the ratio of the total number of MITs with identical sequences in the reaction mixture to the total number of nucleic acid molecules in the reaction mixture can be between 0.1:1, 0.2:1, 0.3:1, 0.4:1, 0.5:1. 1:1, 1.5:1 and 2:1 on the low end of the range and 0.3:1, 0.4:1, 0.5:1. 1:1, 1.5:1, 2:1. 3:1, 4:1, 5:1, 6:1, 7:1, 8:1, 9:1, and 10:1 on the high end of the range.

In some embodiments, the sequences of the attached MITs and nucleic acid segments in the population of tagged nucleic acid molecules can be determined through sequencing, especially high-throughput sequencing. In some embodiments, the tagged nucleic acid molecules can be clonally amplified in preparation for sequencing, especially onto a solid support or a plurality of solid supports. In some embodiments, the determined sequences of the MITs on a tagged nucleic acid molecule can be used to identify the sample nucleic acid molecule from which the tagged nucleic acid molecule is derived, especially using the sequences of the ends of the nucleic acid segment or fragment-specific insert ends as disclosed herein. In some embodiments, the determined sequence of the nucleic acid segment on the tagged nucleic acid molecule can be used to aid in the identification of the sample nucleic acid molecules from which the tagged nucleic acid molecule is derived. In some embodiments, the determined sequence of the nucleic acid segment can be mapped to a location in the genome of the source of the sample nucleic acid molecules and this information can be used to aid in the identification.

In some embodiments, between 100, 250, 500, 1,000, 2,500, 5,000, 10,000, 25,000, 50,000, 100,000, 250,000, 500,000, $1\times10^6$, $2.5\times10^6$, $5\times10^6$, $1\times10^7$, $1\times10^8$, $1\times10^9$, and $1\times10^{10}$ tagged nucleic acid molecules on the low end of the range and 500, 1,000, 2,500, 5,000, 10,000, 25,000, 50,000, 100,000, 250,000, 500,000, $1\times10^6$, $2.5\times10^6$, $5\times10^6$, $1\times10^7$, $1\times10^8$, $1\times10^9$, $1\times10^{10}$, $1\times10^{11}$, and $1\times10^{12}$ tagged nucleic acid molecules on the high end of the range can be identified. In some embodiments, the tagged nucleic acid molecules derived from the two strands of one sample nucleic acid molecule can be identified and used to generate paired MIT families. In downstream sequencing reactions, where single-stranded nucleic acid molecules are typically sequenced, an MIT family can be identified by identifying tagged nucleic acid molecules with identical or complementary MIT sequences. In these embodiments, the paired MIT families can be used to verify the presence of sequence differences in the sample nucleic acid molecule. In some further embodiments, the determined sequences of the nucleic acid segments are used to generate paired MIT nucleic acid segment families that have complementary or identical MIT and nucleic acid segment sequences. In these embodiments, the paired MIT nucleic acid segment families can be used to verify the presence of sequence differences in the sample nucleic acid molecule.

In some embodiments, tagged nucleic acid molecules with particular target loci can be enriched. In some embodiments, one-sided or two-sided PCR can be used to enrich these target loci on one or more chromosomes. In some embodiments, hybrid capture can be used. In some embodiments, between 1, 2, 3, 4, 5, 6, 7, 8, 9, 10, 15, 20, 25, 50, 100, 250, 500, 1,000, 2,500, 5,000, 10,000, 15,000, or 20,000 target loci on the low end of the range and 5, 6, 7, 8, 9, 10, 15, 20, 25, 50, 100, 250, 500, 1,000, 2,500, 5,000, 10,000, 15,000, 20,000, 25,000, 50,000, 100,000, and 250,000 target loci on the high end of the range can be targeted for enrichment. In some embodiments, the target loci can be between 1, 2, 3, 4, 5, 6, 7, 8, 9, 10, 11, 12, 13, 14, 15, 16, 17, 18, 19, 20, 25, 50, 75, and 100 nucleotides in length on the low end of the range and 10, 11, 12, 13, 14, 15, 16, 17, 18, 19, 20, 25, 50, 75, 100, 125, 150, 200, 250, 300, 400, 500, and 1,000 nucleotides in length on the high end of the range. In some embodiments, the target loci on different sample nucleic acid molecules can be at least 50%, 60%, 70%, 80%, 90% 95%, 96%, 97%, 98%, 99%, 99.9%, or 100% identical or share at least 50%, 60%, 70%, 80%, 90% 95%, 96%, 97%, 98%, 99%, 99.9%, or 100% sequence identity.

In some embodiments disclosed herein, the sample can be from a mammal. In some embodiments, the sample can be from a human, especially from a human blood sample or a fraction thereof. In any of the disclosed embodiments, the sample can be less than 0.1, 0.2, 0.25, 0.5, 1, 1.25, 1.5, 1.75, 2, 2.5, 3, 3.5, 4, 4.5 or 5 ml of blood or plasma. In some embodiments disclosed herein, the sample can include circulating cell-free human DNA. In some embodiments, the sample including circulating cell-free human DNA can be from a mother and can include maternal and fetal DNA. In some embodiments, the sample can include circulating cell-free human DNA can be a blood sample from a person having or suspected of having cancer and can include normal and tumor DNA.

Other features and advantages of the present disclosure will be apparent from the following detailed description and from the claims.

BRIEF DESCRIPTION OF THE DRAWINGS

FIG. 1 discloses SEQ ID NOS 1-2, 2, 1, 3-4, 4 and 3, respectively, in order of appearance.

FIG. 2 discloses SEQ ID NOS 5-6, 6, 5, 7-8, 8, 7 and 9-14, respectively, in order of appearance.

In FIG. 3A, the first base of the MIT would be the first base in Read 2. The amplicon generated after hybrid capture (FIG. 3B) has MITs on both sides of the amplicon wherein the first base of Read 1 is the first base of MIT1 and the first base of Read 2 is the first base of MIT2.

FIG. 4 is a table showing the results of a sequencing run using MITs.

Figure 1:
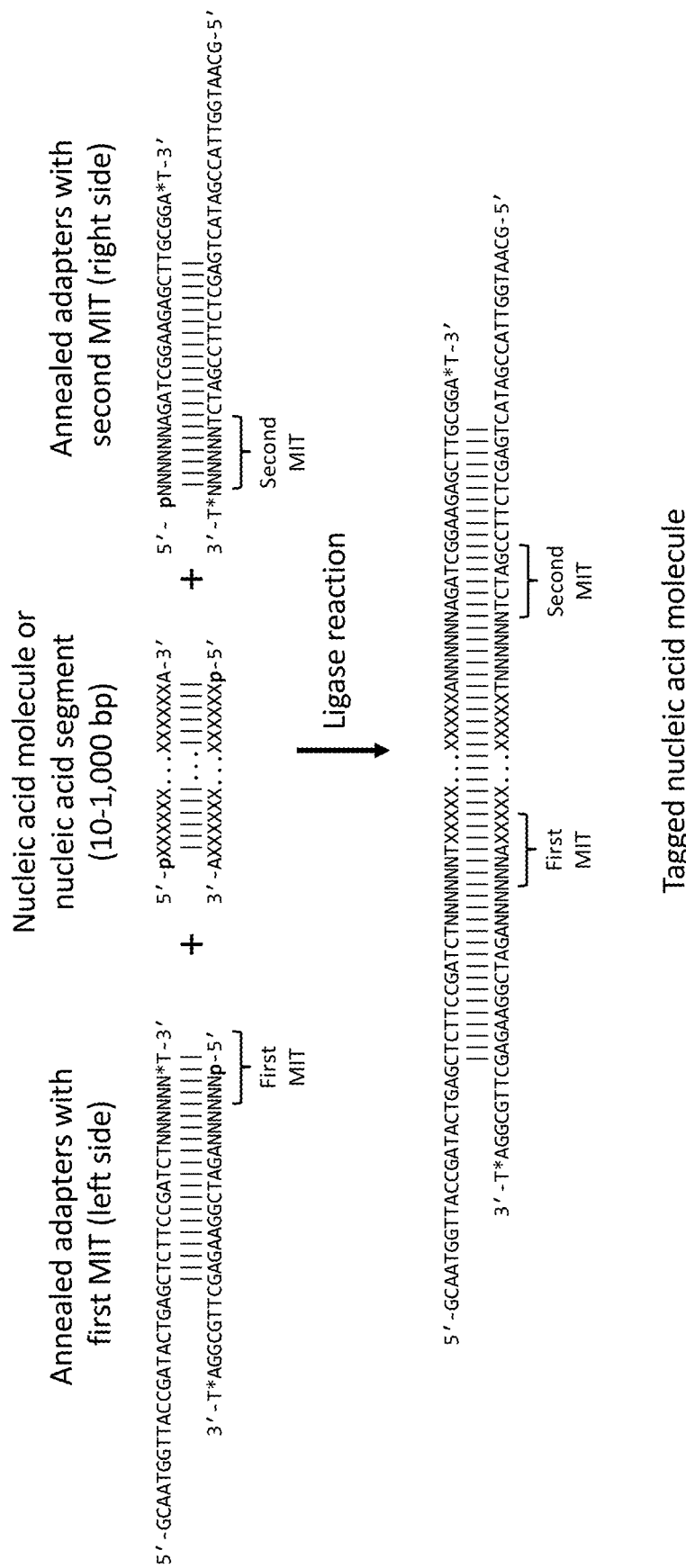
FIG. 1 is a schematic showing the attachment of two MITs to a nucleic acid molecule or nucleic acid segment using ligation.

The above-identified figures are provided by way of representation and not limitation.

DETAILED DESCRIPTION OF THE INVENTION

The present disclosure relates to methods and compositions that include oligonucleotide tags, herein referred to as Molecular Index Tags (MITs), that are attached to a population of nucleic acid molecules from a sample to identify individual sample nucleic acid molecules from the population of nucleic acid molecules (i.e. members of the population) after sample processing for a sequencing reaction. The sequencing reaction in some embodiments, is a high-throughput sequencing reaction performed on tagged nucleic acid molecules that are derived from sample nucleic acid molecules. Unlike prior art methods that relate to unique identifiers and teach having a diversity of unique identifiers that is greater than the number of sample nucleic acid molecules in a sample in order to tag each sample nucleic acid molecule with a unique identifier, the present disclosure typically involves many more sample nucleic acid molecules than the diversity of MITs in a set of MITs. In fact, methods and compositions herein can include more than 1,000, $1 \times 10^6$, $1 \times 10^9$, or even more starting molecules for each different MIT in a set of MITs. Yet the methods can still identify individual sample nucleic acid molecules that give rise to a tagged nucleic acid molecule after amplification.

In the methods and compositions herein, the diversity of the set of MITs is advantageously less than the total number of sample nucleic acid molecules that span a target locus but the diversity of the possible combinations of attached MITs using the set of MITs is greater than the total number of sample nucleic acid molecules that span a target locus. Typically, to improve the identifying capability of the set of MITs, at least two MITs are attached to a sample nucleic acid molecule to form a tagged nucleic acid molecule. The sequences of attached MITs determined from sequencing reads can be used to identify clonally amplified identical copies of the same sample nucleic acid molecule that are attached to different solid supports or different regions of a solid support during sample preparation for the sequencing reaction. The sequences of tagged nucleic acid molecules can be compiled, compared, and used to differentiate nucleotide mutations incurred during amplification from nucleotide differences present in the initial sample nucleic acid molecules.

Sets of MITs in the present disclosure typically have a lower diversity than the total number of sample nucleic acid molecules, whereas many prior methods utilized sets of "unique identifiers" where the diversity of the unique identifiers was greater than the total number of sample nucleic acid molecules. Yet MITs of the present disclosure retain sufficient tracking power by including a diversity of possible combinations of attached MITs using the set of MITs that is greater than the total number of sample nucleic acid molecules that span a target locus. This lower diversity for a set of MITs of the present disclosure significantly reduces the cost and manufacturing complexity associated with generating and/or obtaining sets of tracking tags. Although the total number of MIT molecules in a reaction mixture is typically greater than the total number of sample nucleic acid molecules, the diversity of the set of MITs is far less than the total number of sample nucleic acid molecules, which substantially lowers the cost and simplifies the manufacturability over prior art methods. Thus, a set of MIT's can include a diversity of as few as 3, 4, 5, 10, 25, 50, or 100 different MITs on the low end of the range and 10, 25, 50, 100, 200, 250, 500, or 1000 MITs on the high end of the range, for example. Accordingly, in the present disclosure this relatively low diversity of MITs results in a far lower diversity of MITs than the total number of sample nucleic acid molecules, which in combination with a greater total number of MITs in the reaction mixture than total sample nucleic acid molecules and a higher diversity in the possible combinations of any 2 MITs of the set of MITs than the number of sample nucleic acid molecules that span a target locus, provides a particularly advantageous embodiment that is cost-effective and very effective with complex samples isolated from nature. Furthermore, by mapping sequenced nucleic acid molecules to the genome additional advantages are provided such as simpler analytics and identifying information about the sequence of the sample nucleic acid molecule compared to the reference genome.

Brief Description of Illustrative Methods

Accordingly, provided herein in one aspect is a method for sequencing a population of sample nucleic acid molecules, that can optionally further include using the sequencing to identify individual sample nucleic acid molecules from a population of sample nucleic acid molecules. In some embodiments, the population of nucleic acid molecules has not been amplified in vitro before attaching the MITs and can include between $1 \times 10^8$ and $1 \times 10^{13}$, or in some embodiments, between $1 \times 10^9$ and $1 \times 10^{12}$ or between $1 \times 10^{10}$ and $1 \times 10^{12}$, sample nucleic acid molecules. In some embodiments, the methods include forming a reaction mixture that includes the population of nucleic acid molecules and a set of MITs, wherein the total number of nucleic acid molecules in the population of nucleic acid molecules is greater than the diversity of MITs in the set of MITs and wherein there are at least three MITs in the set. In some embodiments, the diversity of the possible combinations of attached MITs using the set of MITs is more than the total number of sample nucleic acid molecules that span a target locus and less than the total number of sample nucleic acid molecules in the population. In some embodiments, the diversity of set of MITs can include between 10 and 500 MITs with different sequences. The ratio of the total number of nucleic acid molecules in the population of nucleic acid molecules in the sample to the diversity of MITs in the set, in certain methods and compositions herein, can be between 1,000:1 and 1,000,000,000:1. The ratio of the diversity of the possible combinations of attached MITs using the set of MITs to the total number of sample nucleic acid molecules that span a target locus can be between 1.01:1 and 10:1. The MITs typically are composed at least in part of an oligonucleotide between 4 and 20 nucleotides in length as discussed in more detail herein. The set of MITs can be designed such that the sequences of all the MITs in the set differ from each other by at least 2, 3, 4, or 5 nucleotides.

In some embodiments, provided herein, at least one (e.g. two) MIT from the set of MITs are attached to each nucleic acid molecule or to a segment of each nucleic acid molecule of the population of nucleic acid molecules to form a population of tagged nucleic acid molecules. MITs can be attached to a sample nucleic acid molecule in various configurations, as discussed further herein. For example, after attachment one MIT can be located on the 5' terminus of the tagged nucleic acid molecules or 5' to the sample nucleic acid segment of some, most, or typically each of the tagged nucleic acid molecules, and/or another MIT can be located 3' to the sample nucleic acid segment of some, most, or typically each of the tagged nucleic acid molecules. In other embodiments, at least two MITs are located 5' and/or 3' to the sample nucleic acid segments of the tagged nucleic acid molecules, or 5' and/or 3' to the sample nucleic acid segment of some, most, or typically each of the tagged nucleic acid molecules. Two MITs can be added to either the 5' or 3' by including both on the same polynucleotide segment before attaching or by performing separate reactions. For example, PCR can be performed with primers that bind to specific sequences within the sample nucleic acid molecules and include a region 5' to the sequence-specific region that encodes two MITs. In some embodiments, at least one copy of each MIT of the set of MITs is attached to a sample nucleic acid molecule, two copies of at least one MIT are each attached to a different sample nucleic acid molecule, and/or at least two sample nucleic acid molecules with the same or substantially the same sequence have at least one different MIT attached. A skilled artisan will identify methods for attaching MITs to nucleic acid molecules of a population of nucleic acid molecules. For example, MITs can be attached through ligation or appended 5' to an internal sequence binding site of a PCR primer and attached during a PCR reaction as discussed in more detail herein.

After or while MITs are attached to sample nucleic acids to form tagged nucleic acid molecules, the population of tagged nucleic acid molecules are typically amplified to create a library of tagged nucleic acid molecules. Methods for amplification to generate a library, including those particularly relevant to a high-throughput sequencing workflow, are known in the art. For example, such amplification can be a PCR-based library preparation. These methods can further include clonally amplifying the library of tagged nucleic acid molecules onto one or more solid supports using PCR or another amplification method such as an isothermal method. Methods for generating clonally amplified libraries onto solid supports in high-throughput sequencing sample preparation workflows are known in the art. Additional amplification steps, such as a multiplex amplification reaction in which a subset of the population of sample nucleic acid molecules are amplified, can be included in methods for identifying sample nucleic acids provided herein as well.

In some embodiments, of methods provided herein a nucleotide sequence of the MITs and at least a portion of the sample nucleic acid molecule segments of some, most, or all (e.g. at least 2, 3, 4, 5, 6, 7, 8, 9, 10, 20, 25, 50, 75, 100, 150, 200, 250, 500, 1,000, 2,500, 5,000, 10,000, 15,000, 20,000, 25,000, 50,000, 100,000, 1,000,000, 5,000,000, 10,000,000, 25,000,000, 50,000,000, 100,000,000, 250,000,000, 500,000,000, $1\times10^9$, $1\times10^{10}$, $1\times10^{11}$, $1\times10^{12}$, or $1\times10^{13}$ tagged nucleic acid molecules or between 10, 20, 25, 30, 40, 50, 60, 70, 80, or 90% of the tagged nucleic acid molecules on the low end of the range and 20, 25, 30, 40, 50, 60, 70, 80, or 90, 95, 96, 97, 98, 99, and 100% on the high end of the range) of the tagged nucleic acid molecules in the library of tagged nucleic acid molecules is then determined. The sequence of a first MIT and optionally a second MIT or more MITs on clonally amplified copies of a tagged nucleic acid molecule can be used to identify the individual sample nucleic acid molecule that gave rise to the clonally amplified tagged nucleic acid molecule in the library.

In some embodiments, sequences determined from tagged nucleic acid molecules sharing the same first and optionally the same second MIT can be used to identify amplification errors by differentiating amplification errors from true sequence differences at target loci in the sample nucleic acid molecules. For example, in some embodiments, the set of MITs are double stranded MITs that, for example, can be a portion of a partially or fully double-stranded adapter, such as a Y-adapter. In these embodiments, for every starting molecule, a Y-adapter preparation generates 2 daughter molecule types, one in a + and one in a − orientation. A true mutation in a sample molecule should have both daughter molecules paired with the same 2 MITs in these embodiments where the MITs are a double stranded adapter, or a portion thereof. Additionally, when the sequences for the tagged nucleic acid molecules are determined and bucketed by the MITs on the sequences into MIT nucleic acid segment families, considering the MIT sequence and optionally its complement for double-stranded MITs, and optionally considering at least a portion of the nucleic acid segment, most, and typically at least 75% in double-stranded MIT embodiments, of the nucleic acid segments in an MIT nucleic acid segment family will include the mutation if the starting molecule that gave rise to the tagged nucleic acid molecules had the mutation. In the event of an amplification (e.g. PCR) error, the worst-case scenario is that the error occurs in cycle 1 of the $1^{st}$ PCR. In these embodiments, an amplification error will cause 25% of the final product to contain the error (plus any additional accumulated error, but this should be <<1%). Therefore, in some embodiments, if an MIT nucleic acid segment family contains at least 75% reads for a particular mutation or polymorphic allele, for example, it can be concluded that the mutation or polymorphic allele is truly present in the sample nucleic acid molecule that gave rise to the tagged nucleic acid molecule. The later an error occurs in a sample preparation process, the lower the proportion of sequence reads that include the error in a set of sequencing reads grouped (i.e. bucketed) by MITs into a paired MIT nucleic acid segment family. For example, an error in a library preparation amplification will result in a higher percentage of sequences with the error in a paired MIT nucleic acid segment family, than an error in a subsequent amplification step in the workflow, such as a targeted multiplex amplification. An error in the final clonal amplification in a sequencing workflow creates the lowest percentage of nucleic acid molecules in a paired MIT nucleic acid segment family that includes the error.

Any sequencing method can be used to carry out methods provided herein, especially those where multiple amplified copies of a sample nucleic acid molecule are used to determine the sequence of the sample nucleic acid molecule, or especially of a plurality of sample nucleic acid molecules. Furthermore, tagged nucleic acid molecules yielding substantially the same (e.g. at least 60%, 70%, 75%, 80%, 85%, 90%, 95, 96, 97, 98, or 99% identical) sequence for their sample nucleic acid segment and different MIT tags can be compared to determine the diversity of sequences in a population of sample nucleic acid molecules, and to differentiate true variants or mutations from errors generated during sample preparation, even at low allelic frequency. The method embodiments of the present disclosure include methods for sequencing a population of sample nucleic acid molecules. Such methods are especially effective for high-throughput sequencing methods. Such methods are discussed in more detail herein.

The methods disclosed above and herein can be used for a number of purposes a skilled artisan would recognize in view of the present disclosure. For example, the methods can be used to determine the nucleic acid sequences of a population of nucleic acid molecules in a sample, to identify a sample nucleic acid molecule that gave rise to a tagged nucleic acid molecule, to identify a sample nucleic acid molecule from a population of sample nucleic acid molecules, to identify amplification errors, to measure amplification bias, and to characterize the mutation rates of polymerases. Further uses will be apparent to a person skilled in the art. In these methods, after determining the sequences of the tagged nucleic acid segments, the nucleic acid segments with substantially the same nucleic acid segment sequence and the same two MIT tags or nucleic acid segments with substantially the same or the same nucleic acid segment sequence and at least one different MIT tag can be used for comparisons and further analysis.

Sample and Library Preparation

In the various embodiments provided herein, the sample can be from a natural or non-natural source. In some embodiments, the nucleic acid molecules in the sample can be derived from a living organism or a cell. Any nucleic acid molecule can be used, for example, the sample can include genomic DNA covering a portion of or an entire genome, mRNA, or miRNA from the living organism or cell. In certain respects, the total lengths of the entire genome or DNA sequences in a sample divided by the average size of the nucleic acid molecules can be used to determine the number of nucleic acid molecules in the sample to represent the entire genome or all the DNA sequences. In further respects, this number can be used to determine the number of nucleic acid molecules that span a target locus in the sample. A locus can include a single nucleotide or a segment of 1 to 1,000, 10,000, 100,000, 1 million, or more nucleotides. As nonlimiting examples, a locus can be a single nucleotide polymorphism, an intron, or an exon. In some embodiments, a locus can include an insertion, deletion, or transposition. In some embodiments, the sample can include a blood, sera, or plasma sample. In some embodiments, the sample can include free floating DNA (e.g. circulating cell-free tumor DNA or circulating cell-free fetal DNA) in a blood, sera, or plasma sample. In these embodiments, the sample is typically from an animal, such as a mammal or human, and is typically present in fragments about 160 nucleotides in length. In some embodiments, the free-floating DNA is isolated from blood using an EDTA-2Na tube after removal of cellular debris and platelets by centrifugation. The plasma samples can be stored at −80° C. until the DNA is extracted using, for example, QIAamp DNA Mini Kit (Qiagen, Hilden, Germany), (e.g. Hamakawa et al., *Br J Cancer.* 2015; 112:352-356). However, the sample can be derived from other sources and nucleic acid molecules from any organism can be used for this method. In some embodiments, DNA derived from bacteria and/or viruses can be used to analyze true sequence variants within a mixed population, especially in environmental and biodiversity sampling.

Some embodiments disclosed herein are typically performed using sample nucleic acid molecules that were generated within and by a living cell. Such nucleic acid molecules are typically isolated directly from a natural source such as a cell or a bodily fluid without any in vitro amplification before the MITs are attached. Accordingly, the sample nucleic acid molecules are used directly in the reaction mixture to attach MITs. This circumvents the potential introduction of amplification errors before the sample nucleic acid molecules are tagged. This in turn improves the ability to differentiate real sequence variants from amplification errors. However, in some embodiments, sample nucleic acid molecules can be amplified before attaching the MITs. A skilled artisan will understand the best methods to use if amplification is necessary before attaching MITs. For example, a high-fidelity polymerase with proof-reading capability can be used for the amplification to help reduce the number of amplification errors that could be generated before the nucleic acid molecules have MITs attached. Furthermore, fewer cycles (e.g. between 2, 3, 4, and 5 cycles on the low end of the range and 3, 4, 5, 6, 7, 8, 9, or 10 on the high end of the range) of amplification cycles can be employed.

In some embodiments, the nucleic acid molecules in the sample can be fragmented to generate nucleic acid molecules of any chosen length before they are tagged with MITs. A skilled artisan will recognize methods for performing such fragmentation and the chosen lengths as discussed in more detail herein. For example, the nucleic acids can be fragmented using physical methods such as sonication, enzymatic methods such as digestion by DNase I or restriction endonucleases, or chemical methods such as applying heat in the presence of a divalent metal cation. Fragmentation can be performed such that a chosen size range of nucleic acid molecules are left as discussed in more detail herein. In other embodiments, nucleic acid molecules can be selected for specific size ranges using methods known in the art.

After fragmentation, the sample nucleic acid molecules can have 5' and/or 3' overhangs that need to be repaired before further library preparation. In some embodiments, before attaching MITs or other tags, the sample nucleic acid molecules with 5' and 3' overhangs can be repaired to generate blunt-ended sample nucleic acid molecules using methods known in the art. For example, in an appropriate buffer the polymerase and exonuclease activities of the Klenow Large Fragment Polymerase can be used to fill in 5' overhangs and remove 3' overhangs on the nucleic acid molecules. In some embodiments, a phosphate can be added on the 5' end of the repaired nucleic acid molecules using Polynucleotide Kinase (PNK) and reaction conditions a skilled artisan will understand. In further embodiments, a single nucleotide or multiple nucleotides can be added to one strand of a double stranded molecule to generate a "sticky end." For example, an adenosine (A) can be appended on the 3' ends of the nucleic acid molecules (A-tailing). In some embodiments, other sticky ends can be used other than an A overhang. In some embodiments, other adaptors can be added, for example looped ligation adaptors. In any of the embodiments disclosed herein, none, all, or any combination of these modifications can be carried out.

Many kits and methods are known in the art for generating libraries of nucleic acid molecules for subsequent sequencing. Kits especially adapted for preparing libraries from small nucleic acid fragments, especially circulating cell-free DNA, can be useful for practicing methods provided herein. For example, the NEXTflex Cell Free kits (Bioo Scientific, Austin, Tex.) or the Natera Library Prep Kit (Natera, San Carlos, Calif.). Such kits would typically be modified to include adaptors that are customized for the amplification and sequencing steps of the methods provided herein. Adaptor ligation can also be performed using commercially available kits such as the ligation kit found in the Agilent SureSelect kit (Agilent, Santa Clara, Calif.).

Sample nucleic acid molecules are composed of naturally occurring or non-naturally occurring ribonucleotides or deoxyribonucleotides linked through phosphodiester linkages. Furthermore, sample nucleic acid molecules are composed of a nucleic acid segment that is targeted for sequencing. Sample nucleic acid molecules can be or can include nucleic acid segments that are at least 20, 25, 50, 75, 100, 125, 150, 200, 250, 300, 400, 500, 600, 700, 800, 900, or 1,000 nucleotides in length. In any of the embodiments disclosed herein the sample nucleic acid molecules or nucleic acid segments can be between 1, 2, 3, 4, 5, 6, 7, 8, 9, 10, 11, 12, 13, 14, 15, 16, 17, 18, 19, 20, 25, 50, 75, 100, 125, 150, 200, 250, 300, 400, and 500 nucleotides in length on the low end of the range and 10, 11, 12, 13, 14, 15, 16, 17, 18, 19, 20, 25, 50, 75, 100, 125, 150, 200, 250, 300, 400, 500, 1,000, 2,000, 3,000, 4,000, 5,000, 6,000, 7,000, 8,000, 9,000, and 10,000 nucleotides in length on the high end of the range. In some embodiments, the nucleic acid molecules can be fragments of genomic DNA and can be between 1, 2, 3, 4, 5, 6, 7, 8, 9, 10, 11, 12, 13, 14, 15, 16, 17, 18, 19, 20, 25, 50, 75, 100, 125, 150, 200, 250, 300, 400, and 500 nucleotides in length on the low end of the range and 10, 11, 12, 13, 14, 15, 16, 17, 18, 19, 20, 25, 50, 75, 100, 125, 150, 200, 250, 300, 400, 500, 1,000, 2,000, 3,000, 4,000, 5,000, 6,000, 7,000, 8,000, 9,000, and 10,000 nucleotides in length on the high end of the range. For the sake of clarity, nucleic acids initially isolated from a living tissue, fluid, or cultured cells, can be much longer than sample nucleic acid molecules processed using methods herein. As discussed herein, for example, such initially isolated nucleic acid molecules can be fragmented to generate nucleic acid segments, before being used in the methods herein. In some embodiments, the nucleic acid molecules and nucleic acid segments can be identical. The sample nucleic acid molecule or sample nucleic acid segment can include a target locus that contains the nucleotide or nucleotides that are being queried, especially a single nucleotide polymorphism or single nucleotide variant. In any of the disclosed embodiments, the target loci can be at least 1, 2, 3, 4, 5, 6, 7, 8, 9, 10, 11, 12, 13, 14, 15, 16, 17, 18, 19, 20, 25, 50, 75, 100, 125, 150, 200, 250, 300, 400, 500, 600, 700, 800, 900, or 1,000 nucleotides in length and include a portion of or the entirety of the sample nucleic acid molecule and/or the sample nucleic acid segment. In other embodiments, the target loci can be between 1, 2, 3, 4, 5, 6, 7, 8, 9, 10, 11, 12, 13, 14, 15, 16, 17, 18, 19, 20, 25, 50, 75, 100, 125, 150, 200, 250, 300, 400, and 500 nucleotides in length on the low end of the range and 10, 11, 12, 13, 14, 15, 16, 17, 18, 19, 20, 25, 50, 75, 100, 125, 150, 200, 250, 300, 400, 500, 1,000, 2,000, 3,000, 4,000, 5,000, 6,000, 7,000, 8,000, 9,000, and 10,000 nucleotides in length on the high end of the range. In some embodiments, the target loci on different sample nucleic acid molecules can be at least 50%, 60%, 70%, 80%, 90% 95%, 96%, 97%, 98%, 99%, 99.9%, or 100% identical. In some embodiments, the target loci on different sample nucleic acid molecules can share at least 50%, 60%, 70%, 80%, 90% 95%, 96%, 97%, 98%, 99%, 99.9%, or 100% sequence identity.

In some embodiments, the entire sample nucleic acid molecule is a sample nucleic acid segment. For example, in certain embodiments where MITs are ligated directly to the ends of sample nucleic acid molecules, or ligated to a nucleic acid(s) ligated to the ends of sample nucleic acid molecules, or ligated as part of primers that bind to sequences at the termini of sample nucleic acid segments, or adapters, such as universal adapters added thereto, as discussed further herein, the entire nucleic acid molecule can be a sample nucleic acid segment. In other embodiments, for example certain embodiments where MITs are attached to sample nucleic acid molecules as part of primers that target binding sites internal to the termini of sample nucleic acid molecules, a portion of the sample nucleic acid molecule can be the sample nucleic acid segment that is targeted for downstream sequencing. For example, at least 50%, 60%, 70%, 75%, 80%, 85%, 90%, 95%, 96%, 97%, 98%, 99%, or 100% of a sample nucleic acid molecule can be a nucleic acid segment.

In some embodiments, sample nucleic acid molecules are a mixture of nucleic acids isolated from a natural source, some sample nucleic acid molecules having identical sequences, some having sequences sharing at least 50%, 60%, 70%, 80%, 90%, 95%, 98%, or 99% sequence identity, and some with less than 50%, 40%, 30%, 20%, 10%, or 5% sequence identity over between 20, 25, 50, 75, 100, 125, 150, 200, 250 nucleotides on the low end of the range, and 50, 75, 100, 125, 150, 200, 250, 300, 400, or 500 nucleotides on the high end of the range. Such sample nucleic acid molecules can be nucleic acid samples isolated form tissues or fluids of a mammal, such as a human, without enriching one sequence over another. In other embodiments, target sequences, for example, those from a gene of interest, can be enriched prior to performing methods provided herein.

In certain embodiments, some or all of the sample nucleic acid molecules in the population of nucleic acid molecules can have identical, or substantially identical nucleic acid segments. Nucleic acid molecules can be said to be substantially identical if the sequences of the nucleic acid segments share at least 90 percent sequence identity. Sample nucleic acid molecule, in certain illustrative examples, can share a nucleic acid segment having 90%, 91%, 92%, 93%, 94%, 95%, 96%, 97%, 98%, 99%, or 99.9% sequence identity over between 20, 25, 50, 75, 100, 125, 150, 200, 250 on the low end of the range, and 50, 75, 100, 125, 150, 200, 250, 300, 400, or 500 nucleic on the high end of the range. Methods provided herein are effective at distinguishing sample nucleic acid molecules that share at least 90%, 95%, 96%, 97%, 985, 99% or even 100% sequence identity in a sample.

In some embodiments, the 5' and 3' ends of nucleic acid segments adjacent to attached MITs can be used to aid in identifying and distinguishing sample nucleic acid molecules. Herein, these sequences are referred to as fragment-specific insert ends. After attachment of MITs as discussed elsewhere herein, the combination of MITs and fragment-specific insert ends can uniquely identify sample nucleic acid molecules as a sufficiently high ratio of MITs to sample nucleic acid molecules can be chosen such that the probability of two different sample nucleic acid molecules having identical fragment-specific insert ends and the same MIT(s) attached in the same orientation is exceedingly low. For example, such that there is less than a 1, 0.5, 0.1, 0.05, 0.01, 0.005, 0.001 or less probability. For example, using only MITs to identify each sample nucleic acid molecule from a set of 200 MITs gives 40,000 (200×200) possible combinations of identifiers. With the additional information provided using fragment-specific insert ends, the number of possible combinations can increase quickly. For example, including 2 nucleotides from the 5' and 3' fragment-specific insert ends in the identification of the nucleic acid molecules increases the 40,000 possible combinations to 10,240,000 possible combinations if each nucleotide is equally likely in the dinucleotide sequence. The lengths of the fragment-specific insert ends, when used in methods provided herein, can be between 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 nucleotides on the low end of the range and 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides on the high end of the range. In some embodiments, the fragment-specific ends used in combination with MITs to identify sample nucleic acid molecules are 1, 2, 3, or 4 nucleotides in length.

In further embodiments, the determined sequences of the fragment-specific insert ends can be used to map each end of the nucleic acid molecule to specific locations in the genome (i.e. genome coordinates) of the organism from which the sample was isolated. The mapped locations provide another identifier for each of the tagged nucleic acid molecules. Mapping each end greatly increases the number of identifiers available for each tagged nucleic acid molecule. In these embodiments, the mapped location of each end of the nucleic acid molecule can be used in combination with the MITs to identify the individual sample nucleic acid molecules that gave rise to the tagged nucleic acid molecules. For instance, for a given target base in mononucleosomal circulating cell-free DNA (cfDNA), the 5'-side fragment end can be anywhere between about 0 to 199 bases upstream. Likewise, the 3'-side fragment end can be 0-199 bases downstream. Theoretically this could give 40,000 possible end combinations. In reality, most molecules are between 100-200 bases in total length so the total number of possible combinations end up being around 15,000 (maximum, but not all combinations occur at equal likelihood). This would mean 40,000 MIT combos×15,000 possible fragment ends=600,000,000 possible end combinations. Furthermore, if a nucleic acid segment is mapped to the genome a mutation in that segment or an allele of that segment can be identified.

The total number of sample nucleic acid molecules can vary greatly depending on the sample source and preparation as well as the needs of the method. For example, the total sample nucleic acid molecules can be between $1\times10^{10}$, $2\times10^{10}$, $2.5\times10^{10}$, $5\times10^{10}$ and $1\times10^{11}$ on the low end of the range and $5\times10^{10}$, $1\times10^{11}$, $2\times10^{11}$, $2.5\times10^{11}$, $5\times10^{11}$, $1\times10^{12}$, $2\times10^{12}$, $2.5\times10^{12}$, $5\times10^{12}$, and $1\times10^{13}$ nucleic acid molecules on the high end of the range. For example, 10,000 copies of the genome from human circulating cell-free DNA could be composed of $2\times10^{11}$ total sample nucleic acid molecules since mononucleosomal cfDNA is approximately 100 to 200 bp nucleic acid fragments that have highly variable fragmentation patterns (3,000,000,000 bp/genome copy×10,000 genome copies/150 bp/sample nucleic acid molecule=$2\times10^{11}$ sample nucleic acid molecules).

In some embodiments, provided herein, the total number of sample nucleic acid molecules can include between 50, 100, 200, 250, 500, 750, 1,000, 2,000, 2,500, 5,000, and 10,000 copies of the human genome on the low end of the range, and 1,000, 2,000, 2,5000, 5,000, 10,000, 20,000, 25,000, 50,000, and 100,000 copies of the human genome on the high end of the range. In other embodiments, the total number of sample nucleic acid molecules is the number of nucleic acid molecules of between 100 and 500 nucleotides in length, for example, 200 nucleotides in 1, 2, 2.5, 3, 4, or 5 nM on the low end and 2.5, 3, 4, 5, 10, 20 or 25 nM of cfDNA on the high end of the range.

Diversity of a set or a population of nucleic acid molecules is the number of unique sequences among the nucleic acid molecules in the set or population. The diversity of sample nucleic acid molecules is the number of unique sequences among sample nucleic acid molecules. It is common to have more than 1 copy of an identical or near identical nucleic acid sequence in a sample even when nucleic acid molecules in a sample have not been subjected to amplification. Current nucleic acid sample preparation and DNA isolation procedures typically result in many copies of every nucleic acid molecule in the sample.

In any of the embodiments disclosed herein the diversity of nucleotide sequences of the sample nucleic acid molecules in the population can be between 100, 1,000, 10,000, $1\times10^5$ $1\times10^6$, and $1\times10^7$ different nucleic acid sequences on the low end of the range, and $1\times10^5$ $1\times10^6$, and $1\times10^7$, $1\times10^8$, $1\times10^9$, and $1\times10^{10}$ different nucleotide sequences on the high end of the range. In some embodiments, the diversity of nucleotide sequences in the population of sample nucleic acid molecules is between $1\times10^6$, $5\times10^6$, and $1\times10^7$ different nucleic acid sequences on the low end of the range, and $1\times10^7$, $1\times10^8$, $1\times10^9$, and $1\times10^{10}$, different nucleotide sequences on the high end of the range.

For a human cfDNA sample, since there are about 3 billion nucleotides in the human genome, since the nucleic acid fragment size is about 150 nucleotides, and since the fragmentation pattern is not random but not fixed either, there are between about 20 million (3 billion/150) and about 3 billion different nucleic acid fragments in a human cfDNA sample. Accordingly, in some embodiments, the sample is a human cfDNA sample, such as, for example, a purified sample, or a serum or plasma sample, and the diversity of the sample is between 20 million and 3 billion.

Sample nucleic acid molecules can be of approximately the same length in certain embodiments of the present disclosure. For example, the sample nucleic acid molecules can be about 200 nucleotides, for example for circulating cell-free DNA samples, or between 50, 75, 100, 125 or 150 nucleotides on the low end of the range and 150, 200, 250, or 300 nucleotides in length on the high end for certain samples, for example blood, sera, or plasma samples that include circulating cell-free DNA.

In other embodiments, sample nucleic acid molecules can be different ranges of starting lengths. The lengths of the sample nucleic acid molecules with or without fragmentation can be any size appropriate for the subsequent method steps. For example, sample nucleic acid molecules can be between at least 10, 11, 12, 13, 14, 15, 16, 17, 18, 19, 20, 21, 22, 23, 24, 25, 30, 35, 40, 45, 50, 60, 70, 80, 90, 100, 125, 150, 175, 200, 250, 300, 350, 400, 450, 500, 600, 700, 800, 900, 1,000, 1,250, 1,500, 1,750, 2,000, 2,500, 3,000, 4,000, 5,000, 6,000, 7,000, 8,000, 9,000, and 10,000 nucleotides on the low end and 15, 16, 17, 18, 19, 20, 21, 22, 23, 24, 25, 30, 35, 40, 45, 50, 60, 70, 80, 90, 100, 125, 150, 175, 200, 250, 300, 350, 400, 450, 500, 600, 700, 800, 900, 1,000, 1,250, 1,500, 1,750, 2,000, 2,500, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 25,000, 30,000, 40,000, 50,000, 60,000, 70,000, 80,000, 90,000, and 100,000 nucleotides on the high end.

In certain respects, the chosen size range of starting lengths of the sample nucleic acid segments molecules is dependent on the method of attachment. Longer ranges of nucleic acid molecule lengths are chosen if PCR is used as they increase the probability of two primers binding to the same nucleic acid molecule. Shorter ranges of nucleic acid molecule lengths are chosen if ligation is used as they reduce the length of the amplicons generated by PCR in later steps in the method, especially if PCR is performed using universal primers that bind outside the nucleic acid segments. Therefore, when using ligation to attach the MITs, the sample nucleic acid molecules will generally be shorter than when using PCR to attach the MITs. For example, in some embodiments, the sample nucleic acid molecules are between 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250, 300, 350, 400, 450, 500, 600, 700, 800, 900, and 1,000 nucleotides on the low end and 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 4,000, 5,000, 6,000, 7,000, 8,000, 9,000, and 10,000 nucleotides on the high end and the MITs are attached by ligation. In certain embodiments, the sample nucleic acid molecules are between 50, 55, 60, 65, 70, 75, 80, 85, 90, 95, 100, 110, 120, 130, 140, 150, 160, 170, 180, 190, 200, 225, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 4,000, 5,000, 6,000, 7,000, 8,000, 9,000, and 10,000 nucleotides on the low end and 100, 110, 120, 130, 140, 150, 160, 170, 180, 190, 200, 225, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 25,000, 30,000, 40,000, 50,000, 60,000, 70,000, 80,000, 90,000, and 100,000 nucleotides on the high end and the MITs are attached by PCR.

In some embodiments, the nucleic acid molecules in the sample can be synthesized using a machine. In some embodiments, the nucleic acid molecules are generated by a living cell. In some embodiments, nucleic acid molecules generated by a living cell and nucleic acid molecules synthesized using a machine can be combined and used as the sample nucleic acid molecules. This combination may be beneficial for quantitation purposes. In some embodiments, the sample nucleic acid molecules have not been amplified in vitro.

MITs and MIT Reaction Mixtures

The step of attaching MITs to sample nucleic acid molecules or nucleic acid segments in methods provided herein, typically includes forming a reaction mixture. The reaction mixtures formed during such methods can themselves be individual aspects of the present disclosure. Reaction mixtures provided herein can include sample nucleic acid molecules, as disclosed in detail herein, and a set of MITs, as disclosed in detail herein, wherein the total number of nucleic acid molecules in the sample is greater than the diversity of MITs in the set of MITs. In some embodiments, the total number of nucleic acid molecules in the sample is also greater than the diversity of possible combinations of attached MITs.

In some embodiments disclosed herein, the ratio of the total number of the sample nucleic acid molecules to the diversity of the MITs in the set of MITs or the diversity of the possible combinations of attached MITs using the set of MITs can be between 10:1, 20:1, 30:1, 40:1, 50:1, 60:1, 70:1, 80:1, 90:1, 100:1 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 15,000:1, 20,000:1, 25,000:1, 30,000:1, 40,000:1, 50,000:1, 60,000:1, 70,000:1, 80,000:1, 90,000:1, 100,000:1, 200,000:1, 300,000:1, 400,000:1, 500,000:1, 600,000:1, 700,000:1, 800,000:1, 900,000:1, and 1,000,000:1 on the low end of the range and 100:1 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 15,000:1, 20,000:1, 25,000:1, 30,000:1, 40,000:1, 50,000:1, 60,000:1, 70,000:1, 80,000:1, 90,000:1, 100,000:1, 200,000:1, 300,000:1, 400,000:1, 500,000:1, 600,000:1, 700,000:1, 800,000:1, 900,000:1, 1,000,000:1, 2,000,000:1, 3,000,000:1, 4,000,000:1, 5,000,000:1, 6,000,000:1, 7,000,000:1, 8,000,000:1, 9,000,000:1, 10,000,000:1, 50,000,000:1, 100,000,000:1, and 1,000,000,000:1 on the high end of the range.

In some embodiments, the sample is a human cfDNA sample. In such a method, as disclosed herein, the diversity is between about 20 million and about 3 billion. In these embodiments, the ratio of the total number of sample nucleic acid molecules to the diversity of the set of MITs can be between 100,000:1, $1 \times 10^6$:1, $1 \times 10^7$:1, $2 \times 10^7$:1, and $2.5 \times 10^7$:1 on the low end of the range and $2 \times 10^7$:1, $2.5 \times 10^7$:1, $5 \times 10^7$:1, $1 \times 10^8$:1, $2.5 \times 10^8$:1, $5 \times 10^8$:1, and $1 \times 10^9$:1 on the high end of the range.

In some embodiments, the diversity of possible combinations of attached MITs using the set of MITs is preferably greater than the total number of sample nucleic acid molecules that span a target locus. For example, if there are 100 copies of the human genome that have all been fragmented into 200 bp fragments such that there are approximately 15,000,000 fragments for each genome, then it is preferable that the diversity of possible combinations of MITs be greater than 100 (number of copies of each target locus) but less than 1,500,000,000 (total number of nucleic acid molecules). For example, the diversity of possible combinations of MITs can be greater than 100 but much less than 1,500,000,000, such as 200, 300, 400, 500, 600, 700, 800, 900, or 1,000 possible combinations of attached MITs. While the diversity of MITs in the set of MITs is less than the total number of nucleic acid molecules, the total number of MITs in the reaction mixture is in excess of the total number of nucleic acid molecules or nucleic acid molecule segments in the reaction mixture. For example, if there are 1,500,000,000 total nucleic acid molecules or nucleic acid molecule segments, then there will be more than 1,500,000,000 total MIT molecules in the reaction mixture. In some embodiments, the ratio of the diversity of MITs in the set of MITs can be lower than the number of nucleic acid molecules in a sample that span a target locus while the diversity of the possible combinations of attached MITs using the set of MITs can be greater than the number of nucleic acid molecules in the sample that span a target locus. For example, the ratio of the number of nucleic acid molecules in a sample that span a target locus to the diversity of MITs in the set of MITs can be at least 10:1, 25:1, 50:1, 100:1, 125:1, 150:1, or 200:1 and the ratio of the diversity of the possible combinations of attached MITs using the set of MITs to the number of nucleic acid molecules in the sample that span a target locus can be at least 1.01:1, 1.1:1, 2:1, 3:1, 4:1, 5:1, 6:1, 7:1, 8:1, 9:1, 10:1, 20:1, 25:1, 50:1, 100:1, 250:1, 500:1, or 1,000:1.

Typically, the diversity of MITs in the set of MITs is less than the total number of sample nucleic acid molecules that span a target locus whereas the diversity of the possible combinations of attached MITs is greater than the total number of sample nucleic acid molecules that span a target locus. In embodiments where 2 MITs are attached to sample nucleic acid molecules, the diversity of MITs in the set of MITs is less than the total number of sample nucleic acid molecules that span a target locus but greater than the square root of the total number of sample nucleic acid molecules that span a target locus. In some embodiments, the diversity of MITs is less than the total number of sample nucleic acid molecules that span a target locus but 1, 2, 3, 4, or 5 more than the square root of the total number of sample nucleic acid molecules that span a target locus. Thus, although the diversity of MITs is less than the total number of sample nucleic acid molecules that span a target locus, the total number of combinations of any 2 MITs is greater than the total number of sample nucleic acid molecules that span a target locus. The diversity of MITs in the set is typically less than one half the number of sample nucleic acid molecules than span a target locus in samples with at least 100 copies of each target locus. In some embodiments, the diversity of MITs in the set can be at least 1, 2, 3, 4, or 5 more than the square root of the total number of sample nucleic acid molecules that span a target locus but less than $\frac{1}{5}$, $\frac{1}{10}$, $\frac{1}{20}$, $\frac{1}{50}$, or $\frac{1}{100}$ the total number of sample nucleic acid molecules that span a target locus. For samples with between 2,000 and 1,000,000 sample nucleic acid molecules that span a target locus, the number of MITs in the set does not exceed 1,000. For example, in a sample with 10,000 copies of the genome in a genomic DNA sample such as a circulating cell-free DNA sample such that the sample has 10,000 sample nucleic acid molecules that span a target locus, the diversity of MITs can be between 101 and 1,000, or between 101 and 500, or between 101 and 250. In some embodiments, the diversity of MITs in the set of MITs can be between the square root of the total number of sample nucleic acid molecules that span a target locus and 1, 10, 25, 50, 100, 125, 150, 200, 250, 300, 400, 500, 600, 700, 800, 900, or 1,000 less than the total number of sample nucleic acid molecules that span a target locus. In some embodiments, the diversity of MITs in the set of MITs can be between 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, and 80% of the number of sample nucleic acid molecules that span a target locus on the low end of the range and 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, and 99% of the number of sample nucleic acid molecules that span a target locus on the high end of the range.

In some embodiments, the ratio of the total number of MITs in the reaction mixture to the total number of sample nucleic acid molecules in the reaction mixture can be between 1.01, 1.1:1, 2:1, 3:1, 4:1, 5:1, 6:1, 7:1, 8:1, 9:1, 10:1, 25:1 50:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, and 10,000:1 on the low end of the range and 25:150:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 15,000:1, 20,000:1, 25,000:1, 30,000:1, 40,000:1, and 50,000:1 on the high end of the range. In some embodiments, the total number of MITs in the reaction mixture is at least 50%, 60%, 70%, 80%, 90%, 95%, 96%, 97%, 98% 99%, or 99.9% of the total number of sample nucleic acid molecules in the reaction mixture. In other embodiments, the ratio of the total number of MITs in the reaction mixture to the total number of sample nucleic acid molecules in the reaction mixture can be at least enough MITs for each sample nucleic acid molecule to have the appropriate number of MITs attached, i.e. 2:1 for 2 MITs being attached, 3:1 for 3 MITs, 4:1 for 4 MITs, 5:1 for 5 MITs, 6:1 for 6 MITs, 7:1 for 7 MITs, 8:1 for 8 MITs, 9:1 for 0 MITs, and 10:1 for 10 MITs.

In some embodiments, the ratio of the total number of MITs with identical sequences in the reaction mixture to the total number of nucleic acid segments in the reaction mixture can be between 0.1:1, 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.25:1, 2.5:1, 2.75:1, 3:1, 3.5:1, 4:1, 4.5:1, and 5:1 on the low end of the range and 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.25:1, 2.5:1, 2.75:1, 3:1, 3.5:1, 4:1, 4.5:1, 5:1, 6:1, 7:1, 8:1, 9:1, 10:1, 20:1, 30:1, 40:1, 50:1, 60:1, 70:1, 80:1, 90:1, and 100:1 on the high end of the range.

The set of MITs can include, for example, at least three MITs or between 10 and 500 MITs. As discussed herein in some embodiments, nucleic acid molecules from the sample are added directly to the attachment reaction mixture without amplification. These sample nucleic acid molecules can be purified from a source, such as a living cell or organism, as disclosed herein, and then MITs can be attached without amplifying the nucleic acid molecules. In some embodiments, the sample nucleic acid molecules or nucleic acid segments can be amplified before attaching MITs. As discussed herein, in some embodiments, the nucleic acid molecules from the sample can be fragmented to generate sample nucleic acid segments. In some embodiments, other oligonucleotide sequences can be attached (e.g. ligated) to the ends of the sample nucleic acid molecules before the MITs are attached.

In some embodiments disclosed herein the ratio of sample nucleic acid molecules, nucleic acid segments, or fragments that include a target locus to MITs in the reaction mixture can be between 1.01:1, 1.05, 1.1:1, 1.2:1 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 15:1, 20:1, 25:1, 30:1, 35:1, 40:1, 45:1, and 50:1 on the low end and 5:1, 6:1, 7:1, 8:1, 9:1, 10:1, 15:1, 20:1, 25:1, 30:1, 35:1, 40:1, 45:1, 50:1 60:1, 70:1, 80:1, 90:1, 100:1, 125:1, 150:1, 175:1, 200:1, 300:1, 400:1 and 500:1 on the high end. For example, in some embodiments, the ratio of sample nucleic acid molecules, nucleic acid segments, or fragments with a specific target locus to MITs in the reaction mixture is between 5:1, 6:1, 7:1, 8:1, 9:1, 10:1, 15:1, 20:1, 25:1, 30:1, 35:1, 40:1, 45:1, and 50:1 on the low end and 20:1, 25:1, 30:1, 35:1, 40:1, 45:1, 50:1, 60:1, 70:1, 80:1, 90:1, 100:1, and 200:1 on the high end. In some embodiments, the ratio of sample nucleic acid molecules or nucleic acid segments to MITs in the reaction mixture can be between 25:1, 30:1, 35:1, 40:1, 45:1, 50:1 on the low end and 50:1 60:1, 70:1, 80:1, 90:1, 100:1 on the high end. In some embodiments, the diversity of the possible combinations of attached MITs can be greater than the number of sample nucleic acid molecules, nucleic acid segments, or fragments that span a target locus. For example, in some embodiments, the ratio of the diversity of the possible combinations of attached MITs to the number of sample nucleic acid molecules, nucleic acid segments, or fragments that span a target locus can be at least 1.01, 1.1:1, 2:1, 3:1, 4:1, 5:1, 6:1, 7:1, 8:1, 9:1, 10:1, 20:1, 25:1, 50:1, 100:1, 250:1, 500:1, or 1,000:1.

Reaction mixtures for tagging nucleic acid molecules with MITs (i.e. attaching nucleic acid molecules to MITs), as provided herein, can include additional reagents in addition to a population of sample nucleic acid molecules and a set of MITs. For example, the reaction mixtures for tagging can include a ligase or polymerase with suitable buffers at an appropriate pH, adenosine triphosphate (ATP) for ATP-dependent ligases or nicotinamide adenine dinucleotide for NAD-dependent ligases, deoxynucleoside triphosphates (dNTPs) for polymerases, and optionally molecular crowding reagents such as polyethylene glycol. In certain embodiments the reaction mixture can include a population of sample nucleic acid molecules, a set of MITs, and a polymerase or ligase, wherein the ratio of the number of sample nucleic acid molecules, nucleic acid segments, or fragments with a specific target locus to the number of MITs in the reaction mixture can be any of the ratios disclosed herein, for example between 2:1 and 100:1, or between 10:1 and 100:1 or between 25:1 and 75:1, or is between 40:1 and 60:1, or between 45:1 and 55:1, or between 49:1 and 51:1.

In some embodiments disclosed herein the number of different MITs (i.e. diversity) in the set of MITs can be between 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 350, 400, 450, 500, 600, 700, 800, 900, 1,000, 1,500, 2,000, 2,500, and 3,000 MITs with different sequences on the low end and 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 350, 400, 450, 500, 600, 700, 800, 900, 1,000, 2,000, 3,000, 4,000, and 5,000 MITs with different sequences on the high end. For example, the diversity of different MITs in the set of MITs can be between 20, 25, 30, 35, 40, 45, 50, 60, 70, 80, 90, and 100 different MIT sequences on the low end and 50, 60, 70, 80, 90, 100, 125, 150, 175, 200, 250, and 300 different MIT sequences on the high end. In some embodiments, the diversity of different MITs in the set of MITs can be between 50, 60, 70, 80, 90, 100, 125, and 150 different MIT sequences on the low end and 100, 125, 150, 175, 200, and 250 different MIT sequences on the high end. In some embodiments, the diversity of different MITs in the set of MITs can be between 3 and 1,000, or 10 and 500, or 50 and 250 different MIT sequences. In some embodiments, the diversity of possible combinations of attached MITs using the set of MITs can be between 4, 5, 6, 7, 8, 9, 10, 15, 20, 25, 30, 40, 50, 75, 100, 150, 200, 250, 300, 400, 500, and 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 250,000, 500,000, 1,000,000, possible combinations of attached MITs on the low end of the range and 10, 15, 20, 25, 30, 40, 50, 75, 100, 150, 200, 250, 300, 400, 500, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 250,000, 500,000, 1,000,000, 2,000,000, 3,000,000, 4,000,000, 5,000,000, 6,000,000, 7,000,000, 8,000,000, 9,000,000, and 10,000,000 possible combinations of attached MITs on the high end of the range.

The MITs in the set of MITs are typically all the same length. For example, in some embodiments, the MITs can be any length between 2, 3, 4, 5, 6, 7, 8, 9, 10, 11, 12, 13, 14, 15, 16, 17, 18, 19, and 20 nucleotides on the low end and 4, 5, 6, 7, 8, 9, 10, 11, 12, 13, 14, 15, 16, 17, 18, 19, 20, 21, 22, 23, 24, 25, 26, 27, 28, 29, and 30 nucleotides on the high end. In certain embodiments, the MITs are any length between 3, 4, 5, 6, 7, or 8 nucleotides on the low end and 5, 6, 7, 8, 9, 10, or 11 nucleotides on the high end. In some embodiments, the lengths of the MITs can be any length between 4, 5, or 6, nucleotides on the low end and 5, 6, or 7 nucleotides on the high end. In some embodiments, the length of the MITs is 5, 6, or 7 nucleotides.

As will be understood, a set of MITs typically includes many identical copies of each MIT member of the set. In some embodiments, a set of MITs includes between 10, 20, 25, 30, 40, 50, 100, 500, 1,000, 10,000, 50,000, and 100,000 times more copies on the low end of the range, and 100, 500, 1,000, 10,000, 50,000, 100,000, 250,000, 500,000 and 1,000,000 more copies on the high end of the range, than the total number of sample nucleic acid molecules that span a target locus. For example, in a human circulating cell-free DNA sample isolated from plasma, there can be a quantity of DNA fragments that includes, for example, 1,000-100,000 circulating fragments that span any target locus of the genome. In certain embodiments, there are no more than 1/10, 1/4, 1/2, or 3/4 as many copies of any given MIT as total unique MITs in a set of MITs. Between members of the set, there can be 1, 2, 3, 4, 5, 6, 7, 8, 9, or 10 differences between any sequence and the rest of the sequences. In some embodiments, the sequence of each MIT in the set differs from all the other MITs by at least 1, 2, 3, 4, 5, 6, 7, 8, 9, or 10 nucleotides. To reduce the chance of misidentifying an MIT, the set of MITs can be designed using methods a skilled artisan will recognize, such as taking into consideration the Hamming distances between all the MITs in the set of MITs. The Hamming distance measures the minimum number of substitutions required to change one string, or nucleotide sequence, into another. Here, the Hamming distance measures the minimum number of amplification errors required to transform one MIT sequence in a set into another MIT sequence from the same set. In certain embodiments, different MITs of the set of MITs have a Hamming distance of less than 1, 2, 3, 4, 5, 6, 7, 8, 9, or 10 between each other.

In certain embodiments, a set of isolated MITs as provided herein is one embodiment of the present disclosure. The set of isolated MITs can be a set of single stranded, or partially, or fully double stranded nucleic acid molecules, wherein each MIT is a portion of, or the entire, nucleic acid molecule of the set. In certain examples, provided herein is a set of Y-adapter (i.e. partially double-stranded) nucleic acids that each include a different MIT. The set of Y-adapter nucleic acids can each be identical except for the MIT portion. Multiple copies of the same Y-adapter MIT can be included in the set. The set can have a number and diversity of nucleic acid molecules as disclosed herein for a set of MITs. As a non-limiting example, the set can include 2, 5, 10, or 100 copies of between 50 and 500 MIT-containing Y-adapters, with each MIT segment between 4 and 8 nucleic acids in length and each MIT segment differing from the other MIT segments by at least 2 nucleotides, but contain identical sequences other than the MIT sequence. Further details regarding Y-adapter portion of the set of Y-adapters is provided herein.

In other embodiments, a reaction mixture that includes a set of MITs and a population of sample nucleic acid molecules is one embodiment of the present disclosure. Furthermore, such a composition can be part of numerous methods and other compositions provided herein. For example, in further embodiments, a reaction mixture can include a polymerase or ligase, appropriate buffers, and supplemental components as discussed in more detail herein. For any of these embodiments, the set of MITs can include between 25, 50, 100, 200, 250, 300, 400, 500, or 1,000 MITs on the low end of the range, and 100, 200, 250, 300, 400, 500, 1,000, 1,500, 2,000, 2,500, 5,000, 10,000, or 25,000 MITs on the high end of the range. For example, in some embodiments, a reaction mixture includes a set of between 10 and 500 MITs.

Attaching the MITs

Molecular Index Tags (MITs) as discussed in more detail herein can be attached to sample nucleic acid molecules in the reaction mixture using methods that a skilled artisan will recognize. In some embodiments, the MITs can be attached alone, or without any additional oligonucleotide sequences. In some embodiments, the MITs can be part of a larger oligonucleotide that can further include other nucleotide sequences as discussed in more detail herein. For example, the oligonucleotide can also include primers specific for nucleic acid segments or universal primer binding sites, adapters such as sequencing adapters such as Y-adapters, library tags, ligation adapter tags, and combinations thereof. A skilled artisan will recognize how to incorporate various tags into oligonucleotides to generate tagged nucleic acid molecules useful for sequencing, especially high-throughput sequencing. The MITs of the present disclosure are advantageous in that they are more readily used with additional sequences, such as Y-adapter and/or universal sequences because the diversity of nucleic acid molecules is less, and therefore they can be more easily combined with additional sequences on an adapter to yield a smaller, and therefore more cost effective set of MIT-containing adapters.

In some embodiments, the MITs are attached such that one MIT is 5' to the sample nucleic acid segment and one MIT is 3' to the sample nucleic acid segment in the tagged nucleic acid molecule. For example, in some embodiments, the MITs can be attached directly to the 5' and 3' ends of the sample nucleic acid molecules using ligation. In some embodiments disclosed herein, ligation typically involves forming a reaction mixture with appropriate buffers, ions, and a suitable pH in which the population of sample nucleic acid molecules, the set of MITs, adenosine triphosphate, and a ligase are combined. A skilled artisan will understand how to form the reaction mixture and the various ligases available for use. In some embodiments, the nucleic acid molecules can have 3' adenosine overhangs and the MITs can be located on double-stranded oligonucleotides having 5' thymidine overhangs, such as directly adjacent to a 5' thymidine.

In further embodiments, MITs provided herein can be included as part of Y-adapters before they are ligated to sample nucleic acid molecules. Y-adapters are well-known in the art and are used, for example, to more effectively provide primer binding sequences to the two ends of the nucleic acid molecules before high-throughput sequencing. Y-adapters are formed by annealing a first oligonucleotide and a second oligonucleotide where a 5' segment of the first oligonucleotide and a 3' segment of the second oligonucleotide are complementary and wherein a 3' segment of the first oligonucleotide and a 5' segment of the second oligonucleotide are not complementary. In some embodiments, Y-adapters include a base-paired, double-stranded polynucleotide segment and an unpaired, single-stranded polynucleotide segment distal to the site of ligation. The double-stranded polynucleotide segment can be between 3, 4, 5, 6, 7, 8, 9, 10, 11, 12, 13, 14, 15, 16, 17, 18, 19, or 20 nucleotides in length on the low end of the range and 4, 5, 6, 7, 8, 9, 10, 11, 12, 13, 14, 15, 16, 17, 18, 19, 20, 21, 22, 23, 24, 25, 26, 27, 28, 29, and 30 nucleotides in length on the high end of the range. The single-stranded polynucleotide segments on the first and second oligonucleotides can be between 3, 4, 5, 6, 7, 8, 9, 10, 11, 12, 13, 14, 15, 16, 17, 18, 19, or 20 nucleotides in length on the low end of the range and 4, 5, 6, 7, 8, 9, 10, 11, 12, 13, 14, 15, 16, 17, 18, 19, 20, 21, 22, 23, 24, 25, 26, 27, 28, 29, and 30 nucleotides in length on the high end of the range. In these embodiments, MITs are typically double stranded sequences added to the ends of Y-adapters, which are ligated to sample nucleic acid segments to be sequenced. Exemplary Y-adapters are illustrated in FIG. 1. In some embodiments, the non-complementary segments of the first and second oligonucleotides can be different lengths.

In some embodiments, double-stranded MITs attached by ligation will have the same MIT on both strands of the sample nucleic acid molecule. In certain respects the tagged nucleic acid molecules derived from these two strands will be identified and used to generate paired MIT families. In downstream sequencing reactions, where single stranded nucleic acids are typically sequenced, an MIT family can be identified by identifying tagged nucleic acid molecules with identical or complementary MIT sequences. In these embodiments, the paired MIT families can be used to verify the presence of sequence differences in the initial sample nucleic acid molecule as discussed herein.

Figure 2:
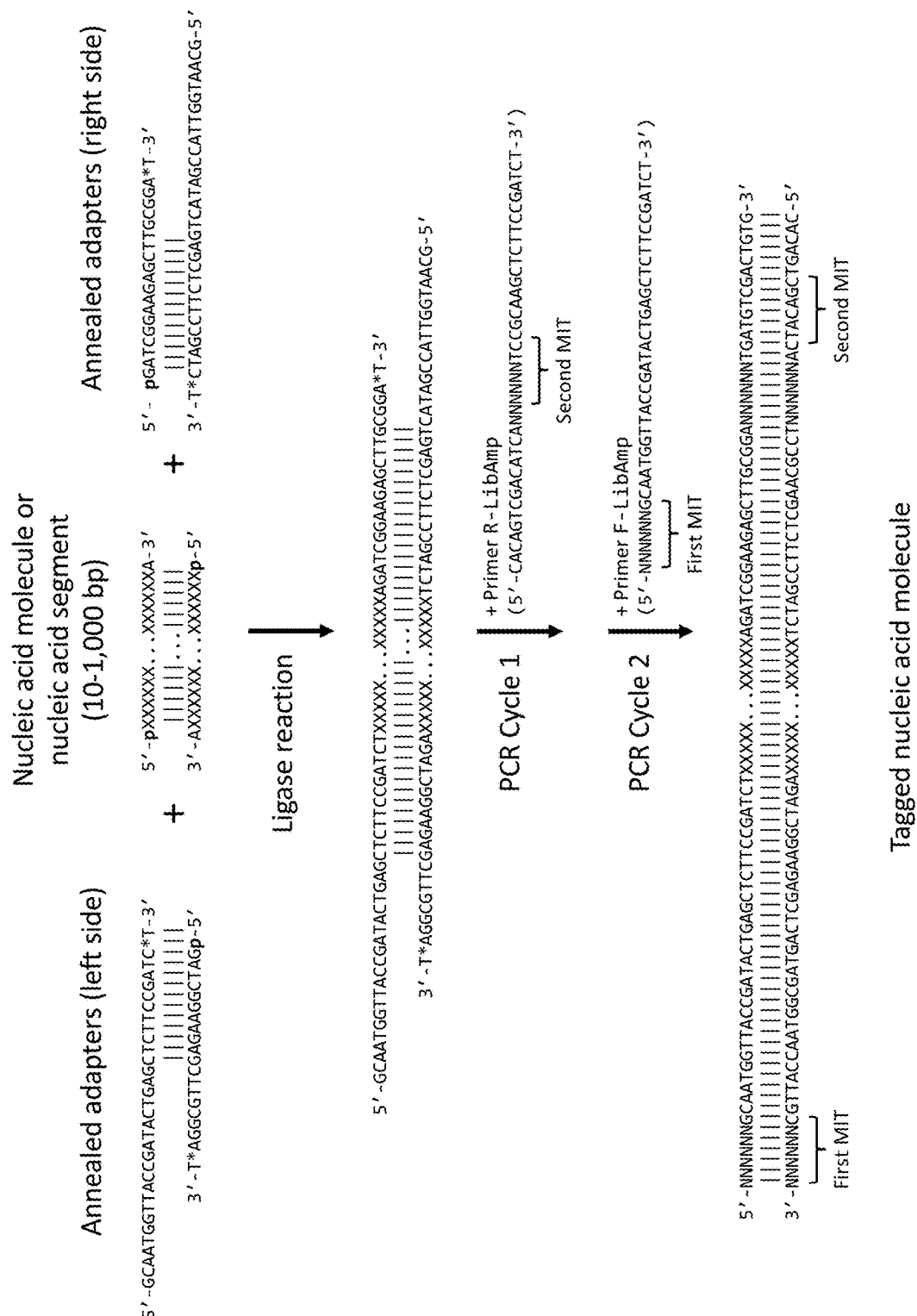
FIG. 2 is a schematic showing the incorporation of two MITs into a nucleic acid molecule or nucleic acid segment using PCR with primers containing the MIT sequences.

In some embodiments, as illustrated in FIG. 2, MITs can be attached to the sample nucleic acid segment by being incorporated 5' to forward and/or reverse PCR primers that bind sequences in the sample nucleic acid segment. In some embodiments, the MITs can be incorporated into universal forward and/or reverse PCR primers that bind universal primer binding sequences previously attached to the sample nucleic acid molecules. In some embodiments, the MITs can be attached using a combination of a universal forward or reverse primer with a 5' MIT sequence and a forward or reverse PCR primer that bind internal binding sequences in the sample nucleic acid segment with a 5' MIT sequence. After 2 cycles of PCR, sample nucleic acid molecules that have been amplified using both the forward and reverse primers with incorporated MIT sequences will have MITs attached 5' to the sample nucleic acid segments and 3' to the sample nucleic acid segments in each of the tagged nucleic acid molecules. In some embodiments, the PCR is done for 2, 3, 4, 5, 6, 7, 8, 9, or 10 cycles in the attachment step.

In some embodiments disclosed herein the two MITs on each tagged nucleic acid molecule can be attached using similar techniques such that both MITs are 5' to the sample nucleic acid segments or both MITs are 3' to the sample nucleic acid segments. For example, two MITs can be incorporated into the same oligonucleotide and ligated on one end of the sample nucleic acid molecule or two MITs can be present on the forward or reverse primer and the paired reverse or forward primer can have zero MITs. In other embodiments, more than two MITs can be attached with any combination of MITs attached to the 5' and/or 3' locations relative to the nucleic acid segments.

As discussed herein, other sequences can be attached to the sample nucleic acid molecules before, after, during, or with the MITs. For example, ligation adapters, often referred to as library tags or ligation adaptor tags (LTs), appended, with or without a universal primer binding sequence to be used in a subsequent universal amplification step. In some embodiments, the length of the oligonucleotide containing the MITs and other sequences can be between 5, 6, 7, 8, 9, 10, 11, 12, 13, 14, 15, 16, 17, 18, 29, 20, 21, 22, 23, 24, 25, 26, 27, 28, 29, 30, 35, 40, 45, 50, 55, 60, 65, 70, 75, 80, 85, 90, 95, and 100 nucleotides on the low end of the range and 10, 11, 12, 13, 14, 15, 16, 17, 18, 29, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, and 200 nucleotides on the high end of the range. In certain respects the number of nucleotides in the MIT sequences can be a percentage of the number of nucleotides in the total sequence of the oligonucleotides that include MITs. For example, in some embodiments, the MIT can be at most 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of the total nucleotides of an oligonucleotide that is ligated to a sample nucleic acid molecule.

After attaching MITs to the sample nucleic acid molecules through a ligation or PCR reaction, it may be necessary to clean up the reaction mixture to remove undesirable components that could affect subsequent method steps. In some embodiments, the sample nucleic acid molecules can be purified away from the primers or ligases. In other embodiments, the proteins and primers can be digested with proteases and exonucleases using methods known in the art.

After attaching MITs to the sample nucleic acid molecules, a population of tagged nucleic acid molecules is generated, itself forming embodiments of the present disclosure. In some embodiments, the size ranges of the tagged nucleic acid molecules can be between 10, 20, 30, 40, 50, 60, 70, 80, 90, 100, 125, 150, 175, 200, 250, 300, 400, and 500 nucleotides on the low end of the range and 100, 125, 150, 175, 200, 250, 300, 400, 500, 600, 700, 800, 900, 1,000, 2,000, 3,000, 4,000, and 5,000 nucleotides on the high end of the range.

Such a population of tagged nucleic acid molecules can include between 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250, 300, 350, 400, 450, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 100,000, 200,000, 300,000, 400,000, 500,000, 600,000, 700,000, 800,000, 900,000, 1,000,000, 1,250,000, 1,500,000, 2,000,000, 2,500,000, 3,000,000, 4,000,000, 5,000,000, 10,000,000, 20,000,000, 30,000,000, 40,00,000, 50,000,000, 50,000,000, 100,000,000, 200,000,000, 300,000,000, 400,000,000, 500,000,000, 600,000,000, 700,000,000, 800,000,000, 900,000,000, and 1,000,000,000 tagged nucleic acid molecules on the low end of the range and 10, 15, 20, 25, 30, 40, 50, 60, 70, 80, 90, 100, 150, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 100,000, 200,000, 300,000, 400,000, 500,000, 600,000, 700,000, 800,000, 900,000, 1,000,000, 1,250,000, 1,500,000, 2,000,000, 2,500,000, 3,000,000, 4,000,000, 5,000,000, 6,000,000, 7,000,000, 8,000,000, 9,000,000, 10,000,000, 20,000,000, 30,000,000, 40,00,000, 50,000,000, 100,000,000, 200,000,000, 300,000,000, 400,000,000, 500,000,000, 600,000,000, 700,000,000, 800,000,000, 900,000,000, 1,000,000,000, 2,000,000,000, 3,000,000,000, 4,000,000,000, 5,000,000,000, 6,000,000,000, 7,000,000,000, 8,000,000,000, 9,000,000,000, and 10,000,000,000 tagged nucleic acid molecules on the high end of the range. In some embodiments, the population of tagged nucleic acid molecules can include between 100,000,000, 200,000,000, 300,000,000, 400,000,000, 500,000,000, 600,000,000, 700,000,000, 800,000,000, 900,000,000, and 1,000,000,000 tagged nucleic acid molecules on the low end of the range and 500,000,000, 600,000,000, 700,000,000, 800,000,000, 900,000,000, 1,000,000,000, 2,000,000,000, 3,000,000,000, 4,000,000,000, 5,000,000,000 tagged nucleic acid molecules on the high end of the range.

In certain respects a percentage of the total sample nucleic acid molecules in the population of sample nucleic acid molecules can be targeted to have MITs attached. In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.9% of the sample nucleic acid molecules can be targeted to have MITs attached. In other respects a percentage of the sample nucleic acid molecules in the population can have MITs successfully attached. In any of the embodiments disclosed herein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.9% of the sample nucleic acid molecules can have MITs successfully attached to form the population of tagged nucleic acid molecules. In any of the embodiments disclosed herein at least 1, 2, 3, 4, 5, 6, 7, 8, 9, 10, 15, 20, 25, 30, 40, 50, 75, 100, 200, 300, 500, 600, 700, 800, 900, 1,000, 2,000, 3,000, 4,000, 5,000, 6,000, 7,000, 8,000, 9,000, 10,000, 15,000, 20,000, 30,000, 40,000, or 50,000 of the sample nucleic acid molecules can have MITs successfully attached to form the population of tagged nucleic acid molecules.

In some embodiments disclosed herein, MITs can be oligonucleotide sequences of ribonucleotides or deoxyribonucleotides linked through phosphodiester linkages. Nucleotides as disclosed herein can refer to both ribonucleotides and deoxyribonucleotides and a skilled artisan will recognize when either form is relevant for a particular application. In certain embodiments, the nucleotides can be selected from the group of naturally-occurring nucleotides consisting of adenosine, cytidine, guanosine, uridine, 5-methyluridine, deoxyadenosine, deoxycytidine, deoxyguanosine, deoxythymidine, and deoxyuridine. In some embodiments, the MITs can be non-natural nucleotides. Non-natural nucleotides can include: sets of nucleotides that bind to each other, such as, for example, d5SICS and dNaM; metal-coordinated bases such as, for example, 2,6-bis(ethylthiomethyl)pyridine (SPy) with a silver ion and mondentate pyridine (Py) with a copper ion; universal bases that can pair with more than one or any other base such as, for example, 2'-deoxyinosine derivatives, nitroazole analogues, and hydrophobic aromatic non-hydrogen-bonding bases; and xDNA nucleobases with expanded bases. In certain embodiments, the oligonucleotide sequences can be predetermined while in other embodiments, the oligonucleotide sequences can be degenerate.

In some embodiments, MITs include phosphodiester linkages between the natural sugars ribose and/or deoxyribose that are attached to the nucleobase. In some embodiments, non-natural linkages can be used. These linkages include, for example, phosphorothioate, boranophosphate, phosphonate, and triazole linkages. In some embodiments, combinations of the non-natural linkages and/or the phosphodiester linkages can be used. In some embodiments, peptide nucleic acids can be used wherein the sugar backbone is instead made of repeating N-(2-aminoethyl)-glycine units linked by peptide bonds. In any of the embodiments disclosed herein non-natural sugars can be used in place of the ribose or deoxyribose sugar. For example, threose can be used to generate α-(L)-threofuranosyl-(3'-2') nucleic acids (TNA). Other linkage types and sugars will be apparent to a skilled artisan and can be used in any of the embodiments disclosed herein.

In some embodiments, nucleotides with extra bonds between atoms of the sugar can be used. For example, bridged or locked nucleic acids can be used in the MITs. These nucleic acids include a bond between the 2'-position and 4'-position of a ribose sugar.

In certain embodiments, the nucleotides incorporated into the sequence of the MIT can be appended with reactive linkers. At a later time, the reactive linkers can be mixed with an appropriately-tagged molecule in suitable conditions for the reaction to occur. For example, aminoallyl nucleotides can be appended that can react with molecules linked to a reactive leaving group such as succinimidyl ester and thiol-containing nucleotides can be appended that can react with molecules linked to a reactive leaving group such as maleimide. In other embodiments, biotin-linked nucleotides can be used in the sequence of the MIT that can bind streptavidin-tagged molecules.

Various combinations of the natural nucleotides, non-natural nucleotides, phosphodiester linkages, non-natural linkages, natural sugars, non-natural sugars, peptide nucleic acids, bridged nucleic acids, locked nucleic acids, and nucleotides with appended reactive linkers will be recognized by a skilled artisan and can be used to form MITs in any of the embodiments disclosed herein.

Amplifying Tagged Nucleic Acid Molecules

In some embodiments, methods of the present disclosure include amplifying the tagged nucleic acid molecules before determining the sequences of the tagged nucleic acid molecules. Typically, multiple rounds of amplification occur during sample preparation for high-throughput sequencing, as is known in the art. These amplification steps generally all occur after the MITs have been attached to the nucleic acid molecules, although amplification of the sample nucleic acid molecules can occur before MIT attachment in some embodiments. In certain embodiments, after MITs are attached to sample nucleic acid segments of sample nucleic acid molecules, at least 1, 2, 3, 4, 5, or 6 amplification reactions are performed. In high-throughput sequencing, for example, amplification reactions can include amplifying the initial nucleic acid in the sample to generate the library to be sequenced, clonally amplifying the library, typically onto a solid support, and additional amplification reactions to add additional information or functionality such as sample identifying barcodes. Barcodes can be added at any time during the amplification process and before and/or after target enrichment as discussed below. The tagged sample nucleic acid molecules can have one or more than one barcode on one or both ends. Each amplification reaction typically includes multiple cycles (e.g. 2, 3, 4, 5, 6, 7, 8, 9, 10, 11, 12, 13, 14, 15, 16, 17, 18, 19, or 20 on the low end of the range of number of cycles and 5, 6, 7, 8, 9, 10, 11, 12, 13, 14, 15, 16, 17, 18, 19, 20, 25, 30, 35, 40, 45, 50, 75, or 100 cycles on the high end of the range) of amplification either through temperature cycling or natural biochemical reaction cycling as occurs during isothermal amplification. A method of any of the embodiments provided herein, in some examples, can include an amplification step where at least 10, 15, 20, 25, or 30 cycles (e.g. thermocycles in a PCR amplification) of amplification are performed.

In some embodiments, after attaching the MITs, the tagged nucleic acid molecules can be amplified using universal primers that bind to previously attached universal amplification primer binding sequences to generate a library of sample nucleic acid molecules. Specific target nucleic acids in the library of nucleic acid molecules can be enriched for example through multiplex PCR, especially one-sided PCR, or through hybrid capture. The enrichment step can be followed by another universal amplification reaction. Regardless of whether there is a targeted amplification step, an optional barcoding amplification reaction can be used to barcode the tagged nucleic acid molecules that arose from sample nucleic acid molecules from separate samples or subpools such that the products from multiple reaction mixtures or subpools can be pooled. As is known, such barcodes can make it possible to identify the sample from which a tagged nucleic acid molecule was generated. This can be used to identify multiple starting samples and it can be useful if the sample nucleic acid molecules are split after labeling to increase the total number of tag combinations. Such barcodes differ from MITs of the present disclosure because they do not identify individual sample nucleic acid molecules but rather they identify samples from which nucleic acid molecules arose in a mixture of samples. The tagged nucleic acid molecules or amplified tagged nucleic acid molecules are typically templated onto one or more solid supports and typically amplified or clonal amplification can occur during the templating amplification reaction. It is noteworthy that amplification errors can be introduced at any amplification step in the process. Using the methods disclosed herein, it is possible to identify at which amplification step an error occurs, or if the error occurs during a subsequent sequencing reaction. For example, if a sample is split into multiple PCRs, and each PCR adds a new, different MIT, it is possible to determine if an error occurred in a particular PCR step.

In some embodiments, the sample nucleic acid molecules are unaltered before the MITs are attached; after the MITs are attached the tagged nucleic acid molecules are amplified using universal primers to produce a library or population of tagged nucleic acid molecules; the library of amplified tagged nucleic acid molecules undergo target enrichment through multiplex PCR (e.g. one-sided multiplex PCR); the enriched tagged nucleic acid molecules undergo an optional barcoding amplification step; clonal amplification onto one or more solid supports is performed; the sequences of the tagged nucleic acid molecules are determined; and the sample nucleic acid molecules are identified using the determined sequences of the attached MITs.

In any of the embodiments disclosed herein, these amplification steps can be performed using well-known methods in the art, such as PCR amplification with thermocycling or isothermal amplification such as recombinase polymerase amplification. In any of the amplification steps disclosed herein, a skilled artisan will understand how to adapt the methods for isothermal amplification.

In some embodiments, the tagged nucleic acid molecules can be used to generate a library for sequencing, especially high-throughput sequencing. Typically, the tagged nucleic acid molecules are amplified using universal primers that bind universal primer binding sequences that have been incorporated into the tagged nucleic acid molecules as discussed elsewhere herein. In some embodiments, universal amplification can be performed for a number of cycles, such as between 1, 2, 3, 4, 5, 6, 7, 8, 9, 10, 11, 12, 13, 14, 15, 16, 17, 18, 19, and 20 cycles on the low end of the range and 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 cycles on the high end of the range. In some embodiments, amplification can be performed such that each of the tagged nucleic acid molecules is copied to generate between 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 100,000, 200,000, 300,000, 400,000, 500,000, 600,000, 700, 000, 800,000, 900,000, 1,000,000, 1,250,000, 1,500,000, 2,000,000, 2,500,000, 3,000,000, 4,000,000, 5,000,000, 10,000,000, 20,000,000, 30,000,000, 40,00,000, and 50,000, 000 copies on the low end and 5, 6, 7, 8, 9, 10, 15, 20, 25, 30, 40, 50, 60, 70, 80, 90, 100, 150, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 100,000, 200,000, 300,000, 400,000, 500,000, 600, 000, 700,000, 800,000, 900,000, 1,000,000, 1,250,000, 1,500,000, 2,000,000, 2,500,000, 3,000,000, 4,000,000, 5,000,000, 6,000,000, 7,000,000, 8,000,000, 9,000,000, 10,000,000, 20,000,000, 30,000,000, 40,00,000, 50,000, 000, 100,000,000, 200,000,000, 300,000,000, 400,000,000, 500,000,000, 600,000,000, 700,000,000, 800,000,000, 900, 000,000, and 1,000,000,000 copies on the high end.

Target Enrichment

Methods of the present disclosure, in certain embodiments, can include a target enrichment step before the step of determining the sequence of the sample nucleic acid molecules. In some embodiments, target enrichment is performed using a multiplex PCR reaction, especially a one-sided PCR reaction. In these embodiments, a universal primer and a plurality of target-specific primers that bind to internal sequences of target sample nucleic acid segments are used such that they generate amplicons from tagged nucleic acid molecules with both a universal primer binding sequence and a target-specific binding sequence but no amplicons are generated from tagged nucleic acid molecules lacking either or both of these sequences. In some embodiments, the universal primer can bind to the 5' universal primer binding site of one strand of DNA and the target-specific primers can bind to the complement of the DNA strand within the nucleic acid segment 3' to the universal primer binding site on the other strand of complementary DNA. The binding orientation can be reversed and the universal primer can bind to the 3' universal primer binding site of one strand and the target-specific primers can bind to the complement of the DNA strand within the nucleic acid segment 5' to the universal primer binding site on the other strand of complementary DNA.

In some embodiments, of the present disclosure, preferentially enriching the DNA includes obtaining a plurality of hybrid capture probes that target the desired sequences, hybridizing the hybrid capture probes to the DNA in the sample and physically removing some or all of the unhybridized DNA from the sample of DNA. Thus, sequences complementary to the target tagged nucleic acid molecules are bound to solid supports and the tagged nucleic acid molecules are added under conditions such that the targeted tagged nucleic acid molecules anneal to the complementary sequence and the untargeted tagged nucleic acid molecules do not. After removing untargeted tagged nucleic acid molecules, the reaction conditions can be adjusted such that the target tagged nucleic acid molecules dissociate from the solid support and can be isolated. In some embodiments, an amplification step can be performed after hybrid capture using universal amplification primers.

Hybrid capture probe refers to any nucleic acid sequence, possibly modified, that is generated by various methods such as PCR or direct synthesis and intended to be complementary to one strand of a specific target DNA sequence in a sample. The exogenous hybrid capture probes may be added to a prepared sample and hybridized through a denature-reannealing process to form duplexes of exogenous-endogenous fragments. These duplexes may then be physically separated from the sample by various means. Hybrid capture probes were originally developed to target and enrich large fractions of the genome with relative uniformity between targets. In that application, it was important that all targets be amplified with enough uniformity that all target loci could be detected by sequencing; however, no regard was paid to retaining the proportion of alleles in original sample. Following capture, the alleles present in the sample can be determined by direct sequencing of the captured molecules. These sequencing reads can be analyzed and counted according the allele type.

As discussed herein, methods of the present disclosure in some embodiments, include one-sided multiplex PCR methods. In such methods, tagged nucleic acid molecules that have an adapter or adapters at the end or ends can be used. One-sided PCR can be performed in two steps. For example, a first one-sided PCR can be performed on targeted tagged nucleic acid molecules with a plurality of forward primers specific for each targeted tagged nucleic acid molecule and a reverse primer that binds a universal primer binding site that is present on the ligation adapters on all the tagged nucleic acid molecules. A second one-sided PCR can then be performed on the products of the first one-sided PCR using a plurality of forward primer specific for each targeted tagged nucleic acid molecule and a reverse primer that binds the same or a different universal primer binding site from the universal primer binding site used in the first one-sided PCR reaction.

In some embodiments, the tagged nucleic acid molecules undergo templating through clonal amplification onto one or more solid supports, either in one or two reactions. Methods are well-known in the art for templating and/or performing clonal amplification and depend on the sequencing method used for analysis. A skilled artisan will recognize the methods to use to perform clonal amplification.

Amplification Reaction Mixtures

In some embodiments, amplifying the nucleic acid molecules can include forming an amplification reaction mixture. An amplification reaction mixture useful for the present disclosure can include components well-known in the art, especially for PCR amplification. For example, the reaction mixture typically includes a source of nucleotides such as nucleotide triphosphates, a polymerase, magnesium, and primers, and optionally one or more tagged nucleic acid molecules. The reaction mixture in certain embodiments, is formed by combining a polymerase, nucleotide triphosphates, tagged nucleic acid molecules, and a set of forward and/or reverse primers. Accordingly, in certain embodiments provided herein is a reaction mixture that includes a population of tagged nucleic acid molecules and a pool of primers, at least some of which bind the tagged nucleic acid molecules within the population of tagged nucleic acid molecules. In addition to the MIT sequences, the tagged nucleic acid molecules can include adapter sequences, for example, for binding primers for sequencing reactions and/or universal amplification reactions. In some embodiments, the forward and reverse primers for amplifying tagged nucleic acid sequences can be designed to bind to universal primer binding sequences that have been attached to the tagged nucleic acid molecules such that all tagged nucleic acid sequences are amplified. In some embodiments, the forward and reverse primers can be designed such that one binds to a universal primer binding sequence and the other binds to target-specific sequences within the sample nucleic acid segments, such as in one-sided PCR. In other embodiments, the forward and reverse primers can both be designed to bind to target-specific sequences within the sequences of the sample nucleic acid segments, such as in two-sided PCR.

In any of the embodiments disclosed herein, the reaction mixture can include between 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250, 300, 350, 400, 450, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 100,000, 200,000, 300,000, 400,000, 500,000, 600, 000, 700,000, 800,000, 900,000, 1,000,000, 1,250,000, 1,500,000, 2,000,000, 2,500,000, 3,000,000, 4,000,000, 5,000,000, 10,000,000, 20,000,000, 30,000,000, 40,00,000, 50,000,000, 100,000,000, 200,000,000, 300,000,000, 400, 000,000, 500,000,000, 600,000,000, 700,000,000, 800,000, 000, 900,000,000, and 1,000,000,000 tagged nucleic acid molecules on the low end of the range and 3, 4, 5, 6, 7, 8, 9, 10, 15, 20, 25, 30, 40, 50, 60, 70, 80, 90, 100, 150, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 100,000, 200,000, 300,000, 400,000, 500,000, 600,000, 700,000, 800,000, 900,000, 1,000,000, 1,250,000, 1,500,000, 2,000,000, 2,500,000, 3,000,000, 4,000,000, 5,000,000, 6,000,000, 7,000,000, 8,000,000, 9,000,000, 10,000,000, 20,000,000, 30,000,000, 40,00,000, 50,000,000, 100,000,000, 200,000,000, 300,000, 000, 400,000,000, 500,000,000, 600,000,000, 700,000,000, 800,000,000, 900,000,000, 1,000,000,000, 2,000,000,000, 3,000,000,000, 4,000,000,000, 5,000,000,000, 6,000,000, 000, 7,000,000,000, 8,000,000,000, 9,000,000,000, and 10,000,000,000 tagged nucleic acid molecules on the high end of the range. In some embodiments, the reaction mixture can include between 1, 2, 3, 4, 5, 6, 7, 8, 9, 10, 15, 20, 25, 30, 35, 40, 45, 50, 60, 70, 80, 90, 100, 150, 200, 250, 300, 400, 500, 600, 700, 800, 900, 1,000, 2,000, 3,000, 4,000, 5,000, 6,000, 7,000, 8,000, 9,000, and 10,000 copies of each of the tagged nucleic acid molecules on the low end of the range and 20, 25, 30, 35, 40, 45, 50, 60, 70, 80, 90, 100, 150, 200, 250, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, and 100,000 copies of each of the tagged nucleic acid molecules on the high end of the range.

In any of the embodiments disclosed herein, at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.9% of the tagged nucleic acid molecules can be successfully amplified, wherein successful amplification is defined as PCR that has an efficiency of at least 80%, 85%, 90%, 95%, 96%, 97%, 98%, 99%, 99.9%, or 100%.

In further embodiments, the reaction mixture can include a population of between 100 and 1,000,000 tagged nucleic acid molecules, each between 50 and 500 nucleotides in length, with between 10 and 100,000 different sample nucleic acid segments, and a set of MITs of between 10 and 500 MITs that are each between 4 and 20 nucleotides in length, wherein the ratio of the number of sample nucleic acid segments to the number of MITs in the population is between 2:1 and 100:1. In certain embodiments, each member of the set of MITs is attached to at least one tagged nucleic acid molecule of the population. In certain embodiments, at least two tagged nucleic acid molecules of the population include at least one identical MIT and a sample nucleic acid segment that is greater than 50% different. In some embodiments, the reaction mixture can include a polymerase or ligase.

In some embodiments, the reaction mixture can include a set, library, plurality, or pool of primers, that includes 25, 50, 100, 200, 250, 300, 400, 500, 1,000, 2,500, 5,000, 10,000, 20,000, 25,000, or 50,000 primers or primer pairs on the low end of the range, and 200, 250, 300, 400, 500, 1,000, 2,500, 5,000, 10,000, 20,000, 25,000, 50,000, 60,000, 70,000, 80,000, 90,000, 100,000, 125,000, 150,000, 200,000, 250, 000, 300,000, 400,000, or 500,000 primers or primer pairs on the high end of the range, that each bind to a primer binding sequence located within one or more of a plurality of the tagged nucleic acid molecules.

In some embodiments, a library of nucleic acid molecules is formed that is useful for sequencing. In some embodiments, the library can include between 10, 15, 20, 25, 30, 35, 40, 45, 50, 60, 70, 80, 90, 100, 150, 200, 250, 300, 400, 500, 600, 700, 800, 900, and 1,000 copies of each of the tagged nucleic acid molecules on the low end of the range and 20, 25, 30, 35, 40, 45, 50, 60, 70, 80, 90, 100, 150, 200, 250, 300, 400, 500, 600, 700, 800, 900, 1,000, 2,000, 3,000, 4,000, 5,000, 6,000, 7,000, 8,000, 9,000, and 10,000 copies of each of the tagged nucleic acid molecules on the high end of the range.

In some embodiments, the library of nucleic acid molecules can include at least 2, 3, 4, 5, 6, 7, 8, 9, 10, 15, 20, 25, 30, 35, 40, 45, 50, 60, 70, 80, 90, 100, 150, 200, 250, 300, 400, 500, 600, 700, 800, 900, and 1,000 tagged nucleic acid molecules with an identical attached first MIT at the 5' end of nucleic acid segment, an identical attached second MIT at the 3' end of nucleic acid segment, and a sample nucleic acid segment that has at least 1, 2, 3, 4, 5, 6, 7, 8, 9, 10, 11, 12, 13, 14, 15, 16, 17, 18, 19, or 20 nucleotide differences.

In some embodiments, the library of nucleic acid molecules can include a plurality of clonal population of each of the tagged nucleic acid molecules on a solid support or plurality of solid supports.

In some embodiments, a polymerase with proof-reading activity, a polymerase without (or with negligible) proof-reading activity, or a mixture of a polymerase with proof-reading activity and a polymerase without (or with negligible) proof-reading activity is included in amplification reaction mixtures herein. In some embodiments, a hot start polymerase, a non-hot start polymerase, or a mixture of a hot start polymerase and a non-hot start polymerase is used. In some embodiments, a HotStarTaq DNA polymerase is used (see, for example, Qiagen, Hilden, Germany). In some embodiments, AmpliTaq Gold® DNA Polymerase is used (Thermo Fisher, Carlsbad, Calif.). In some embodiments, a PrimeSTAR GXL DNA polymerase, a high-fidelity polymerase that provides efficient PCR amplification when there is excess template in the reaction mixture, and when amplifying long products, is used (Takara Clontech, Mountain View, Calif.). In some embodiments, KAPA Taq DNA Polymerase or KAPA Taq HotStart DNA Polymerase are used; they are based on the single-subunit, wild-type Taq DNA polymerase of the thermophilic bacterium *Thermus aquaticus* and have 5'-3' polymerase and 5'-3' exonuclease activities, but no 3' to 5' exonuclease (proofreading) activity (Kapa Biosystems, Wilmington, Mass.). In some embodiments, Pfu DNA polymerase is used; it is a highly thermostable DNA polymerase from the hyperthermophilic archaeum *Pyrococcus furiosus*. Pfu catalyzes the template-dependent polymerization of nucleotides into duplex DNA in the 5'→3' direction and also exhibits 3'→5' exonuclease (proofreading) activity that enables the polymerase to correct nucleotide incorporation errors. It has no 5'→3' exonuclease activity (Thermo Fisher Scientific, Waltham, Mass.). In some embodiments, Klentaq1 is used; it is a Klenow-fragment analog of Taq DNA polymerase with no exonuclease or endonuclease activity (DNA Polymerase Technology, St. Louis, Mo.). In some embodiments, the polymerase is a Phusion DNA polymerase, such as Phusion High-Fidelity DNA polymerase or Phusion Hot Start Flex DNA polymerase (New England BioLabs, Ipswich, Mass.). In some embodiments, the polymerase is a Q5® DNA Polymerase, such as Q5® High-Fidelity DNA Polymerase or Q5® Hot Start High-Fidelity DNA Polymerase (New England BioLabs). In some embodiments, the polymerase is a T4 DNA polymerase (New England BioLabs).

In some embodiments, between 5 and 600 Units/mL (Units per 1 mL of reaction volume) of polymerase is used, such as between 5 to 100, 100 to 200, 200 to 300, 300 to 400, 400 to 500, or 500 to 600 Units/mL, inclusive.

PCR Methods

In some embodiments, hot-start PCR is used to reduce or prevent polymerization prior to PCR thermocycling. Exemplary hot-start PCR methods include initial inhibition of the DNA polymerase or physical separation of reaction components reaction until the reaction mixture reaches the higher temperatures. In some embodiments, the slow release of magnesium is used. DNA polymerase requires magnesium ions for activity, so the magnesium is chemically separated from the reaction by binding to a chemical compound, and is released into the solution only at high temperature. In some embodiments, non-covalent binding of an inhibitor is used. In this method, a peptide, antibody, or aptamer can be non-covalently bound to the enzyme at low temperature to inhibit its activity. After incubation at elevated temperature, the inhibitor is released and the reaction starts. In some embodiments, a cold-sensitive Taq polymerase is used, such as a modified DNA polymerase with almost no activity at low temperature. In some embodiments, chemical modification is used. In this method, a molecule is covalently bound to the side chain of an amino acid in the active site of the DNA polymerase. The molecule is released from the enzyme by incubation of the reaction mixture at elevated temperature. Once the molecule is released, the enzyme is activated.

In some embodiments, the amount of template nucleic acids (such as an RNA or DNA sample) is between 20 and 5,000 ng, such as between 20 to 200; 200 to 400; 400 to 600; 600 to 1,000; 1,000 to 1,500; or 2,000 to 3,000 ng, inclusive.

Methods for performing PCR are well-known in the art. Such methods typically include cycles of a denaturing step, an annealing step, and an elongation step, which can be the same or different than the annealing step.

An exemplary set of conditions includes a semi-nested PCR approach. The first PCR reaction uses 20 µl a reaction volume with 2× Qiagen MM final concentration, 1.875 nM of each primer in the library (outer forward and reverse primers), and DNA template. Thermocycling parameters include 95° C. for 10 minutes; 25 cycles of 96° C. for 30 seconds, 65° C. for 1 minute, 58° C. for 6 minutes, 60° C. for 8 minutes, 65° C. for 4 minutes, and 72° C. for 30 seconds; and then 72° C. for 2 minutes, and then a 4° C. hold. Next, 2 µl of the resulting product, diluted 1:200, is used as input in a second PCR reaction. This reaction uses a 10 µl reaction volume with 1× Qiagen MM final concentration, 20 nM of each inner forward primer, and 1 µM of reverse primer tag. Thermocycling parameters include 95° C. for 10 minutes; 15 cycles of 95° C. for 30 seconds, 65° C. for 1 minute, 60° C. for 5 minutes, 65° C. for 5 minutes, and 72° C. for 30 seconds; and then 72° C. for 2 minutes, and then a 4° C. hold. The annealing temperature can optionally be higher than the melting temperatures of some or all of the primers, as discussed herein (see U.S. patent application Ser. No. 14/918,544, filed Oct. 20, 2015, which is herein incorporated by reference in its entirety).

The melting temperature ($T_m$) is the temperature at which one-half (50%) of a DNA duplex of an oligonucleotide (such as a primer) and its perfect complement dissociates and becomes single strand DNA. The annealing temperature ($T_A$) is the temperature one runs the PCR protocol at. For prior methods, it is usually 5° C. below the lowest $T_m$ of the primers used, thus close to all possible duplexes are formed (such that essentially all the primer molecules bind the template nucleic acid). While this is highly efficient, at lower temperatures unspecific reactions are more likely to occur. One consequence of having too low a $T_A$ is that primers may anneal to sequences other than the true target, as internal single-base mismatches or partial annealing may be tolerated. In some embodiments, of the present disclosures, the $T_A$ is higher than ($T_m$), where at a given moment only a small fraction of the targets has a primer annealed (such as only ~1-5%). If these get extended, they are removed from the equilibrium of annealing and dissociating primers and target (as extension increases $T_m$ quickly to above 70° C.), and a new ~1-5% of targets has primers. Thus, by giving the reaction a long time for annealing, one can get ~100% of the targets copied per cycle.

In various embodiments, the range of the annealing temperature is between 1° C., 2° C., 3° C., 4° C., 5° C., 6° C., 7° C., 8° C., 9° C., 10° C., 11° C., 12° C., and 13° C. on the low end of the range and 2° C., 3° C., 4° C., 5° C., 6° C., 7° C., 8° C., 9° C., 10° C., 11° C., 12° C., 13° C., and 15° C. on the high end of the range, greater than the melting temperature (such as the empirically measured or calculated $T_m$) of at least 25, 50, 60, 70, 75, 80, 90, 95, or 100% of the non-identical primers. In various embodiments, the annealing temperature is between 1° C. and 15° C. (such as between 1° C. to 10° C., 1° C. to 5° C., 1° C. to 3° C., 3° C. to 5° C., 5° C. to 10° C., 5° C. to 8° C., 8° C. to 10° C., 10° C. to 12° C., or 12° C. to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In various embodiments, the annealing temperature is between 1 and 15° C. (such as between 1° C. to 10° C., 1° C. to 5° C., 1° C. to 3° C., 3° C. to 5° C., 3° C. to 8° C., 5° C. to 10° C., 5° C. to 8° C., 8° C. to 10° C., 10° C. to 12° C., or 12° C. to 15° C., inclusive) greater than the melting temperature (such as the empirically measured or calculated $T_m$) of at least 25%, 50%, 60%, 70%, 75%, 80%, 90%, 95%, or all of the non-identical primers, and the length of the annealing step (per PCR cycle) is between 5 and 180 minutes, such as 15 and 120 minutes, 15 and 60 minutes, 15 and 45 minutes, or 20 and 60 minutes, inclusive.

In addition to thermocycling during PCR, isothermal amplification has been recognized as a means to amplify nucleic acid molecules. In any of the PCR methods disclosed herein, a skilled artisan will understand how to adapt the methods for use with this technology. For example, in some embodiments, the reaction mixture can include tagged nucleic acid molecules, a pool of primers, nucleotide triphosphates, magnesium, and an isothermal polymerase. There are several isothermal polymerases available to perform isothermal amplification. These include Bst DNA polymerase, full length; Bst DNA polymerase, large fragment; Bst 2.0 DNA polymerase; Bst 2.0 WarmStart DNA polymerase; and Bst 3.0 DNA polymerase (all available from New England Biolabs). The polymerase used can be dependent on the method of isothermal amplification. There are several types of isothermal amplification available, including recombinase polymerase amplification (RPA), loop-mediated isothermal amplification (LAMP), strand displacement amplification (SDA), helicase-dependent amplification (HDA), nicking enzyme amplification reaction (NEAR), and template walking.

Determining the Sequences of Tagged Nucleic Acid Molecules

In some embodiments, the sequences of tagged nucleic acid molecules are determined directly by methods known in the art, especially high-throughput sequencing. More typically, the sequences of tagged nucleic acid molecules are determined after one or more rounds of amplification that occurs during sample preparation for high-throughput sequencing. Such amplifications typically include library preparation, clonal amplification, and amplification(s) to add additional sequences or functionality, such as sample barcodes, to the sample nucleic acid molecules. During high-throughput sequencing sample preparation, tagged nucleic acid molecules are typically clonally amplified onto one or more solid supports. These monoclonal or substantially monoclonal colonies are then subjected to a sequencing reaction. Furthermore, next generation sequencing sample preparation can include a targeted amplification reaction typically after library preparation and before clonal amplification. Such targeted amplification can be a multiplex amplification reaction.

In any of the embodiments disclosed herein, the methods and compositions can be used to identify amplification errors versus true sequence variants in the sample nucleic acid molecules. The present disclosure can further identify the likely source of amplification error and can further identify the most likely true sequence of the initial sample nucleic acid molecule.

In some embodiments, of the method provided herein, at least a portion and in some embodiments, the entire sequence of at least one tagged nucleic acid molecule is determined. Methods for determining the sequence of a nucleic acid molecule are known in the art. Any of the sequencing methods known in the art, for example Sanger sequencing, pyrosequencing, reversible dye terminator sequencing, sequencing by ligation, or sequencing by hybridization, can be used for such sequence determination. In some embodiments, high-throughput next-generation (massively parallel) sequencing techniques such as, but not limited to, those employed in Solexa (I lumina), Genome Analyzer IIx (Illumina), MiSeq (Illumina), HiSeq (Illumina), 454 (Roche), SOLiD (Life Technologies), Ion Torrent (Life Technologies, Carlsbad, Calif.), GS FLX+ (Roche), True Single Molecule Sequencing platform (Helicos), electron microscope sequencing method (Halcyon Molecular) can be used, or any other sequencing method can be used for sequencing the tagged nucleic acid molecules generated by the methods provided herein. In some embodiments, any high-throughput, massively-parallel sequencing method can be used and a skilled artisan will understand how to adjust the disclosed methods to accomplish the appropriate MIT attachment. Thus, a sequencing by synthesis or sequencing by ligation, high-throughput reaction can be used, for example. Furthermore, the sequencer can detect a signal generated during the sequencing reaction, which can be a fluorescent signal or an ion, such as a hydrogen ion. All of these methods physically transform the genetic data stored in a sample of DNA into a set of genetic data that is typically stored in a memory device in route to being processed.

Identifying the Sample Nucleic Acid Molecules

The step of determining the sequences of the tagged nucleic acid molecules includes determining the sequences of at least a portion of the sample nucleic acid molecules, sample nucleic acid segments, or target loci and the sequences of tags that remain attached to the sample nucleic acid segments, including the sequences of MITs. In some embodiments, copies of tagged nucleic acid molecules that have been derived from the same initial tagged nucleic acid molecule can be identified by comparing the MIT sequences attached to the tagged nucleic acid molecule. Copies derived from the same initial tagged nucleic acid molecules will have the same MITs attached in the same location relative to the sample nucleic acid segment. In some embodiments, the fragment-specific insert ends are mapped to specific locations in the genome of the organism and these mapped locations or the sequences of the fragment-specific insert ends themselves as discussed herein are used in conjunction with the sequences of the MITs to identify the initial tagged nucleic acid molecules from which the copies are derived. In some embodiments, tagged nucleic acid molecules comprising complementary MITs and complementary nucleic acid segment sequences, i.e. tagged nucleic acid molecules that have been derived from the same nucleic acid molecule and represent the plus and minus strands of the sample nucleic acid molecule, are identified and paired. In some embodiments, the paired MIT families are used to verify differences in the original sequence. Any change in the sequence should be present in all copies of the tagged nucleic acid molecules derived from the sample nucleic acid molecules. This information provides additional confidence that the sequences of the tagged nucleic acid molecules derived from the plus strand and the minus strand of the sample represent a difference in the sequence of the sample nucleic acid molecule and not a change introduced during sample preparation or an error in base-calling during sequencing.

In some embodiments, two main types of tagged nucleic acid molecules are generated that will be informative for further analysis: tagged nucleic acid molecules with identical attached MITs in the same positions and with substantially the same sample nucleic acid segment sequences and tagged nucleic acid molecules with different attached MITs and with substantially the same sample nucleic acid segment sequences. As discussed in detail herein, the tagged nucleic acid molecules with identical attached MITs in the same positions and with substantially the same sample nucleic acid segment sequences can be used to identify amplification errors and the tagged nucleic acid molecules with at least one difference between the attached MITs, and with substantially the same sample nucleic acid segment sequences can be used to identify true sequence variants.

After the MITs are attached, amplification errors can be identified by comparing the sequences of tagged nucleic acid molecules with identical MITs in the same relative positions and with substantially the same sample nucleic acid sequences. When both strands of an initial sample nucleic acid molecule are tagged with the same MIT or MITs, it is possible to identify paired MIT nucleic acid segment families that have complementary MIT and nucleic acid segment sequences. These paired MIT nucleic acid segment families can be used to boost the confidence that the sequence variation was present on both strands of the sample nucleic acid molecule. If the tagged nucleic acid molecules derived from the sample nucleic acid molecule show differences in their sequences, then either there was a mismatch present in the sample nucleic acid molecule or an error was introduced during amplification or base calling. The sequences from a paired MIT nucleic acid segment family with sequence differences will typically be discarded before further analysis is performed. However, these paired MIT nucleic acid segment families with sequence differences could be used to identify mismatches in the sample nucleic acid molecules.

Amplification errors that introduce one or more changes into the sequence of a nucleic acid segment will not be present in all copies derived from the initial tagged nucleic acid molecule. At most 25% of the copies derived from both strands of an initial tagged nucleic acid molecule will have the error in the sequence of the nucleic acid segment if the error is introduced during the first round of amplification. If amplification proceeds with perfect efficiency, the percentage of copies with a specific error will be halved during every round of amplification, i.e. 12.5% of the copies derived from the initial tagged nucleic acid molecule will have the error if it is introduced during the second round of amplification and 6.25% of the copies derived from the initial tagged nucleic acid molecule will have the error if it is introduced during the third round of amplification, etc. Using this knowledge, it can be possible to identify or estimate when an amplification error was introduced; including, in the embodiments where multiple amplifications occur after the MITs are attached, at which step the amplification error was introduced. In any of the embodiments disclosed herein, when amplification errors are present within the sample nucleic acid segment, the methods detailed herein can be used to determine the most likely sequence of the initial sample nucleic acid molecule. For example, the most likely sequence can be determined from the pool of copies of an initial tagged nucleic acid molecule as the most common sequence. In some embodiments, prior probabilities can be used when determining the most likely sequence, for example, known mutation rates at specific chromosomal sites in normal or diseased cells or the population frequency of specific single nucleotide polymorphisms.

The probability of having an identical amplification error in more than one tagged nucleic acid molecule with different MITs and substantially the same nucleic acid segment sequence is exceedingly low, such that identical sequence variants on tagged nucleic acid molecules with substantially the same sequences and identical MITs in the same relative positions are considered to be derived from the same molecule and not having arisen independently.

True sequence variations present in the sample nucleic acid segments can be identified since all copies derived from one initial tagged nucleic acid molecule will have the same sequence in the variant location and at least one pool of copies of a tagged nucleic acid molecule with substantially the same sample nucleic acid segment sequence and differences in the MITs will have a different sequence in the same variant location, wherein differences in the MITs can be either at least one different attached MIT from the set of MITs or different relative positions of identical MITs.

In any of the embodiments disclosed herein, a sequence difference can be called as an amplification error if the percentage of the copies derived from the same initial tagged nucleic acid molecule with the sequence change is below 50%, 45%, 40%, 35%, 30%, 25%, 20%, 15%, 10% 9%, 8%, 7%, 6%, 5%, 4%, 3%, 2%, or 1%. In certain embodiments, copies can be said to be derived from the same initial tagged nucleic acid molecule if the attached MITs are identical and in the same relative location and if the sample nucleic acid segment sequence is substantially the same. In any of the embodiments disclosed herein, a sequence change can be called as a true sequence variant in the initial tagged nucleic acid molecule if the sequence differs in at least two tagged nucleic acid molecules with substantially the same sample nucleic acid segments and the pools of the copies derived from each of the at least two tagged nucleic acid molecules with substantially the same sample nucleic acid segments are at least 70%, 75%, 80%, 85%, 90%, 95%, 96%, 97%, 98%, 99%, 99.9% or 100% identical within each pool, and each pool is identified by having at least one different MIT and/or an MIT at a different location relative to a sample nucleic acid segment.

In some embodiments, the sequences of the tagged nucleic acid molecules can be used to identify between 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.9% of the sample nucleic acid molecules on the low end of the range or 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.9%, or 100% of the sample nucleic acid molecules on the high end of the range.

In some embodiments, for each sample nucleic acid molecule the methods can be used to identify between 1, 2, 3, 4, 5, 6, 7, 8, 9, 10, 15, 20, 25, 50, 75, 100, 250, 500, 1,000, 2,000, 3,000, 4,000, 5,000, 10,000, 15,000, 20,000, 25,000, 30,000, 40,000, 50,000, 60,000, 70,000, 80,000, 90,000, and 100,000 amplification errors on the low end of the range and 5, 6, 7, 8, 9, 10, 11, 12, 13, 14, 15, 16, 17, 18, 19, 20, 25, 50, 75, 100, 250, 500, 1,000, 2,000, 3,000, 4,000, 5,000, 10,000, 15,000, 20,000, 25,000, 30,000, 40,000, 50,000, 60,000, 70,000, 80,000, 90,000, 100,000, 200,000, 300,000, 400,000, 500,000, 600,000, 700,000, 800,000, 900,000, and 1,000,000 amplification errors on the high end of the range. In some embodiments, for each sample nucleic acid molecule the methods can be used to identify between 1, 2, 3, 4, 5, 6, 7, 8, 9, 10, 11, 12, 13, 14, 15, 16, 17, 18, 19, 20, 25, 50, 75, 100, 250, 500, 1,000, 2,000, 3,000, 4,000, 5,000, 10,000, 15,000, 20,000, 25,000, 30,000, 40,000, 50,000, 60,000, 70,000, 80,000, 90,000, and 100,000 true sequence variants in the sample nucleic acid molecule on the low end of the range and 2, 3, 4, 5, 6, 7, 8, 9, 10, 11, 12, 13, 14, 15, 16, 17, 18, 19, 20, 25, 30, 35, 40, 45, 50, 75, 100, 250, 500, 1,000, 2,000, 3,000, 4,000, 5,000, 10,000, 15,000, 20,000, 25,000, 30,000, 40,000, 50,000, 60,000, 70,000, 80,000, 90,000, 100,000, 200,000, 300,000, 400,000, 500,000, 600,000, 700,000, 800,000, 900,000, and 1,000,000 true sequence variants in the sample nucleic acid molecule on the high end of the range.

Other uses for the embodiments disclosed herein will be apparent to a skilled artisan who will understand how to adapt the methods. For example, the methods can be used to measure amplification bias, especially changes in the amplification bias of specific nucleic acid molecules after the introduction of amplification errors. The methods can also be used to characterize the mutation rates of polymerases. By splitting the samples and barcoding the reaction mixtures, it is possible to characterize the mutation rates of different polymerases at the same time.

Kits for MITs

Any of the components used in the various embodiments disclosed herein can be assembled into kits. A kit can include a container that holds any of the sets of MITs disclosed herein. The MITs can be between 2, 3, 4, 5, 6, 7, 8, 9, 10, 11, 12, 13, 14, and 15 nucleotides long on the low end of the range and 5, 6, 7, 8, 9, 10, 11, 12, 13, 14, 15, 16, 17, 18, 19, 20, 25, and 30 nucleotides long on the high end of the range. The MITs can be double-strand nucleic acid adaptors. These adaptors can further comprise a portion of a Y-adaptor nucleic acid molecule with a base-paired double-stranded polynucleotide segment and at least one non-base-paired single-stranded polynucleotide segment. These Y-adaptors can comprise identical sequences besides the sequences of the MITs. The double-stranded polynucleotide segment of the Y-adaptors can be between 1, 2, 3, 4, 5, 6, 7, 8, 9, 10, 15, 20, and 25 nucleotides long on the low end of the range and 5, 10, 15, 20, 25, 30, 35, 40, 45, 50, 60, 70, 80, 90, and 100 nucleotides long on the high end of the range. The single-stranded polynucleotide segment of the Y-adaptors can be between 1, 2, 3, 4, 5, 6, 7, 8, 9, 10, 15, 20, and 25 nucleotides long on the low end of the range and 5, 10, 15, 20, 25, 30, 35, 40, 45, 50, 60, 70, 80, 90, and 100 nucleotides long on the high end of the range.

In any of the embodiments disclosed herein, the MITs can be a part of a polynucleotide segment that includes a universal primer binding sequence. In some embodiments, the MITs can be located 5' to the universal primer binding sequences. In some embodiments, the MITs can be located within the universal primer binding sequence such that when the polynucleotide segment is bound to DNA, the sequences of the MITs will form non-base-paired loops. In any of the embodiments disclosed herein, the kit can include a set of sample-specific primers designed to bind to internal sequences of the sample nucleic acid molecules, nucleic acid segments, or target loci. In some embodiments, the MITs can be a portion of a polynucleotide that further comprises the sample-specific primer sequences. In these embodiments the MIT can be located 5' to the sample-specific primer sequences or the MITs can be located within the sample-specific primer sequences such that when the polynucleotide segment is bound to DNA, the sequences of the MITs will form non-base-paired loops. In some embodiments, the set of sample-specific primers can include forward and reverse primers for each target locus. In some embodiments, the set of sample-specific primers can be forward or reverse primers and a set of universal primers can be used as the reverse or forward primers, respectively.

In any of the embodiments disclosed herein the kit can include single-stranded oligonucleotides on one or more immobilized substrates. In some embodiments, the single-stranded oligonucleotides on one or more immobilized substrates can be used to enrich the samples for specific sequences by performing hybrid capture and removing the unbound nucleic acid molecules. In any of the embodiments disclosed herein the kit can include a container that holds a cell lysis buffer, tubes for performing cell lysis, and/or tubes for purifying DNA from a sample. In some embodiments, the cell lysis buffer, tubes and/or tubes can be designed for specific types of cells or samples, such as circulating cell-free DNA found in blood samples, including circulating cell-free fetal DNA and circulating cell-free tumor DNA.

Any of the kits disclosed herein can include an amplification reaction mixture comprising any of the following: a reaction buffer, dNTPs, dNTPs, and a polymerase. In some embodiments, the kit can include a ligation buffer and a ligase. In any of the embodiments disclosed herein, the kit can also include a means for clonally amplifying tagged nucleic acid molecules onto one or more solid supports. A skilled artisan will understand which components to include in a kit to enable the use of such kits for the various methods herein.

Determining the Number of Copies of One or More Chromosomes or Chromosome Segments of Interest In some embodiments, methods provided herein for identifying individual sample nucleic acid molecules using MITs, can be used as part of methods to determine the number of copies of one or more chromosomes or chromosome segments of interest in a sample. As demonstrated by the mathematical proofs provided in Example 3, by using methods that include MITs for identifying individual sample nucleic acid molecules as part of methods for determining the number of copies of one or more chromosomes or chromosome segments of interest in a sample, significant cost and sample savings can be achieved. For example, based on the reduced noise and improved accuracy obtained with the use of MITs for identifying individual sample nucleic acid molecules demonstrated in Example 1, as little as 100 µl of plasma can be used to obtain results with an acceptable confidence. Furthermore, results with an acceptable confidence can be attained with as few as 1,780,000 sequencing reads. Thus, two important limitations in current methods can be overcome: sample volume and cost.

The present disclosure is of use in, among other areas, the determination of the number of copies of one or more chromosomes or chromosome segments of interest in a sample, as disclosed herein. Methods for determining the number of chromosome(s) or chromosome segments of interest that can be adapted for use in methods of the present disclosure include those disclosed, for example, in published U.S. patent application Ser. No. 13/499,086 filed Mar. 29, 2012; U.S. patent application Ser. No. 14/692,703 filed Apr. 21, 2015; U.S. patent application Ser. No. 14/877,925 filed Oct. 7, 2015; U.S. patent application Ser. No. 14/918,544 filed Oct. 20, 2015; "Noninvasive prenatal detection and selective analysis of cell-free DNA obtained from maternal blood: evaluation for trisomy 21 and trisomy 18" (Sparks et al. April 2012. American Journal of Obstetrics and Gynecology. 206(4):319.e1-9); and "Detection of Clonal and Subclonal Copy-Number Variants in Cell-Free DNA from Patients with Breast Cancer Using a Massively Multiplexed PCR Methodology" (Kirkizlar et al. October 2015. Translation Oncology. 8(5):407-416), which are each herein incorporated by reference in their entireties.

Using MITs, a smaller sample volume of blood or a fraction thereof can be required to obtain results with an acceptable confidence. In some embodiments, the sample of blood can be a maternal blood sample for use in noninvasive prenatal testing. This can reduce any effects on patients and can reduce cost of sample preparation. In any of the embodiments disclosed herein the volume of the sample can be between 0.01, 0.02, 0.03, 0.04, 0.05, 0.06, 0.07, 0.08, 0.09, 0.1, 0.125, 0.15, 0.175, 0.2, 0.25, 0.3, 0.35, 0.4, 0.45, and 0.5 ml on the low end of the range and 0.05, 0.06, 0.07, 0.08, 0.09, 0.1, 0.125, 0.15, 0.175, 0.2, 0.25, 0.3, 0.35, 0.4, 0.45, 0.5, 0.6, 0.7, 0.8, 0.9, 1 1.25 1.5, 1.75, 2, 2.5, 3, 3.5, 4, 4.5, and 5 ml on the high end of the range. In some embodiments, the sample volume is between 0.1, 0.125, 0.15, 0.175, 0.2, 0.25, 0.3, 0.35, 0.4, 0.45, and 0.5 ml on the low end of the range and 0.25, 0.3, 0.35, 0.4, 0.45, 0.5, 0.6, 0.7, 0.8, 0.9, 1 1.25 1.5, 1.75, 2, 2.5, and 3 ml on the high end of the range.

In any of the embodiments disclosed herein, the sample can be a maternal blood sample that comprises circulating cell-free DNA from a fetus and the mother of the fetus. In some embodiments, these samples are used to perform non-invasive prenatal testing. In other embodiments, the sample can be a blood sample from a person having or suspected of having cancer. In some embodiments, the circulating cell-free DNA can include DNA fragments with lengths between 50, 60, 70, 80, 90, 100, 110, 120, 130, 140, and 150 nucleotides on the low end of the range and 60, 70, 80, 90, 100, 110, 120, 130, 140, 150, 160, 170, 180, 190, and 200 nucleotides on the high end of the range.

In some embodiments, the lengths of any of the one or more chromosome segments of interest can be between 100, 200, 300, 400, 500, 600, 700, 800, 900, 1,000, 2,000, 3,000, 4,000, 5,000, 6,000, 7,000, 8,000, 9,000, 10,000, 15,000, 20,000, 25,000, 50,000, 60,000, 70,000, 80,000, 90,000, and 100,000 nucleotides long on the low end of the range and 500, 600, 700, 800, 900, 1,000, 2,000, 3,000, 4,000, 5,000, 6,000, 7,000, 8,000, 9,000, 10,000, 15,000, 20,000, 25,000, 50,000, 60,000, 70,000, 80,000, 90,000, 100,000, 200,000, 300,000, 400,000, 500,000, 600,000, 700,000, 800,000, 900,000, 1,000,000, 1,000,000, 2,000,000, 3,000,000, 4,000,000, 5,000,000, 6,000,000, 7,000,000, 8,000,000, 9,000,000, 10,000,000, 15,000,000, 20,000,000, 25,000,000, 30,000,000, 40,000,000, 50,000,000, 60,000,000, 70,000,000, 80,000,000, 90,000,000, 100,000,000, 125,000,000, 150,000,000, 175,000,000, 200,000,000, 250,000,000, and 300,000,000 nucleotides long on the high end of the range.

In one aspect, the present disclosure features methods for determining the number of copies of one or more chromosomes or chromosome segments of interest in a sample. In some embodiments, a method for determining the number of copies of one or more chromosomes or chromosome segments of interest in a sample of blood or a fraction thereof includes forming a reaction mixture of sample nucleic acid molecules and a set of Molecular Index Tags (MITs) to generate a population of tagged nucleic acid molecules, wherein at least some of the sample nucleic acid molecules comprise one or more target loci of a plurality of target loci on the chromosome or chromosome segment of interest; amplifying the population of tagged nucleic acid molecules to create a library of tagged nucleic acid molecules; determining the sequences of the attached MITs and at least a portion of the sample nucleic acid segments of the tagged nucleic acid molecules in the library of tagged nucleic acid molecules, to determine the identity of a sample nucleic acid molecule that gave rise to a tagged nucleic acid molecule; measuring a quantity of DNA for each target locus by counting the number of sample nucleic acid molecules that comprise each target locus using the determined identities; measuring a quantity of DNA for each target locus by counting the number of sample nucleic acid molecules that comprise each target locus using the determined identities;

determining, on a computer, the number of copies of the one or more chromosomes or chromosome segments of interest using the quantity of DNA at each target locus in the sample nucleic acid molecules, wherein the number of target loci and the volume of the sample provide an effective amount of total target loci to achieve a desired sensitivity and a desired specificity for the copy number determination. The total target loci, $T_L$, can be defined as the product of the total number of sample nucleic acid molecules that span each target locus in a sample, C, and the number of target loci in the sample, L, such that $T_L=C\times L$. The effective amount, $E_A$, can be defined as the volume necessary to obtain a particular number of total target loci for a target sensitivity and specificity. In some embodiments, the number of total target loci can be between 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 75,000, and 100,000 total target loci on the low end of the range and 500, 600, 700, 800, 900, 1,000, 2,000, 3,000, 4,000, 5,000, 6,000, 7,000, 8,000, 9,000, 10,000, 20,000, 30,000, 40,000, 50,000, 75,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, and 10,000,000 total target loci on the high end of the range. The effective amount can take into account the sample preparation efficiency and the fraction of DNA in a mixed sample, for example, the fetal fraction in a maternal blood sample. Tables 1 and 3 in Example 3 show the total number of sequencing reads, which are the same as the total target loci, required to obtain a target sensitivity and specificity for different methods of the present disclosure. In some embodiments, the total number of sample nucleic acid molecules in the population of sample nucleic acid molecules is greater than the diversity of MITs in the set of MITs. In further embodiments the sample comprises a mixture of two genetically distinct genomes. For example, the mixture can be a blood or plasma sample comprising circulating cell-free tumor DNA and normal DNA, or maternal DNA and fetal DNA.

Example 3 herein provides tables that identify a total number of sequencing reads or total target loci needed for achieving a certain level of specificity and sensitivity at different percent mixtures ("Fraction of G2 in the sample"), which can be for example, the percent of cancer vs. normal DNA or the percent of fetal vs. maternal DNA. Total target loci are identified by multiplying the number of target loci for a chromosome or chromosome segment by the number of haploid copies of the target loci provided by the sample volume. For example, as demonstrated in Example 3, to achieve a 99% sensitivity and specificity in 4% of fetal DNA or circulating cell-free DNA, using a non-allelic method, requires 110,414 total target loci. This can be achieved using 0.5 ml of plasma, a plurality of at least 1000 loci, and a sample prep method that retains at least 25% of the initial total target loci using a set of at least 32 MITs. Thus, in this example, the effective amount is at least 1000 loci and at least 0.5 ml of plasma.

In some embodiments, determining the number of copies of the one or more chromosomes or chromosome segments of interest can include comparing the quantity of DNA at the plurality of target loci to a quantity of DNA at a plurality of disomic loci on one or more chromosomes or chromosome segments expected to be disomic. The quantity of DNA at the plurality of disomic loci can be determined in the same manner as the plurality of target loci, i.e. determining the sequences of the attached MITs and at least a portion of the sample nucleic acid segments of the tagged nucleic acid molecules in the library of tagged nucleic acid molecules and using the determined sequences to determine the identity of a sample nucleic acid molecule that gave rise to a tagged nucleic acid molecule and measuring a quantity of DNA for each target locus by counting the number of sample nucleic acid molecules that comprise each target locus using the determined identities. In some embodiments, the plurality of disomic loci on the one or more chromosomes or chromosome segments expected to be disomic can be SNP loci.

In any of the embodiments disclosed herein, the number of loci in the plurality of target loci can be between 10, 20, 30, 40, 50, 60, 70, 80, 90, 100, 200, 300, 400, 500, 600, 700, 800, 900, 1,000, 2,000, 3,000, 4,000, and 5,000 loci on the low end of the range and 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, and 100,000 loci on the high end of the range. In some embodiments, the number of target loci are at least 1,000, 2,000, 3,000, 4,000, 5,000, 6,000, 7,000, 8,000, 9,000, or 10,000 loci. In any of the embodiments disclosed herein, the number of loci in the plurality of disomic loci can be between 10, 20, 30, 40, 50, 60, 70, 80, 90, 100, 200, 300, 400, 500, 600, 700, 800, 900, 1,000, 2,000, 3,000, 4,000, and 5,000 loci on the low end of the range and 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, and 100,000 loci on the high end of the range. In some embodiments, the number of disomic loci are at least 1,000, 2,000, 3,000, 4,000, 5,000, 6,000, 7,000, 8,000, 9,000, or 10,000 loci.

In various embodiments, a set of hypotheses concerning the number of copies of the one or more chromosomes or chromosome segments of interest can be generated to compare the measured quantity of DNA to an expected quantity of DNA based on each particular hypothesis. In the context of this disclosure, a hypothesis can refer to a copy number of a chromosome or chromosome segment of interest. It may refer to a possible ploidy state. It may refer to a possible allelic state or allelic imbalance. In some embodiments, a set of hypotheses may be designed such that one hypothesis from the set will correspond to the actual genetic state of any given individual. In some embodiments, a set of hypotheses may be designed such that every possible genetic state may be described by at least one hypothesis from the set. In some embodiments, of the present disclosure, the method can determine which hypothesis corresponds to the actual genetic state of the individual in question. In some embodiments, the set of hypotheses may include hypotheses of fetal fraction in addition to the possible genetic state. In some embodiments, the set of hypotheses may include hypotheses of in average allelic imbalance in addition to the possible genetic state.

In some embodiments, a joint distribution model can be used to determine a relative probability of each hypothesis. A joint distribution model is a model that defines the probability of events defined in terms of multiple random variables, given a plurality of random variables defined on the same probability space, where the probabilities of the variable are linked. In some embodiments, the degenerate case where the probabilities of the variables are not linked may be used. In various embodiments of the present disclosure, determining the number of copies of one or more chromosomes or chromosome segments of interest in a sample also includes combining the relative probabilities of each of the ploidy hypotheses determined using the joint distribution model with relative probabilities of each of the ploidy hypotheses that are calculated using statistical techniques taken from a group consisting of a read count analysis, comparing heterozygosity rates, the probability of normalized genotype signals for certain parent contexts, and combinations thereof. In various embodiments, the joint distribution can combine the relative probabilities of each of the ploidy hypotheses with the relative probabilities of each of the fetal fraction hypotheses. In some embodiments, of the present disclosure, determining the relative probability of each hypothesis can make use of an estimated fraction of the DNA in the sample. In various embodiments, the joint distribution can combine the relative probabilities of each of the ploidy hypotheses with the relative probabilities of each of the allelic imbalance hypotheses. In some embodiments, determining the copy number of one or more chromosomes or chromosome segments of interests includes selecting the hypothesis with the greatest probability, which is carried out using a maximum likelihood estimate technique or a maximum a posteriori technique.

Maximum Likelihood and Maximum a Posteriori Estimates

Most methods known in the art for detecting the presence or absence of biological phenomenon or medical condition involve the use of a single hypothesis rejection test, where a metric that is correlated with the condition is measured, and if the metric is on one side of a given threshold, the condition is present, while of the metric falls on the other side of the threshold, the condition is absent. A single-hypothesis rejection test only looks at the null distribution when deciding between the null and alternate hypotheses. Without taking into account the alternate distribution, one cannot estimate the likelihood of each hypothesis given the observed data and therefore one cannot calculate a confidence on the call. Hence with a single-hypothesis rejection test, one gets a yes or no answer without a feeling for the confidence associated with the specific case.

In some embodiments, the method disclosed herein is able to detect the presence or absence of biological phenomenon or medical condition using a maximum likelihood method. This is a substantial improvement over a method using a single hypothesis rejection technique as the threshold for calling absence or presence of the condition can be adjusted as appropriate for each case. This is particularly relevant for diagnostic techniques that aim to determine the presence or absence of aneuploidy in a gestating fetus from genetic data available from the mixture of fetal and maternal DNA present in the free floating DNA found in maternal plasma. This is because as the fraction of fetal DNA in the plasma derived fraction changes, the optimal threshold for calling aneuploidy versus euploidy changes. As the fetal fraction drops, the distribution of data that is associated with an aneuploidy becomes increasingly similar to the distribution of data that is associated with a euploidy.

The maximum likelihood estimation method uses the distributions associated with each hypothesis to estimate the likelihood of the data conditioned on each hypothesis. These conditional probabilities can then be converted to a hypothesis call and confidence. Similarly, the maximum a posteriori estimation method uses the same conditional probabilities as the maximum likelihood estimate, but also incorporates population priors when choosing the best hypothesis and determining confidence. Therefore, the use of the maximum likelihood estimate (MLE) technique or the closely related maximum a posteriori (MAP) technique gives two advantages, first it increases the chance of a correct call, and it also allows a confidence to be calculated for each call.

Exemplary Methods of Determining the Number of Sample Nucleic Acid Molecules

A method is disclosed herein to determine the number of DNA molecules in a sample by generating a tagged nucleic acid molecule from each sample nucleic acid molecule by incorporating two MITs. Disclosed here is a procedure to accomplish the above end followed by a single molecule or clonal sequencing method.

As detailed herein, the approach entails generating tagged nucleic acid molecules such that most or all of the tagged nucleic acid molecules from each locus have different combinations of MITs and can be identified upon sequencing of the MITs using clonal or single molecule sequencing. The identification can optionally use the mapped locations of the nucleic acid segments. Each combination of MITs and nucleic acid segment represents a different sample nucleic acid molecule. Using this information one can determine the number of individual sample nucleic acid molecules in the original sample for each locus.

This method can be used for any application in which quantitative evaluation of the number of sample nucleic acid molecules is required. Furthermore, the number of individual nucleic acid molecules from one or more target loci can be related to the number of individual nucleic acid molecules from one or more disomic loci to determine the relative copy number, copy number variation, allele distribution, allele ratio, allelic imbalance, or average allelic imbalance. Alternatively, the number of copies detected from various targets can be modeled by a distribution in order to identify the mostly likely number of copies of the target loci. Applications include but are not limited to detection of insertions and deletions such as those found in carriers of Duchenne Muscular Dystrophy; quantitation of deletions or duplications segments of chromosomes such as those observed in copy number variants; determination of chromosome copy number of samples from born individuals; and determination of chromosome copy number of samples from unborn individuals such as embryos or fetuses.

The method can be combined with simultaneous evaluation of variations contained in the determined sequences. This can be used to determine the number of sample nucleic acid molecules representing each allele in the original sample. This copy number method can be combined with the evaluation of SNPs or other sequence variations to determine the copy number of chromosomes or chromosome segments of interest from born or unborn individuals; the discrimination and quantification of copies from loci which have short sequence variations, but in which PCR may amplify from multiple target loci such as in carrier detection of Spinal Muscle Atrophy; and determination of copy number of different sources of nucleic acid molecules from samples consisting of mixtures of different individuals such as in the detection of fetal aneuploidy from free floating DNA obtained from maternal plasma.

In any of the embodiments disclosed herein the method may comprise one or more of the following steps: (1) Attaching Y-adaptor nucleic acid molecules with MITs to a population of sample nucleic acid molecules by ligation. (2) Performing one or more rounds of amplification. (3) Using hybrid capture to enrich target loci. (4) Measuring the amplified PCR product by a multitude of methods, for example, clonal sequencing, to a sufficient number of bases to span the sequence.

In any of the embodiments disclosed herein the method as it pertains to a single target locus may comprise one or more of the following steps: (1) Designing a standard pair of oligomers for amplification of a specific locus. (2) Adding, during synthesis, a sequence of specified bases, with no or minimal complementarity to the target locus or genome, to the 5' end of both of the target specific PCR primers. This sequence, termed the tail, is a known sequence, to be used for subsequent amplification, followed by an MIT. Consequently, following synthesis, the tailed PCR primer pool will consist of a collection of oligomers beginning with a known sequence followed by the MIT, followed by the target specific sequence. (3) Performing one round of amplification (denaturation, annealing, extension) using only the tailed oligomer. (4) Adding exonuclease to the reaction, effectively stopping the PCR reaction, and incubating the reaction at the appropriate temperature to remove forward single stranded oligos that did not anneal to temple and extend to form a double stranded product. (5) Incubating the reaction at a high temperature to denature the exonuclease and eliminate its activity. (6) Adding to the reaction a new oligonucleotide that is complementary to the tail of the oligomer used in the first reaction along with the other target specific oligomer to enable PCR amplification of the product generated in the first round of PCR. (7) Continuing amplification to generate enough product for downstream clonal sequencing. (8) Measuring the amplified PCR product by a multitude of methods, for example, clonal sequencing, to a sufficient number of bases to span the sequence.

In some embodiments, the design and generation of primers with MITs may be reduced to practice as follows: the primers with MITs may consist of a sequence that is not complementary to the target sequence followed by a region with the MIT followed by a target specific sequence. The sequence 5' of the MIT may be used for subsequent PCR amplification and may comprise sequences useful in the conversion of the amplicon to a library for sequencing. In some embodiments, the DNA can be measured by a sequencing method, where the sequence data represents the sequence of a single molecule. This can include methods in which single molecules are sequenced directly or methods in which single molecules are amplified to form clones detectable by the sequence instrument, but that still represent single molecules, herein called clonal sequencing.

In some embodiments, a method of the present disclosure involves targeting multiple loci in parallel or otherwise. Primers to different target loci can be generated independently and mixed to create multiplex PCR pools. In some embodiments, original samples can be divided into subpools and different loci can be targeted in each sub-pool before being recombined and sequenced. In some embodiments, the tagging step and a number of amplification cycles may be performed before the pool is subdivided to ensure efficient targeting of all targets before splitting, and improving subsequent amplification by continuing amplification using smaller sets of primers in subdivided pools.

For example, imagine a heterozygous SNP in the genome of an individual, and a mixture of DNA from the individual where ten sample nucleic acid molecules of each allele are present in the original sample of DNA. After MIT incorporation and amplification there may be 100,000 tagged nucleic acid molecules corresponding to that locus. Due to stochastic processes, the ratio of DNA could be anywhere from 1:2 to 2:1, however, since each of the sample nucleic acid molecules was tagged with MITs, it would be possible to determine that the DNA in the amplified pool originated from exactly 10 sample nucleic acid molecules from each allele. This method would therefore give a more accurate measure of the relative amounts of each allele than a method not using this approach. For methods where it is desirable for the relative amount of allele bias to be minimized, this method will provide more accurate data.

Association of the sequenced fragment to the target locus can be achieved in a number of ways. In some embodiments, a sequence of sufficient length is obtained from the targeted fragment to span the MIT as well a sufficient number of unique bases corresponding to the target sequence to allow unambiguous identification of the target locus. In other embodiments, the MIT primer that contains the MIT can also contain a locus specific barcode (locus barcode) that identifies the target to which it is to be associated. This locus barcode would be identical among all MIT primers for each individual target locus and hence all resulting amplicons, but different from all other loci. In some embodiments, the tagging method disclosed herein may be combined with a one-sided nesting protocol.

One example of an application where MITs would be particularly useful for determining copy number is non-invasive prenatal aneuploidy diagnosis where the quantity of DNA at a target locus or plurality of target loci can be used to help determine the number of copies of one or more chromosomes or chromosome segment of interest in a fetus. In this context, it is desirable to amplify the DNA present in the initial sample while maintaining the relative amounts of the various alleles. In some circumstances, especially in cases where there is a very small amount of DNA, for example, fewer than 5,000 copies of the genome, fewer than 1,000 copies of the genome, fewer than 500 copies of the genome, and fewer than 100 copies of the genome, one can encounter a phenomenon called bottlenecking. This is where there are a small number of copies of any given allele in the initial sample, and amplification biases can result in the amplified pool of DNA having significantly different ratios of those alleles than are in the initial mixture of DNA. By using MITs on each strand of DNA before standard PCR amplification, it is possible to exclude n−1 copies of DNA from a set of n identical sequenced tagged nucleic acid molecules in the library that originated from the same sample nucleic acid molecule. In this manner, any allelic bias or amplification bias can be removed from further analysis. In various embodiments, of the present disclosure, the method may be performed for fetuses at between 4 and 5 weeks gestation; between 5 and 6 weeks gestation; between 6 and 7 weeks gestation; between 7 and 8 weeks gestation; between 8 and 9 weeks gestation; between 9 and 10 weeks gestation; between 10 and 12 weeks gestation; between 12 and 14 weeks gestation; between 14 and 20 weeks gestation; between 20 and 40 weeks gestation; in the first trimester; in the second trimester; in the third trimester; or combinations thereof.

Another application where MITs would be particularly useful for determining copy number or average allelic imbalance is non-invasive cancer diagnosis where the amount of genetic material at a locus or a plurality of loci can be used to help determine copy number variations or average allelic imbalances. Allelic imbalance for aneuploidy determinations, such as copy number variant determinations, refers to the difference between the frequencies of the alleles for a locus. It is an estimate of the difference in the numbers of copies of the homologs. Allelic imbalance can arise from the complete loss of an allele or from an increase in copy number of one allele relative to the other. Allelic imbalances can be detected by measuring the proportion of one allele relative to the other in fluids or cells from individuals that are constitutionally heterozygous at a given locus. (Mei et al, Genome Res, 10:1126-37 (2000)). For dimorphic SNPs that have alleles arbitrarily designated 'A' and 'B', the allele ratio of the A allele is nA/(nA+nB), where nA and nB are the number of sequencing reads for alleles A and B, respectively. Allelic imbalance is the difference between the allele ratios of A and B for loci that are heterozygous in the germline. This definition is analogous to that for SNVs, where the proportion of abnormal DNA is typically measured using mutant allele frequency, or nm/(nm+nr), where nm and nr are the number of sequencing reads for the mutant allele and the reference allele, respectively. Accordingly, the proportion of abnormal DNA for a CNV can be measured by the average allelic imbalance (AAI), defined as |(H1−H2)|/(H1+H2), where Hi is the average number of copies of homolog i in the sample and Hi/(H1+H2) is the fractional abundance, or homolog ratio, of homolog i. The maximum homolog ratio is the homolog ratio of the more abundant homolog.

Accurately Measuring the Allelic Distributions in a Sample

Current sequencing approaches can be used to estimate the distribution of alleles in a sample. One such method involves randomly sampling sequences from a pool DNA, termed shotgun sequencing. The proportion of a particular allele in the sequencing data is typically very low and can be determined by simple statistics. The human genome contains approximately 3 billion base pairs. So, if the sequencing method used make 100 bp reads, a particular allele will be measured about once in every 30 million sequence reads.

In some embodiments, a method of the present disclosure is used to determine the presence or absence of two or more different haplotypes that contain the same set of loci in a sample of DNA from the measured allele distributions of loci from that chromosome. The different haplotypes could represent two different homologous chromosomes from one source, three different homologous chromosomes from one, three different homologous haplotypes in a sample comprising a mixture of two genetically distinct genomes where one of the haplotypes is shared between the genetically distinct genomes, three or four haplotypes in a sample comprising a mixture of two genetically distinct genomes where one or two of the haplotypes are shared between the genetically distinct genomes, or other combinations. Alleles that are polymorphic between the haplotypes tend to be more informative, however any alleles where the genetically distinct genomes are not both homozygous for the same allele will yield useful information through measured allele distributions beyond the information that is available from simple read count analysis.

Shotgun sequencing of such a sample, however, is extremely inefficient as it results in reads for many sequences from loci that are not polymorphic between the different haplotypes in the sample, or are for chromosomes that are not of interest, and therefore reveal no information about the proportion of the target haplotypes. Disclosed herein are methods that specifically target and/or preferentially enrich segments of DNA in the sample that are more likely to be polymorphic in the genome to increase the yield of allelic information obtained by sequencing. Note that for the measured allele distributions in an enriched sample to be truly representative of the actual amounts present in the target individual, it is critical that there is little or no preferential enrichment of one allele as compared to the other allele at a given locus in the targeted segments. Current methods known in the art to target polymorphic alleles are designed to ensure that at least some of any alleles present are detected. However, these methods were not designed for the purpose of measuring the unbiased allelic distributions of polymorphic alleles present in the original mixture. It is difficult to predict that a particular method of target enrichment would produce an enriched sample wherein the measured allele distributions would accurately represent the allele distributions present in the original unamplified sample better than another method. While many enrichment methods may be expected, in theory, to accomplish such an aim, there is a great deal of stochastic bias in current amplification, targeting, and other preferential enrichment methods. One embodiment of a method disclosed herein allows a plurality of alleles found in a mixture of DNA that correspond to a given locus in the genome to be amplified, or preferentially enriched in a way that the degree of enrichment of each of the alleles is nearly the same. Another way to say this is that the method allows the relative quantity of the alleles present in the mixture as a whole to be increased, while the ratio between the alleles that correspond to each locus remains essentially the same as they were in the original mixture of DNA. For some reported methods, preferential enrichment of loci can result in allelic biases of more than 1%, more than 2%, more than 5% and even more than 10%. This preferential enrichment may be due to capture bias when using a hybrid capture approach, or amplification bias which may be small for each cycle, but can become large when compounded over 20, 30, or 40 cycles. For the purposes of this disclosure, for the ratio to remain essentially the same means that the ratio of the alleles in the original mixture divided by the ratio of the alleles in the resulting mixture is between 0.95 and 1.05, between 0.98 and 1.02, between 0.99 and 1.01, between 0.995 and 1.005, between 0.998 and 1.002, between 0.999 and 1.001, or between 0.9999 and 1.0001. Note that the calculation of the allele ratios presented here may not be used in the determination of the ploidy state of the target individual, and may only be used as a metric to measure allelic bias. The use of MITs can be used to remove errors due to capture bias, amplification bias, and allelic bias as the number of sample nucleic acid molecules can be specifically counted using the methods disclosed herein.

In some embodiments, once a mixture has been preferentially enriched at the set of target loci, it may be sequenced using any one of the previous, current, or next generation of sequencing instruments as discussed in more detail herein. The ratios can be evaluated by sequencing through the specific alleles within the chromosome or chromosome segment of interest. These sequencing reads can be analyzed and counted according the allele type and the ratios of different alleles determined accordingly. For variations that are one to a few bases in length, detection of the alleles will be performed by sequencing and it is essential that the sequencing read span the allele in question in order to evaluate the allelic composition of that captured molecule. The total number of captured nucleic acid molecules assayed for the genotype can be increased by increasing the length of the sequencing read. Full sequencing of all tagged nucleic acid molecules would guarantee collection of the maximum amount of data available in the enriched pool. However, sequencing is currently expensive, and a method that can measure allele distributions using a lower number of sequence reads will have great value. In addition, there are technical limitations to the maximum possible length of read as well as accuracy limitations as read lengths increase. The alleles of greatest utility will be of one to a few bases in length, but theoretically any allele shorter than the length of the sequencing read can be used. Larger variants such as segmental copy number variants can be detected by aggregations of these smaller variations in many cases as whole collections of SNP internal to the segment are duplicated.

Variants larger than a few bases, such as STRs require special consideration and some targeting approaches work while others will not.

There are multiple targeting approaches that can be used to specifically isolate and enrich one or a plurality of variant positions in the genome. Typically, these rely on taking advantage of the invariant sequence flanking the variant sequence. There are reports by others related to targeting in the context of sequencing where the substrate is maternal plasma (see, e.g., Liao et al., Clin. Chem. 2011; 57(1): pp. 92-101). However, these approaches use targeting probes that target exons, and do not focus on targeting polymorphic loci of the genome. In various embodiments, a method of the present disclosure involves using targeting probes that focus exclusively or almost exclusively on polymorphic loci. In some embodiments, a method of the present disclosure involves using targeting probes that focus exclusively or almost exclusively on SNPs. In some embodiments, of the present disclosure, the targeted polymorphic sites consist of at least 10% SNPs, at least 20% SNPs, at least 30% SNPs, at least 40% SNPs, at least 50% SNPs, at least 60% SNPs, at least 70% SNPs, at least 80% SNPs, at least 90% SNPs, at least 95% SNPs, at least 98% SNPs, at least 99% SNPs, at least 99.9% SNPs, or exclusively SNPs.

In some embodiments, a method of the present disclosure can be used to determine genotypes (base composition of the DNA at specific loci) and relative proportions of those genotypes from a mixture of DNA molecules, where those DNA molecules may have originated from one or a number of genetically distinct genomes. In some embodiments, a method of the present disclosure can be used to determine the genotypes at a set of polymorphic loci, and the relative ratios of the amounts of different alleles present at those loci. In some embodiments, the polymorphic loci may consist entirely of SNPs. In some embodiments, the polymorphic loci can comprise SNPs, single tandem repeats, and other polymorphisms. In some embodiments, a method of the present disclosure can be used to determine the relative distributions of alleles at a set of polymorphic loci in a mixture of DNA, where the mixture of DNA comprises DNA that originates from an individual and from a tumor growing in that individual.

In some embodiments, the mixture of DNA molecules could be derived from DNA extracted from multiple cells of one individual. In some embodiments, the original collection of cells from which the DNA is derived may comprise a mixture of diploid or haploid cells of the same or of different genotypes, if that individual is mosaic (germline or somatic). In some embodiments, the mixture of nucleic acid molecules could also be derived from DNA extracted from single cells. In some embodiments, the mixture of DNA molecules could also be derived from DNA extracted from a mixture of two or more cells of the same individual, or of different individuals. In some embodiments, the mixture of DNA molecules could be derived from cell-free DNA, such as present in blood plasma. In some embodiments, this biological material may be a mixture of DNA from one or more individuals, as is the case during pregnancy where it has been shown that fetal DNA is present in the mixture or in cancer, when tumor DNA and can be present in the blood plasma. In some embodiments, the biological material could be from a mixture of cells that were found in maternal blood, where some of the cells are fetal in origin. In some embodiments, the biological material could be cells from the blood of a pregnant which have been enriched in fetal cells.

The algorithm used to determine the number of copies of one or more chromosomes or chromosome segments of interest can consider parental genotypes and crossover frequency data (such as data from the HapMap database) to calculate expected allele distributions for the target loci for a very large number possible fetal ploidy states, and at various fetal cfDNA fractions. Unlike allele ratio based-methods, it can also take into account linkage disequilibrium and use non-Gaussian data models to describe the expected distribution of allele measurements at a SNP given observed platform characteristics and amplification biases. The algorithm can then compare the various predicted allele distributions to the actual allelic distributions as measured in the sample, and can calculate the likelihood of each hypothesis (monosomy, disomy, or trisomy, for which there are numerous hypotheses based on the various potential crossovers) based on the sequencing data. The algorithm sums the likelihoods of each individual monosomy, disomy, or trisomy hypothesis and calls the hypothesis with the maximum overall likelihood as the copy number and fetal fraction. A similar algorithm can be used to determine the average allelic imbalance in a sample and a skilled artisan will understand how to modify the method.

The following examples are put forth so as to provide those of ordinary skill in the art with a complete disclosure and description of how to use the embodiments provided herein, and are not intended to limit the scope of the disclosure nor are they intended to represent that the Examples below are all or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described can be made without changing the fundamental aspects that the Examples are meant to illustrate.

EXAMPLES

Example 1. Exemplary Workflow for Identifying Sample Nucleic Acid Molecules

Figure 3A:
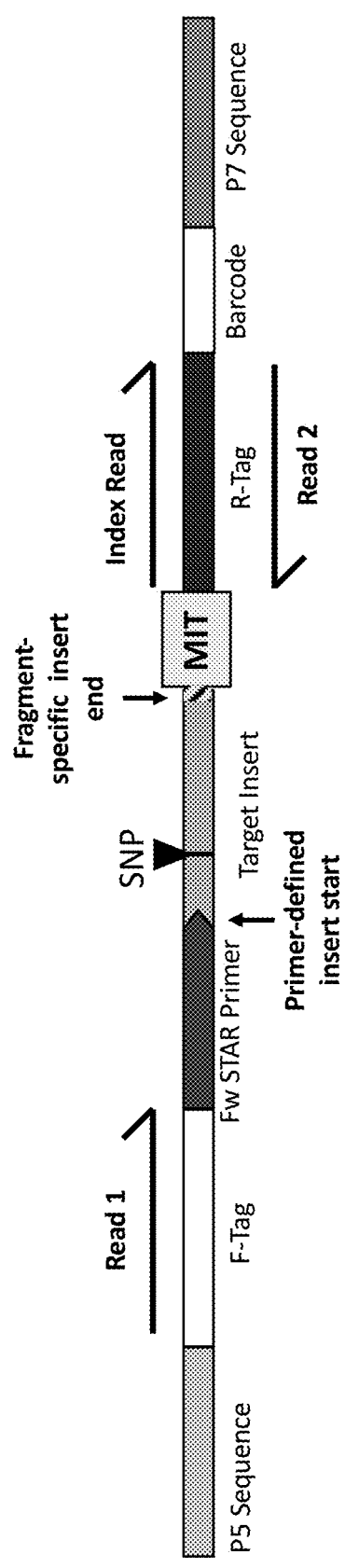
FIGS. 3A-3B illustrate the structures of amplicons produced by different exemplary methods provided herein. The amplicon generated after 1-sided STAR (FIG. 3A) has an MIT on one side wherein the first base of the MIT is the first base in Read 1 or Read 2 depending on how 1-sided STAR is performed.
Figure 3B:
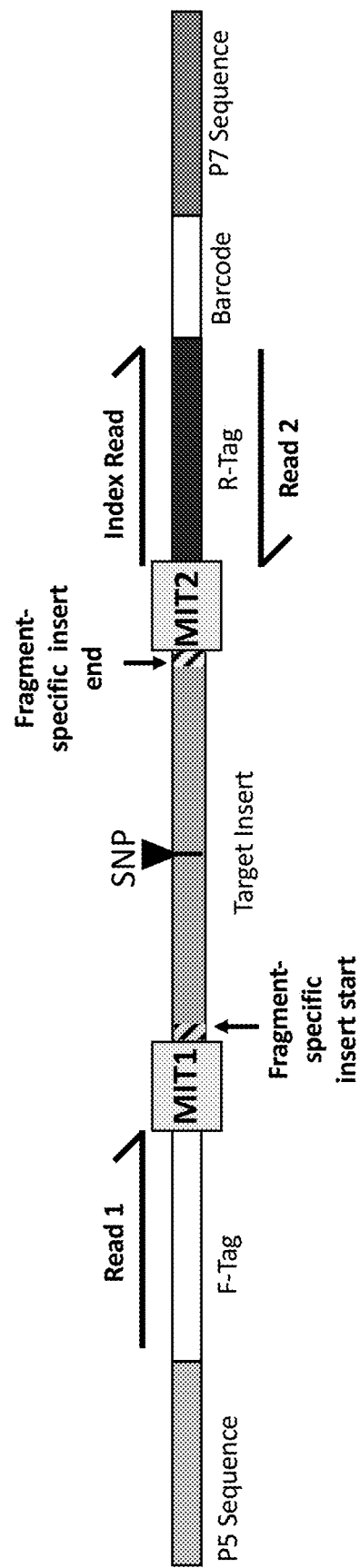

Provided herein is an example of a method for identifying sample nucleic acid molecules after amplification of such molecules in a high-throughput sequencing workflow. The structure of a non-limiting exemplary amplicon produced using such a method is shown in FIG. 3. A set of nucleic acid samples are prepared by isolating nucleic acids from a natural source. For example, circulating cell-free DNA can be isolated from samples of blood, or a fraction thereof, from target patients using known methods. Some of the sample nucleic acids in the blood can include one or more target sites. Sample nucleic acid molecules are processed so that any overhangs are removed in a blunt end repair reaction using Klenow large fragment, and polynucleotide kinase is used to ensure that all 5' ends are phosphorylated. A 3' adenosine residue is added to the blunt end repaired sample nucleic acid molecules using Klenow Fragment (exo−) to increase ligation efficiency. A set of 206 MITs that are 6 nucleotides in length, each having at least 2 base difference from all other MITs, are then designed to be included in the double-stranded polynucleotide sequence adjacent to the 3' T overhang of a standard high-throughput sequencing Y-adapter, as illustrated in FIG. 1. The set of Y-adapters each including a different MIT are then ligated to both ends of each sample nucleic acid molecule using a ligase, in a ligation reaction to produce a population of tagged nucleic acid molecules. For the ligation reaction 10,000 sample nucleic acid molecules are tagged with the library of 206 MIT-containing Y-adapters. The resulting population of tagged nucleic acid molecules includes a Y-adapter with an MIT ligated to both ends of the sample nucleic acid molecule as illustrated in FIG. 1, such that the MITs are ligated to the ends of the sample nucleic acid segment, also called the insert, of the tagged nucleic acid molecule.

A library of tagged nucleic acid molecules is then prepared by amplifying the population of tagged nucleic acid molecules using universal primers that bind to primer binding sites on the Y-adapters. A target enrichment step is then performed to isolate and amplify tagged nucleic acid molecules that include sample nucleic acid segments with target SNPs. The target enrichment can be performed using a one-sided PCR reaction or hybrid capture. Either of these target enrichment reactions can be a multiplex reaction using a population of primers (one-sided PCR) or probes (hybrid capture) that are specific for a sample nucleic acid segment that includes a target SNP. One or more additional PCR reactions are then performed using universal primers that include a different barcode sequence for each patient sample, as well as clonal amplification and sequencing primer binding sequences (R-Tag and F-Tag in FIG. 3). The structure of resulting amplified tagged nucleic acid molecules is shown schematically in FIG. 3.

The amplified tagged nucleic acid molecules are then clonally amplified onto a solid support using universal sequences added during one of the amplification reactions. The sequence of the clonally amplified tagged nucleic acid molecules is then determined on a high-throughput sequencing instrument, such as an Illumina sequencing instrument. For tagged nucleic acid molecules enriched using one-sided PCR, the MIT on the right side of the sample nucleic acid segment (i.e. insert) is the first base read by one of the sequencing reads. For tagged nucleic acid molecules enriched using hybrid capture, one MIT remains on each side of the sample nucleic acid segment (i.e. insert) and the first base of a first ligated MIT on one end of the sample nucleic acid segment is the first base read in a first read and the second ligated MIT at the other end of the sample nucleic acid segment is the first base read in a second read. The resulting sequencing reads are then analyzed. The sequences of the fragment-specific insert ends are used to map the locations of each end of the nucleic acid segment to specific locations in the genome of the organism and these locations can be used in combination with the MITs to identify each tagged nucleic acid molecule. This information is then analyzed using commercially available software packages that are programmed to differentiate true sequence differences in sample nucleic acid molecules from errors that were introduced during any of the sample preparation amplification reactions.

Example 2. Reduction of Error Rate Using MITs on Sample Nucleic Acid Molecules

Provided herein is an example demonstrating the reduction of error rates provided by using MITs to identify amplification errors in a high-throughput sequencing sample preparation workflow. Three separate experiments were performed where, in each experiment, two independent DNA samples with $2\times10^{11}$ total sample nucleic acid molecules including 10,000 input copies of the human genome (10,000 copies×(3,000,000,000 bp/genome)/(150 bp/nucleic acid molecule)=$2\times10^{11}$ total sample nucleic acid molecules) in 58 µl (5.75 nM final concentration) were used to generate a library of tagged nucleic acid molecules with an MIT at the 5' end and an MIT at the 3' end as disclosed herein. A set of 196 MITs was used for this experiment at a concentration between 0.5 and 2 µM such that the ratio of the total number of MITs in the reaction mixtures to the total number of sample nucleic acid molecules in the reaction mixtures was between ~85:1 and ~350:1. As indicated, only 196 MITs, or about 40,000 combinations of two MITs, were used for a sample having $2\times10^{11}$ total sample nucleic acid molecules.

In each experiment the libraries were enriched for tagged nucleic acid molecules containing TP53 exons by performing hybrid capture with a commercially available kit. The enriched libraries were then amplified by PCR using universal primers that could bind to universal primer binding sequences that had been previously incorporated into the tagged nucleic acid molecules. The universal primers included different barcode sequences for each sample as well as additional sequences to enable sequencing on an Illumina HiSeq 2500. For each experiment the samples were then pooled and paired-end sequencing was performed on a HiSeq 2500 in rapid mode for 150 cycles in each the forward and reverse read.

Sequencing data were demultiplexed using commercially available software. From each sequencing read, data for bases the length of the MIT plus the T overhang (seven nucleotides in total in these experiments) were trimmed from the start of the read and recorded. The remaining trimmed read data were then merged and mapped to the human genome. Fragment end positions for each read were recorded. All reads with at least one base covering the target locus (TP53 exons) were considered on-target reads. The mean depths of read were calculated on a per base level across the target locus. Mean error rates (expressed as percentages) were calculated by counting all base calls across the target locus that did not correspond to the reference genome (GRCh37) and dividing these by the total base calls across the target locus. For each base position in the target locus, sequencing data were then grouped into MIT families where each MIT family shared identical MITs in the same relative position to the analyzed base position as well as the same fragment end positions and the same sequenced orientation (positive or negative relative to the human genome). Each of these families represented groupings of molecules that are likely clonal amplifications of the same sample nucleic acid molecule that entered the MIT library preparation process. Each sample nucleic acid molecule that entered into the MIT library preparation process should have generated two families, one mapping to each of the positive and negative genomic orientations. Paired MIT nucleic acid segment families were then generated using two MIT families, one with a positive orientation and one with a negative orientation where each family contained complementary MITs in the same relative position to the analyzed base position as well as the complementary fragment end positions. These paired MIT families represented groupings of sequenced molecules that are even more likely to be clonal amplifications of the same sample nucleic acid molecule that entered the MIT library preparation process. Mean error rates (expressed as percentages) were then calculated by counting all base calls within all paired MIT nucleic acid segment families across the target locus that did not correspond to the reference genome (GRCh37) and dividing these by the total base calls within all paired MIT families across the target locus.

Figure 5:
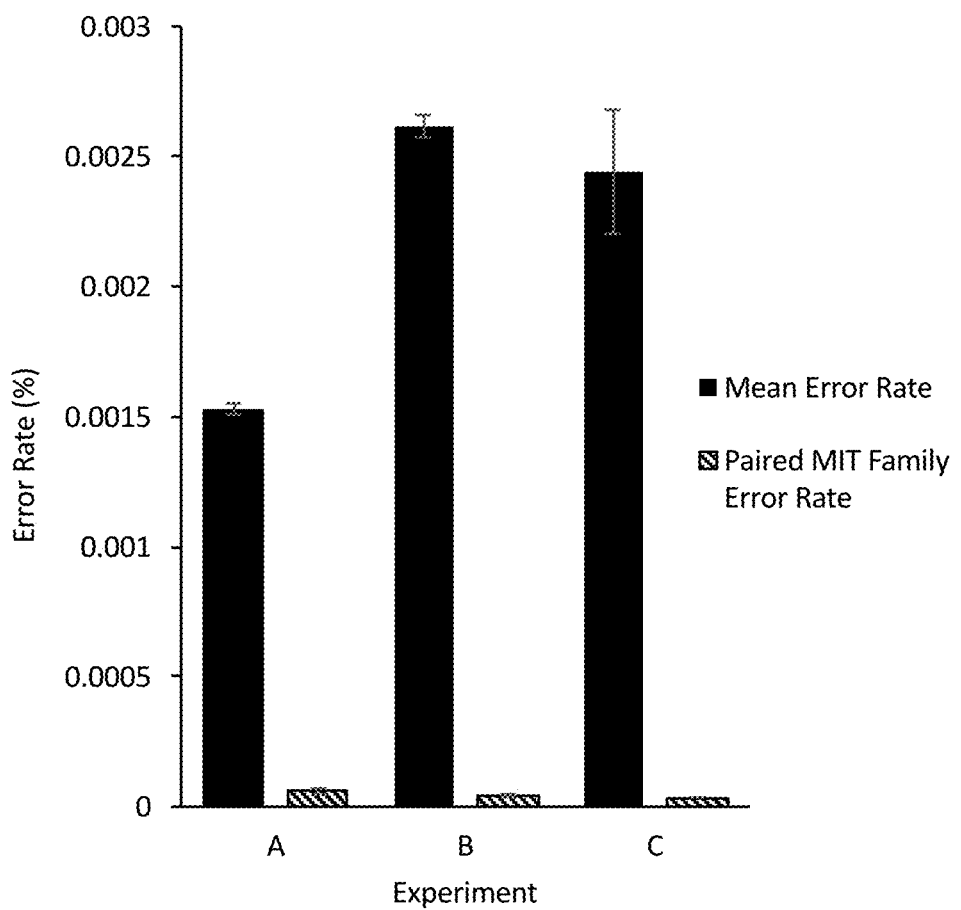
FIG. 5 is a bar graph that shows the average error rate and the average paired MIT nucleic acid segment family error rate of two samples in three different experimental runs (data from FIG. 4).

FIG. 4 shows the results of the three experiments. Each sample contained 33 ng of DNA representing 10,000 input copies of the haploid human genome. Sequencing data from these experiments yielded between 4.4 million and 10.7 million mapped reads per sample and 3.0 million to 7.8 million on-target reads per sample. The proportion of on-target reads to mapped reads ranged from 68% to 74%. The mean depth of read across the target loci ranged from ~98,000 to ~244,000 depth of read. Mean error rates ranged from 0.15% to 0.26% if all the data was included. Mean error rates calculated using data from only the paired MIT nucleic acid segment families ranged from 0.0036% to 0.0067%. The average mean error rate and paired MIT nucleic acid segment family error rate of the two samples in each experiment show the drastic reduction in error rate when paired MIT nucleic acid segment families are used (FIG. 5). The residual errors observed here are likely due to single nucleotide polymorphisms in the samples as these positions were not excluded. The paired MIT nucleic acid segment family error rates were 23 to 73 times lower than their original error rates. Notably, experiments B and C, which had higher original error rates compared to experiment A, experienced greater reductions in error rates when calculated using the paired MIT families. These results demonstrate the utility of MITs for removal of errors.

Example 3. Mathematical Analysis Demonstrating Low Sample Volumes for Determining Copy Numbers Using MITs This example provides an analysis of the number of target loci and plasma sample volume that provides an effective amount of total target loci to achieve a desired sensitivity and a desired specificity for a copy number determination using MITs. In a sample with a mixture of two genomes, G1 and G2, the copy numbers of chromosomes or chromosome segments of interest can be determined for one of the genomes. G1 and G2 can have various copy numbers of chromosomes of interest, for example, two copies of each chromosome in a set of chromosomes, one copy of another set, etc. Suppose G2 has one or more reference chromosomes or chromosome segments on its genome with known copy numbers (typically one or more chromosomes or chromosome segments expected to be disomic) and one or more chromosomes or chromosome segments of interest on its genome with unknown copy numbers (although the possible copy numbers are assumed to be known). The copy number of G2 of a chromosome or chromosome segment of interest where the true copy number is unknown can be estimated (given the set of possible copy numbers are known). Note that the copy numbers of G1 is known on both reference chromosomes or chromosome segments and chromosomes or chromosome segments of interest. The measurement technology is modeled as capturing a nucleic acid molecule and identifying whether it belongs to the one or more reference chromosomes or chromosome segments or the one or more chromosomes or chromosome segments of interest, where there is probability of error.

Assuming that the sample contains a finite number of nucleic acid molecules, we can sample nucleic acid molecules until we have a good estimate of the number of nucleic acid molecules in the sample that belong to the one or more reference chromosomes or chromosome segments and the one or more chromosomes or chromosome segments of interest. Using an estimate of the fraction of G2 in the sample, test statistics for different copy number hypotheses of G2 in the one or more chromosomes or chromosome segments of interest can be calculated as demonstrated below.

Method 1 Quantitative Non-Allelic Method

In this method, the number of sample nucleic acid molecules are compared for the one or more reference chromosomes or chromosome segments versus the one or more chromosomes or chromosome segments of interest. The assumptions are that when tagged nucleic acid molecules are sequenced, there is an equal probability of sequencing a tagged nucleic acid molecule from the one or more reference chromosomes or chromosome segments and the one or more chromosomes or chromosome segments of interest. Denote this probability with p, where p=0.5. An example of a test statistic that can be used is the ratio of number of nucleic acid molecules from the one or more chromosomes or chromosome segments of interest ($n_t$) to the total number of observed nucleic acid molecules (n):

$$T = \frac{n_t}{n}$$

For n>20, the distribution of T can be approximated by a normal distribution, with variance $$\frac{p(1-p)}{n} = \frac{0.25}{n} \text{ for } p = 0.5.$$

The mean of the distribution depends on the copy number hypothesis of G2 being tested and by getting more observations (i.e., by lowering the variance), one can increase the accuracy of the results. This allows for creating an estimator that achieves particular sensitivity and specificity.

Suppose that G2 represents 4% of the sample mixture (and G1 is 96% of the mixture). Further, assume that G1 has two copies of each locus in both the reference chromosomes or chromosome segments and chromosomes or chromosome segments of interest. Also, assume that G2 has two copies of each locus in the one or more reference chromosomes or chromosome segments. We want to consider two hypotheses: H2, where G2 has two copies of each locus in a chromosome or chromosome segment of interest and H3, where G2 has three copies of each locus in the chromosome or chromosome segment of interest. As mentioned above, we can use the normal distribution to estimate the distribution of the test statistic above. The mean of the test statistic for H2 is 0.5, because the copy numbers of both G1 and G2 are identical on the reference chromosomes or chromosome segments and chromosomes or chromosome segments of interest. The mean of the test statistic for H3 is:

$$\frac{(1-4\%)/2 + 3/4*4\%}{1/2 + 1/2*(1-4\%) + 3/4*4\%} = 0.50495$$

We use the usual notation of $N(\mu,\sigma^2)$ to denote the normal distribution with mean $\mu$ and variance $\sigma^2$. Therefore, the distributions of the test statistic for the two hypotheses are:
H2: N(0.5, 0.25/n)
H3: N(0.50495, 0.25/n)

With this information, we can calculate what n is needed to attain a particular sensitivity and specificity. Suppose we want sensitivity and specificity to be 99%, we know that given a normal distribution, X, with mean 0 and variance 1, Prob(X<−2.326)=1%. We therefore solve for the following, $$\frac{(0.5 - 0.505)/2}{0.5/\sqrt{n}} < -2.326$$

to obtain n>220,827. Therefore, we need approximately 110,414 observations for each chromosome or chromosome segment. See Table 1 for the number of observations needed for each of the one or more reference chromosomes or chromosome segments and the one or more chromosomes or chromosome segments of interest for a range of mixture fractions and target sensitivity and specificity.

TABLE 1

Sequencing reads required for method 1 using various fractions of G2 in the sample and different target sensitivities and specificities.

|  |  | Target Sensitivity and Specificity | | | | | |
|---|---|---|---|---|---|---|---|
|  |  | 99.9% | 99.5% | 99% | 98% | 95% | 90% |
| Fraction of G2 in the sample | 0.5% | 12,253,983 | 8,513,913 | 6,944,554 | 5,412,398 | 3,471,759 | 2,107,498 |
|  | 1% | 3,071,150 | 2,133,796 | 1,740,476 | 1,356,480 | 870,108 | 528,191 |
|  | 2% | 771,622 | 536,113 | 437,292 | 340,814 | 218,613 | 132,707 |
|  | 3% | 344,651 | 239,459 | 195,320 | 152,227 | 97,645 | 59,275 |
|  | 4% | 194,830 | 135,365 | 110,413 | 86,053 | 55,198 | 33,508 |
|  | 5% | 125,309 | 87,063 | 71,015 | 55,347 | 35,502 | 21,551 |
|  | 6% | 87,450 | 60,759 | 49,560 | 38,626 | 24,776 | 15,040 |
|  | 7% | 64,566 | 44,860 | 36,591 | 28,518 | 18,293 | 11,104 |
|  | 8% | 49,677 | 34,515 | 28,153 | 21,941 | 14,074 | 8,544 |
|  | 9% | 39,443 | 27,405 | 22,353 | 17,422 | 11,175 | 6,784 |
|  | 10% | 32,106 | 22,307 | 18,195 | 14,181 | 9,096 | 5,522 |
|  | 15% | 14,619 | 10,157 | 8,285 | 6,457 | 4,142 | 2,514 |
|  | 20% | 8,423 | 5,852 | 4,773 | 3,720 | 2,386 | 1,449 |
|  | 25% | 5,520 | 3,835 | 3,128 | 2,438 | 1,564 | 949 |
|  | 30% | 3,924 | 2,726 | 2,224 | 1,733 | 1,112 | 675 |
|  | 35% | 2,950 | 2,050 | 1,672 | 1,303 | 836 | 507 |
|  | 40% | 2,311 | 1,606 | 1,310 | 1,021 | 655 | 397 |
|  | 45% | 1,868 | 1,298 | 1,058 | 825 | 529 | 321 |
|  | 50% | 1,547 | 1,075 | 877 | 683 | 438 | 266 |

Method 2 Using Allele Ratios

Similar to the quantitative approach described in Method 1, a molecule-based method that looks at the heterozygous rate at known SNPs can be used. In this approach, the test statistic for a SNP on the one or more chromosomes or chromosome segments of interest which can take on an allele value of A or B would be the observed rate of reference alleles. In particular, for a given SNP, let A and B denote the number of observed molecules with an A and B allele respectively. We can then define the heterozygous rate $$H = \frac{A}{A+B}$$

and the number of molecules at the SNP as $$N = A+B.$$

Let $A_1$ and $A_2$ denote the number of A alleles in genome G1 and G2, respectively, at the SNPs of interest. Similarly, $B_1$ and $B_2$ denote the number of B alleles in genome G1 and G2, respectively, at the SNPs of interest. The distribution of A is then a binomial distribution whose parameters are functions of $A_1$, $A_2$, $B_1$, $B_2$, and N. We assume that $A_1$ and $B_1$ are known and we want to estimate $A_2$ and $B_2$. We can do this by calculating the probability of the observed heterozygous rate H for all possible values of $A_2$ and $B_2$ and using Bayes rule to compute a probability of $A_2$ and $B_2$ given our observed H. For example, suppose that G2 represents 4% of the sample mixture (therefore, G1 is 96% of the mixture). Further, assume that G1 has two copies of each locus in the reference chromosomes or chromosome segments and the chromosomes or chromosome segments of interest. We want to consider two hypotheses of G2 having two or three copies. Denote these two hypotheses by H2 (G2 has two copies) and H3 (G2 has three copies), respectively. Under these assumptions, we can calculate the binomial parameter p for each hypothesis and values of $A_1$, $A_2$, $B_1$, and $B_2$ as $$p = \frac{0.96 * A_1 + 0.04 * A_2}{0.96 * A_1 + 0.04 * A_2 + 0.96 * B_1 + 0.04 * B_2}.$$

This gives us the following values for p (Table 2).

TABLE 2

Binomial parameter p values for different hypotheses and values of $A_1$, $A_2$, $B_1$, and $B_2$.
Binomial Parameter p

|  |  | ($A_1$ = 0, $B_1$ = 2) | ($A_1$ = 1, $B_1$ = 1) | ($A_1$ = 2, $B_1$ = 0) |
|---|---|---|---|---|
| H2 | ($A_2$ = 0, $B_2$ = 2) | 0 | 0.48 | 0.96 |
|  | ($A_2$ = 1, $B_2$ = 1) | 0.02 | 0.5 | 0.98 |
|  | ($A_2$ = 2, $B_2$ = 0) | 0.04 | 0.52 | 1 |
| H3 | ($A_2$ = 0, $B_2$ = 3) | 0 | 0.471 | 0.941 |
|  | ($A_2$ = 1, $B_2$ = 2) | 0.196 | 0.490 | 0.961 |
|  | ($A_2$ = 2, $B_2$ = 1) | 0.039 | 0.510 | 0.980 |
|  | ($A_2$ = 3, $B_2$ = 0) | 0.059 | 0.529 | 1 |

We further know that A is distributed bino(p·N) and that H has a Normal distribution with mean p and variance p(1−p)/N. As the number of nucleic acid molecules increases, the variance of the distributions decreases and the various hypotheses can be more easily distinguished. For example, given ($A_1$=1, $B_1$=1) and that we want to distinguish between H2 and H3. For the sake of simplicity, we will reduce the problem to distinguishing between ($A_2$=1, $B_2$=1) and ($A_2$=2, $B_1$=1). The above developed model can be used to calculate the minimum number of nucleic acid molecules necessary to achieve a specific specificity and sensitivity (Table 3).

in the sample necessary to have, with a certain probability, a particular number of nucleic acid molecules after the library and hybrid capture steps.

TABLE 3

Sequencing reads required for method 2 given various fractions of G2 in the sample and different target sensitivities and specificities.

| | | Target Sensitivity and Specificity | | | | | | | | |
|---|---|---|---|---|---|---|---|---|---|---|
| | | 99.9% | 99.8% | 99.5% | 99% | 98% | 95% | 90% | 85% | 80% |
| Fraction of G2 in the sample | 0.5% | 6,142,300 | 5,328,183 | 4,267,592 | 3,480,952 | 2,712,960 | 1,740,216 | 1,056,382 | 690,926 | 455,598 |
| | 1% | 1,543,243 | 1,338,698 | 1,072,226 | 874,584 | 681,627 | 437,227 | 265,414 | 173,594 | 114,468 |
| | 2% | 389,659 | 338,013 | 270,730 | 220,827 | 172,107 | 110,397 | 67,015 | 43,831 | 28,903 |
| | 3% | 174,901 | 151,719 | 121,519 | 99,119 | 77,251 | 49,552 | 30,080 | 19,674 | 12,973 |
| | 4% | 99,353 | 86,185 | 69,029 | 56,305 | 43,883 | 28,148 | 17,087 | 11,176 | 7,369 |
| | 5% | 64,211 | 55,700 | 44,613 | 36,390 | 28,361 | 18,192 | 11,043 | 7,223 | 4,763 |
| | 6% | 45,027 | 39,059 | 31,284 | 25,518 | 19,888 | 12,757 | 7,744 | 5,065 | 3,340 |
| | 7% | 33,403 | 28,976 | 23,208 | 18,930 | 14,754 | 9,464 | 5,745 | 3,757 | 2,478 |
| | 8% | 25,822 | 22,399 | 17,941 | 14,634 | 11,405 | 7,316 | 4,441 | 2,905 | 1,915 |
| | 9% | 20,599 | 17,869 | 14,312 | 11,674 | 9,098 | 5,836 | 3,543 | 2,317 | 1,528 |
| | 10% | 16,845 | 14,613 | 11,704 | 9,547 | 7,440 | 4,773 | 2,897 | 1,895 | 1,249 |
| | 15% | 7,848 | 6,807 | 5,452 | 4,447 | 3,466 | 2,223 | 1,350 | 883 | 582 |
| | 20% | 4,622 | 4,009 | 3,211 | 2,619 | 2,041 | 1,309 | 795 | 520 | 343 |
| | 25% | 3,094 | 2,684 | 2,150 | 1,753 | 1,367 | 877 | 532 | 348 | 229 |
| | 30% | 2,245 | 1,948 | 1,560 | 1,272 | 992 | 636 | 386 | 253 | 167 |
| | 35% | 1,722 | 1,494 | 1,196 | 976 | 761 | 488 | 296 | 194 | 128 |
| | 40% | 1,375 | 1,193 | 955 | 779 | 607 | 390 | 237 | 155 | 102 |
| | 45% | 1,132 | 982 | 787 | 642 | 500 | 321 | 195 | 127 | 84 |
| | 50% | 955 | 828 | 663 | 541 | 422 | 271 | 164 | 107 | 71 |

Practical Implications

Using the methods analyzed above and the efficiencies of sample preparation and library preparation, it is possible to calculate, for a particular sensitivity and specificity, the amount of sample required to obtain a specific number of unique sequencing reads. An exemplary workflow would be: sample collection→sample prep→library prep→hybrid capture→barcoding→sequencing. Based on this workflow, it is possible to work backwards to determine the sample requirements, given some assumptions about the efficiencies of each step. In this example, the barcoding step is assumed to have no significant impact. If N unique sequencing reads are required from a chromosome or chromosome segment, the preferred approach is to exhaustively sequence the nucleic acid molecules. Results based on the Coupon Collector's Problem (for example, see Dawkins, Brian (1991), "Siobhan's problem: the coupon collector revisited", The American Statistician, 45 (1): 76-82) can be used as guidance for how many sequence reads are necessary to have a particular probability of having sequenced all the nucleic acid molecules. See table below. For example, if there are 1,000 unique tagged nucleic acid molecules to be sequenced, a depth of read of approximately 12× is necessary to have a 99% probability of observing all the nucleic acid molecules. This estimate assumes that each sequence read is equally likely to be anyone of the 1,000 tagged nucleic acid molecules. If this is not the case, the calculated factor of 12 can be replaced with an empirically measured one. During the library prep and hybrid capture steps, some of the sample nucleic acid molecules present in the blood tube are lost. If we assume that 75% of molecules are lost in these processes (i.e., 25% of the sample nucleic acid molecules are retained), more nucleic acid molecules are required in the original to be sure there are sufficient tagged nucleic acid molecules remaining for barcoding. The binomial distribution can be used here to estimate the number of nucleic acid molecules in the sample necessary to have, with a certain probability, a particular number of nucleic acid molecules after the library and hybrid capture steps.

Based on the above reasoning, approximately 110,000 sequencing reads on both the reference chromosome or chromosome segment and the chromosome or chromosome segment of interest are necessary for 1% sensitivity and specificity in a mixture with 4% of G2 using method 1 (Table 1). If the combination of the library prep and hybrid capture steps has an overall efficiency of 25%, then more than 110,000 starting copies are needed in the sample. Using a simple binomial model, at least 443,000 sample nucleic acid molecules are required to ensure a greater than 99% chance of having at least 110,000 nucleic acid molecules available for barcoding and subsequent sequencing. Assuming the library preparation begins with 443,000 nucleic acid molecules, the expected number of sample nucleic acid molecules will be in the range of 110,000 to 111,400 molecules after the library prep and hybrid capture steps. To ensure measurement of all original molecules, the higher number can be used for further calculations, i.e., 111,400 nucleic acid molecules. Because of the variance in measuring nucleic acid molecules, to have a high probability of measuring all the 111,400 nucleic acid molecules, substantially more measurements are required. For example, to have a 99% probability of sequencing all the tagged nucleic acid molecules, it is necessary to sequence 16 times the number of nucleic acid molecules. Therefore, approximately 1,780,000 reads are required for each chromosomes or chromosome segment. This estimate assumes that each sequence read is equally likely to be any one of the 111,400 tagged nucleic acid molecules. If this is not the case, the calculated factor of 16 can be replaced with an empirically measured one.

In terms of the sample, as stated before, about 443,000 total sample nucleic acid molecules are required to attain the previously stated performance. The required 111,400 sequencing reads can be achieved by measuring multiple loci in each chromosome or chromosome segment. For example, if nucleic acid molecules at 1,000 different loci are measured, an average of about 112 unique nucleic acid molecules from each locus are required for sequencing, leading to an average of about 443 unique nucleic acid molecules in the starting sample. If the underlying sample type is a plasma sample from a human, it contains between 1,200 to 1,800 single haploid copies of the genome per ml of plasma. Further, on average 1 ml of blood sample contains approximately 0.5 ml of plasma. Thus, given these constraints, 1 ml of blood (0.5 ml plasma and 600-900 unique nucleic acid molecules from each locus) should be sufficient to determine the copy number of a chromosome or chromosome segment of interest.

The MITs can be used to here to count individual sample nucleic acid molecules and reduce the variance associated with other quantitative methods. To simplify counting of individual sample nucleic acid molecules, each sample nucleic acid molecule from a locus (i.e. each of the 443 nucleic acid molecules) should have a different combination of attached MITs. Given two MITs are being attached to each nucleic acid molecule, the number of possible combinations of attached MITs is $N^2$, where N is the number of MITs in the set. As there are approximately 443 copies of each locus, $N^2$ needs to be greater than 443. It is beneficial to have some buffer, so if $N^2$=1,000, N would be approximately 32. It is also possible to use the exact start and end genomic coordinates of the nucleic acid segment, in conjunction with the sequences of the MITs, to identify sample nucleic acid molecules.

Those skilled in the art can devise many modifications and other embodiments within the scope and spirit of the present disclosures. Indeed, variations in the materials, methods, drawings, experiments, examples, and embodiments described can be made by skilled artisans without changing the fundamental aspects of the present disclosures. Any of the disclosed embodiments can be used in combination with any other disclosed embodiment. All headings in this specification are for the convenience of the reader and do not limit the present disclosures in any way.

What is claimed is:

1. A reaction mixture comprising:
  a population of sample nucleic acid molecules between 10 and 1,000 nucleotides in length;
  a set of between 10 and 1000 different Molecular Index Tags (MITs) between 4 and 8 nucleotides in length; and
  a ligase,
  wherein the MITs are separate nucleic acid molecules from the sample nucleic acid molecules,
  wherein a ratio of the total number of sample nucleic acid molecules in the reaction mixture to the diversity of the MITs in the set of MITs in the reaction mixture is at least 10,000:1,
  wherein the sequence of each of the MITs in the set of MITs differs from all other MIT sequences in the set by at least 2 nucleotides; and
  wherein the reaction mixture comprises at least two copies of every MIT.

2. The reaction mixture of claim 1, wherein each MIT constitutes at least a portion of a double-stranded nucleic acid adapter molecule.

3. The reaction mixture of claim 1, wherein each MIT constitutes a portion of a Y-adapter nucleic acid molecule of a set of Y-adapter nucleic acid molecules, where each Y-adapter of the set comprises a base-paired, double-stranded polynucleotide segment and at least one non-base-paired single-stranded polynucleotide segment, wherein the sequence of each of the Y-adapter nucleic acid molecules in the set, other than the MIT sequence, is identical, and wherein the MIT is a double-stranded sequence that is part of the base-paired, double-stranded polynucleotide segment.

4. The reaction mixture of claim 3, wherein the double-stranded polynucleotide segment is between 5 and 25 nucleotides in length, not including the MIT, and the single-stranded polynucleotide segment is between 5 and 25 nucleotides in length.

5. The reaction mixture of claim 3, wherein the reaction mixture comprises circulating cell-free human DNA, wherein the number of combinations of any 2 MITs in the set of MITs exceeds the total number of sample nucleic acid molecules in the reaction mixture that span a target locus in the human genome, and wherein the total number of MIT molecules in the reaction mixture is at least two times greater than the total number of sample nucleic acid molecules in the reaction mixture.

6. The reaction mixture of claim 1, wherein the population of sample nucleic acid molecules comprises at least 500,000,000 sample nucleic acid molecules.

* * * * *

SEQUENCE LISTING

```
<160> NUMBER OF SEQ ID NOS: 14

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(39)
<223> OTHER INFORMATION: a, c, t, g, unknown or other

<400> SEQUENCE: 1
gcaatggtta ccgatactga gctcttccga tctnnnnnnt                            40

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other

<400> SEQUENCE: 2
nnnnnnagat cggaagagct tgcggat                                         27

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(39)
<223> OTHER INFORMATION: a, c, t, g, unknown or other
<220> FEATURE:
<221> NAME/KEY: modified_base
<222> LOCATION: (41)..(45)
<223> OTHER INFORMATION: a, c, t, g, unknown or other

<400> SEQUENCE: 3
```

```
gcaatggtta ccgatactga gctcttccga tctnnnnnnt nnnnn                45
```

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (7)..(12)
<223> OTHER INFORMATION: a, c, t, g, unknown or other

<400> SEQUENCE: 4

```
nnnnnannnn nnagatcgga agagcttgcg gat                             33
```

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
gcaatggtta ccgatactga gctcttccga tct                             33
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
gatcggaaga gcttgcggat                                            20
```

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(38)
<223> OTHER INFORMATION: a, c, t, g, unknown or other

<400> SEQUENCE: 7

```
gcaatggtta ccgatactga gctcttccga tctnnnnn                        38
```

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 8
nnnnnagatc ggaagagctt gcggat                                          26

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(20)
<223> OTHER INFORMATION: a, c, t, g, unknown or other

<400> SEQUENCE: 9
cacagtcgac atcannnnnn tccgcaagct cttccgatct                           40

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(6)
<223> OTHER INFORMATION: a, c, t, g, unknown or other

<400> SEQUENCE: 10
nnnnnngcaa tggttaccga tactgagctc ttccgatct                            39

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (40)..(44)
<223> OTHER INFORMATION: a, c, t, g, unknown or other

<400> SEQUENCE: 11
nnnnnngcaa tggttaccga tactgagctc ttccgatctn nnnn                      44

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (26)..(31)
<223> OTHER INFORMATION: a, c, t, g, unknown or other

<400> SEQUENCE: 12
nnnnnagatc ggaagagctt gcggannnnn ntgatgtcga ctgtg                     45

```
<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (39)..(44)
<223> OTHER INFORMATION: a, c, t, g, unknown or other

<400> SEQUENCE: 13
nnnnnagatc ggaagagctc agtagcggta accattgcnn nnnn            44

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(20)
<223> OTHER INFORMATION: a, c, t, g, unknown or other
<220> FEATURE:
<221> NAME/KEY: modified_base
<222> LOCATION: (41)..(45)
<223> OTHER INFORMATION: a, c, t, g, unknown or other

<400> SEQUENCE: 14
cacagtcgac atcannnnnn tccgcaagct cttccgatct nnnnn           45
```